US007902238B2

(12) United States Patent
Galley et al.

(10) Patent No.: US 7,902,238 B2
(45) Date of Patent: Mar. 8, 2011

(54) 2-AMINOOXAZOLINES AS TAAR1 LIGANDS

(75) Inventors: Guido Galley, Rheinfelden (DE); Katrin Groebke Zbinden, Liestal (CH); Roger Norcross, Olsberg (CH); Henri Stalder, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 274 days.

(21) Appl. No.: 12/028,028

(22) Filed: Feb. 8, 2008

(65) Prior Publication Data
US 2009/0105307 A1 Apr. 23, 2009

(30) Foreign Application Priority Data

Feb. 15, 2007 (EP) .................................... 07102429

(51) Int. Cl.
A61K 31/42 (2006.01)
C07D 263/28 (2006.01)
(52) U.S. Cl. ........................ 514/374; 548/233
(58) Field of Classification Search .................. None
See application file for complete search history.

(56) References Cited

U.S. PATENT DOCUMENTS

| | | | |
|---|---|---|---|
| 2,161,938 A | 6/1939 | Sonn | |
| 2,457,047 A | 12/1948 | Kyrides | |
| 2,731,471 A | 1/1956 | Synerholm et al. | |
| 2,744,909 A | 5/1956 | Speeter | |
| 2,744,910 A | 5/1956 | Speeter | |
| 2,778,836 A | 1/1957 | Morren | |
| 2,919,274 A | 12/1959 | Faust et al. | |
| 3,161,653 A | 12/1964 | Fruhstorfer et al. | |
| 3,354,175 A | 11/1967 | Fruhstorfer et al. | |
| 3,377,247 A | 4/1968 | Eble | |
| 3,577,428 A | 5/1971 | Suh et al. | |
| 3,586,695 A | 6/1971 | Wysong et al. | |
| 3,622,579 A | 11/1971 | Stahle et al. | |
| 3,660,423 A | 5/1972 | Wysong et al. | |
| 3,758,476 A | 9/1973 | Rippel et al. | |
| 3,818,035 A | 6/1974 | Binon et al. | |
| 3,818,094 A | 6/1974 | Stahle et al. | |
| 3,992,403 A | 11/1976 | Roebke | |
| 4,125,620 A | 11/1978 | Stahler et al. | |
| 4,146,647 A | 3/1979 | Lafon | |
| 4,311,840 A | 1/1982 | Condon | |
| 4,323,570 A | 4/1982 | Stenzel et al. | |
| 4,665,095 A | 5/1987 | Winn et al. | |
| 5,610,174 A | 3/1997 | Craig et al. | |
| 5,658,938 A | 8/1997 | Geerts et al. | |
| 6,268,389 B1 | 7/2001 | Esser et al. | |
| 7,098,228 B2 | 8/2006 | Binggeli et al. | |
| 2002/0019390 A1 | 2/2002 | Wong et al. | |
| 2003/0181354 A1 | 9/2003 | Abdulrazik | |
| 2003/0236274 A1 | 12/2003 | Tasaka et al. | |

FOREIGN PATENT DOCUMENTS

| CA | 2 246 027 | 2/2000 |
|---|---|---|
| DE | 842 065 | 6/1952 |
| DE | 17 95 517 | 2/1972 |
| DE | 22 03 373 | 8/1972 |
| DE | 2 253 555 | 11/1972 |
| DE | 24 46 758 | 4/1976 |
| DE | 28 49 537 | 5/1980 |
| EP | 0 024 829 | 3/1981 |
| EP | 0 125 410 | 11/1984 |
| EP | 0 166 937 | 1/1986 |
| EP | 0 167 459 | 1/1986 |
| EP | 0 331 374 | 9/1989 |
| EP | 0 424 059 | 4/1991 |
| EP | 0 717 037 | 6/1996 |
| EP | 0 857 483 | 8/1998 |
| EP | 0 924 209 | 6/1999 |
| EP | 1 103 243 | 5/2001 |
| EP | 1 413 576 | 4/2004 |
| ES | 323 985 | 12/1966 |
| FR | 1 355 049 | 3/1964 |
| FR | 6 551 | 12/1968 |
| GB | 877306 | 9/1961 |
| GB | 1 016 514 | 1/1996 |
| WO | WO 96/22768 | 8/1996 |
| WO | WO 97/12874 | 4/1997 |
| WO | WO 98/12183 | 3/1998 |
| WO | WO 01/30762 | 5/2001 |
| WO | WO 01/81334 | 11/2001 |
| WO | WO 02/22801 | 3/2002 |
| WO | WO 02/40453 | 5/2002 |
| WO | WO 02/076950 | 10/2002 |
| WO | WO 03/092374 | 11/2003 |
| WO | WO 2004/014898 | 2/2004 |
| WO | 2005/016267 | 2/2005 |

(Continued)

OTHER PUBLICATIONS

Deutch et al., (1999) Neurotransmitters. In Fundamental Neuroscien ($2^{nd}$ ed.) pp. 193-234, Academic Press.
Wong, et al., (2001) Nat. Rev. Neurosci. 2, pp. 343-351.
Carlsson et al. (2001) Annu. Rev. Pharmacol. Toxicol. 41, pp. 237-2.
Tuite et al. (2003) Expert Opin. Investig. Drugs 12, pp. 1335-1352.
Castellanos et al., (2002) Nat. Rev. Neurosci. 3, pp. 617-628.
Usdin, E. and Sandler. M.; Editors. Psychopharmacology Series, V Trace Amines and the Brain. [Proceedings of a Study Group at the 14th Annual Meeting of the American College of Neuropsychoparmacology, Juan, Puerto Rico] (1976) pp. 1-281.
Lindemann et al., (2005) Trends in Pharmacol. Sci. 26, pp. 274-281.
Branchek et al., (2003) Curr. Opin. Pharmacol. 3, pp. 90-97.

(Continued)

*Primary Examiner* — Kamal A Saeed
(74) *Attorney, Agent, or Firm* — George W. Johnston; Patricia S. Rocha-Tramaloni; Kimberly J. Prior

(57) ABSTRACT

The invention relates to compounds of formula

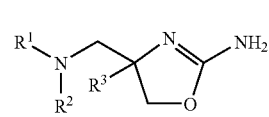

wherein
$R^1$, $R^2$, and $R^3$ are as defined herein and to a pharmaceutically suitable acid addition salts thereof for the treatment of CNS disorders.

31 Claims, No Drawings

FOREIGN PATENT DOCUMENTS

| | | |
|---|---|---|
| WO | WO 2006/119411 | 11/2006 |
| WO | WO 2007/024944 | 3/2007 |
| WO | 2008/074679 | 6/2008 |
| WO | 2008/092785 | 8/2008 |

OTHER PUBLICATIONS

Premont et al. (2001) Proc. Natl. Acad. Sci. U. S. A. 98, pp. 9474-94.
Mosseau et al., (1995) Prog. Brain Res. 106, pp. 285-291.
McCormack et al. (1986) J. Neurosci. 6, pp. 94-101.
Dyck, L.E. (1989) Life Sci. 44, pp. 1149-1156.
Parker et al., (1988) J. Pharmacol. Exp. Ther. 245, pp. 199-210.
Lindemann et al. (2005) Genomics 85, pp. 372-385.
Habib et al., Synthesis, 1984, pp. 825-827.
Trani et al., J. Heterocycl. Chem. 11, pp. 257-262 (1974).
Bunzow, J.R., et al., Molecular Pharmacology, vol. 60(6), pp. 1181-1188 (2001), XP008008060.
Holt, Andrew, J. of Psychiatry & Neuroscience, vol. 28(6), pp. 40 414 (2003), XP002438693.
Timmermans, P B M W M, et al., Life Sciences, vol. 28, No. 6, pp. 653-660 (1981), XP002442517.
Prisinzano, Thomas, et al., Bioorganic & Medicinal Chemistry Letters, vol. 14, No. 18, pp. 4697-4699 (2004), XP002442518.
Olmos, G., et al., European Journal of Pharmacology, vol. 262, No. ½ pp. 41-48 (1994), XP000567119.
McLennan, P.L., European Journal of Pharmacology, vol. 69, No. 4, 477-482 (1981), XP002442519.
Nathanson, J.A., Molecular Pharmacology, vol. 28., No. 3, pp. 25 268 (1985), XP009085722.
Akinori, et al., Bioorganic and Medicinal Chemistry, vol. 10, No. 1, 117-123 (2002), XP002442520.
Flippin et al., Tetrahedron Letters, vol. 34, pp. 3255-3258 (1993).
Liebigs, Ann. Chem. pp. 2061-2071 (1980).
Huh et al., Tetrahedron, vol. 58, pp. 9925-9932 (2002).
Huh et al., Tetrahedron, vol. 60, pp. 9857-9862 (2004).
Law et al., J. Med. Chem. vol. 41, pp. 2243-2251 (1998).
Debernardis et al., J. Med. Chem. vol. 29, pp. 1413-1417 (1986).
Mohammadpoor-Baltork, Bull. Korean Chem. Soc. vol. 24, p. 1354-1356 (2003).
Melloni et al., Eur. J. Med. Chem. vol. 26, pp. 207-213 (1991).
Abdollahi-Alibeik et al., Bioorg. Med. Chem. Lett. vol. 14, pp. 60 6082 (2004).
Amemiya, Synth. Commun. vol. 20, pp. 2483-2489 (1990).
Ohta, Chem. Pharm. Bull. vol. 35, pp. 1058-1069 (1987).
Olah, Synlett pp. 647-650 (1992).
Katz et al., Tetrahedron, vol. 45, pp. 1801-1814 (1989).
Wentland et al., J. Med. Chem. vol. 30, pp. 1482-1489 (1987).
Campos et al., Heterocycles, vol. 40, p. 841-849 (1995).
Ohta, Synthesis, pp. 78-81 (1990).
Mancuso et al., J. Org. Chem. vol. 43, pp. 2480-2482 (1978).
Mohammadpoor-Baltork, Synlett, pp. 2803-2805 (2004).
Cahiez et al., Synthesis, pp. 2138-2144 (1999).
Evans et al., Tetrahedron Lett. vol. 39, pp. 2937-2940 (1998).
Nakamura et al., J. Chem. Soc. Perkin Trans. 1, pp. 1061-1066 (2002.
Amemiya, et al., J. of Medicinal Chemistry, vol. 35(4), pp. 750-755 (1992), XP002151512.
Savola, J.M., et al., Drug Research, vol. 38(1), pp. 29-35 (1988), XP002033085.
Turner, et al., J. Org. Chem. (1991), 56, pp. 5739-5740.
Matsunaga, et al., Bioorganic & Medicinal Chemistry, p. 4314-43 (2004), XP002444990.
Matsunaga, et al., Tetrahedron: Asymmetry, Elsevier Science Publishers, vol. 15, No. 13, pp. 2021-2028 (2004), XP004520137.
Ojida, A., et al., Tetrahedron: Asymmetry, Elsevier Science Publishers vol. 15, No. 10, pp. 1555-1559 (2004), XP004508431.
Zhang, et al., Journal of Medicinal Chemistry, vol. 40, pp. 3014-302 (1997), XP002108693.
Ojida et al., Org. Lett. 2002, 4, pp. 3051-3054 (Supporting document attached).
Khimiya Geterotsiklicheskikh Soedinenii, 1988, pp. 77-79 (English lang abstract attached).
Reimann et al., Arch. Pharm. 1989, vol. 322, pp. 363-367.
Klapars, et al., J. Am. Chem. Soc. 2001, vol. 123, pp. 7727-7729.
Anderson, et al., Tetrahedron, 2002, vol. 58, pp. 8475-8481.
Touzeau et al., J. Med. Chem. 2003, vol. 46, pp. 1962-1979.
Debernardis et al., Conformationally Defined Adregernic Agents. Resolution, Absolute Configuration, and Pharmacological Characterizat of the Enantiomers of 2-(5,6-Dihydroxy-1,2,3,4-tetrahydro-1-naphthyl)imidazoline: A Potent Agonist at $\alpha$-Adrenoceptors, J. Med. C (1987), 30:1011-1017.
Altenbach et al., Synthesis and Structure-Activity Studies on $N$-[5-(Imidazol-4-yl)-5,6,7,8-tetrahydro-1-naphthalenyl]methanesulfonamide, Imidasole-Containing $\alpha_{1A}$-Adrenoceptor Agonist, J. Med. Chem. (2004) 3220-3235.
Carroll et al., In Vitro and In Vivo Characterization of Alpha-1A Selective Agonists and Their Utility for Stress Incontinence, Med. Chem Res. (2004), 13:134-148.
Jetter et al., Synthesis of 4-Substituted Imidazoles via Palladium-Catalyzed Cross-Coupling Reactions, Synthesis (1998), 829-831.
Bagley et al., Synthesis and $\alpha_2$-Adrenegeric Activities of Imidazole and Imidazolidine Analogues: In Vitro and In Vivo Selectivity, Medicinal Chemistry Research (1994), 4:346-364.
Lee et al., 4-[($N$-Imidazol-2-ylmethyl)aniline]pyranopyridine Analogs a Novel Anti-Angiogenic Agents, Bull. Korean Chem. Soc. (2005), 25: 61 628.
Agami et al., Tetrahedron 2001, vol. 57(1) pp. 195-200.
Ueda et al., Bioorganic & Medicinal Chem. Letters 2004, vol. 14(2) p. 313-316.
Chilean Office Action in related Chilean Appl No. 434-2008 dated Jul. 1, 2010.

ache, eating disorders, metabolic disorders and therefore TAAR1 ligands have a high potential for the treatment of these diseases.

Therefore, there is a broad interest to increase the knowledge about trace amine associated receptors.

2-AMINOOXAZOLINES AS TAAR1 LIGANDS

PRIORITY TO RELATED APPLICATION(S)

This application claims the benefit of European Patent Application No. 07102429.3, filed Feb. 15, 2007, which is hereby incorporated by reference in its entirety.

BACKGROUND OF THE INVENTION

Some of physiological effects, (i.e. cardiovascular effects, hypotension, induction of sedation have been reported for compounds which may bind to adrenergic receptors (WO02/076950, WO97/12874 or EP 0717 037). These physiological effects may be considered to be undesirable side effects in the case of medicaments aimed at treating diseases of the central nervous system as described above. Therefore it is desirable to obtain medicaments having selectivity for the TAAR1 receptor vs adrenergic receptors. Objects of the present invention show selectivity for TAAR1 receptor over adrenergic receptor, in particular good selectivity vs the human and rat alpha1 and alpha2 receptors."

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlap with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the aetiology of various diseases like depression, psychosis, attention deficit hyperactivity disorder, substance abuse, Parkinson's disease, migraine head-

REFERENCES USED

1 Deutch, A. Y. and Roth, R. H. (1999) Neurotransmitters. In *Fundamental Neuroscience* (2$^{nd}$ edn) (Zigmond, M. J., Bloom, F. E., Landis, S. C., Roberts, J. L, and Squire, L. R., eds.), pp. 193-234, Academic Press;

2 Wong, M. L. and Licinio, J. (2001) Research and treatment approaches to depression. *Nat. Rev. Neurosci.* 2, 343-351;

3 Carlsson, A. et al. (2001) Interactions between monoamines, glutamate, and GABA in schizophrenia: new evidence. *Annu. Rev. Pharmacol. Toxicol.* 41, 237-260;

4 Tuite, P. and Riss, J. (2003) Recent developments in the pharmacological treatment of Parkinson's disease. *Expert Opin. Investig. Drugs* 12, 1335-1352, 5 Castellanos, F. X. and Tannock, R. (2002) Neuroscience of attention-deficit/hyperactivity disorder: the search for endophenotypes. *Nat. Rev. Neurosci.* 3, 617-628;

6 Usdin, Earl; Sandler, Merton; Editors. *Psychopharmacology Series, Vol. 1: Trace Amines and the Brain. [Proceedings of a Study Group at the 14th Annual Meeting of the American College of Neuropsychoparmacology*, San Juan, Puerto Rico] (1976);

7 Lindemann, L. and Hoener, M. (2005) A renaissance in trace amines inspired by a novel GPCR family. *Trends in Pharmacol. Sci.* 26, 274-281;

8 Branchek, T. A. and Blackburn, T. P. (2003) Trace amine receptors as targets for novel therapeutics: legend, myth and fact. *Curr. Opin. Pharmacol.* 3, 90-97;

9 Premont, R. T. et al. (2001) Following the trace of elusive amines. *Proc. Natl. Acad. Sci. U.S. A.* 98, 9474-9475;

10 Mousseau, D. D. and Butterworth, R. F. (1995) A high-affinity [3H] tryptamine binding site in human brain. *Prog. Brain Res.* 106, 285-291;

11 McCormack, J. K. et al. (1986) Autoradiographic localization of tryptamine binding sites in the rat and dog central nervous system. *J. Neurosci.* 6, 94-101;

12 Dyck, L. E. (1989) Release of some endogenous trace amines from rat striatal slices in the presence and absence of a monoamine oxidase inhibitor. *Life Sci.* 44, 1149-1156;

13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;

14 Lindemann, L. et al. (2005) Trace amine associated receptors form structurally and functionally distinct subfamilies of novel G protein-coupled receptors. *Genomics* 85, 372-385.

SUMMARY OF THE INVENTION

The invention provides compounds of formula I

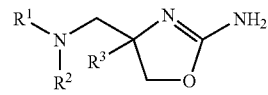

I wherein
R¹ is aryl or heteroaryl, wherein the aryl and heteroaryl groups are unsubstituted or substituted by one to three substituents, selected from the group consisting of cycloalkyl, phenyl, phenyloxy, benzyl, benzyloxy, halogen, lower alkyl, lower alkoxy, heteroaryl, piperidin-1-yl, and lower alkyl substituted by halogen, or is aryl or heteroaryl wherein at least one hydrogen atom is replaced by deuterium or tritium;
R² is hydrogen, lower alkyl or is benzyl unsubstituted or substituted by alkoxy or halogen; or
R¹ and R² together with the N-atom to which they are attached form 2,3-dihydroindol-1 yl or 3,4-dihydro-quinolin-1-yl; and
R³ is hydrogen or lower alkyl
and pharmaceutically suitable acid addition salts thereof.

The invention includes all racemic mixtures, all their corresponding enantiomers and/or optical isomers.

In addition, all tautomeric forms of compounds of formula I are also encompassed by the present invention.

The invention also provides pharmaceutical compositions containing a therapeutically effective amount of a compound of formula I or a pharmaceutically acceptable acid addition salt thereof and a pharmaceutically acceptable carrier. The invention further provides methods for the manufacture of the compounds and compositions of the invention.

Compounds of formula I have a good affinity to the trace amine associated receptors (TAARs), especially for TAAR1.

The compounds can be used for the treatment of anxiety disorders, depression, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety and attention deficit hyperactivity disorder (ADHD).

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes an alkyl residue as defined above, which is attached via an oxygen atom.

As used herein, the term "lower alkyl substituted by halogen" denotes an alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like.

The term "halogen" denotes chlorine, iodine, fluorine and bromine.

The term "cycloalkyl" denotes a monovalent saturated carbocyclic moiety. Cycloalkyl can optionally be substituted with one, two, three or four substituents, wherein each substituent is independently hydroxy, $C_{1-6}$-alkyl, $C_{1-6}$-alkoxy, halogen, amino, unless otherwise specifically indicated. Examples of cycloalkyl moieties include optionally substituted cyclopropyl, optionally substituted cyclobutyl, optionally substituted cyclopentyl and optionally substituted cyclohexyl as well as those specifically illustrated by the examples herein below.

The term "aryl" as used herein is a carbocyclic ring system, containing from 6 to 10 carbon atoms forming one or more rings, and wherein at least one ring is aromatic in nature, for example phenyl, naphthyl, 5,6,7,8-tetrahydronaphthalen-1-yl or indan-5-yl.

The term "heteroaryl" as used herein is a ring system, containing from 5 to 10 ring atoms forming one or more rings, wherein at least one carbon atom is replaced by a heteroatom, selected from the group consisting of O, N and S, and wherein at least one ring is aromatic in nature, for example oxazolyl, pyridyl, pyrimidinyl, thiophenyl, quinolinyl, pyrrolyl, furyl, imidazolyl and the like.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

A preferred embodiment of the invention relates to compounds of formula

I-A

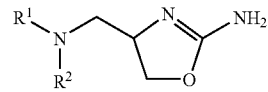

wherein
R¹ is aryl, wherein the aryl group is unsubstituted or substituted by one to three substituents, selected from the group consisting of cycloalkyl, phenyl, phenyloxy, benzyl, benzyloxy, halogen, lower alkyl, lower alkoxy, heteroaryl, and lower alkyl substituted by halogen, or is aryl wherein at least one hydrogen atom is replaced by deuterium or tritium; and
R² is hydrogen, lower alkyl or is benzyl unsubstituted or substituted by alkoxy; or
R¹ and R² together with the N-atom to which they are attached form 2,3-dihydroindol-1 yl or 3,4-dihydro-quinolin-1-yl;
or to a pharmaceutically suitable acid addition salt thereof.

Preferred compounds of formula I are those, wherein R¹ is unsubstituted phenyl and R² is lower alkyl, for example the following compounds:
(R)-4-[(ethyl-phenyl-amino)-methyl]-4,5-dihydro-oxazol-2-ylamine,
(S)-4-[(ethyl-phenyl-amino)-methyl]-4,5-dihydro-oxazol-2-ylamine, and (S)-4-[(methyl-phenyl-amino)-methyl]-4,5-dihydro-oxazol-2-ylamine.

Further preferred compounds are those, wherein $R^1$ is phenyl substituted by halogen and $R^2$ is lower alkyl, for example the following compounds
(S)-4-{[(3,4-dichloro-phenyl)-methyl-amino]-methyl}-4,5-dihydro-oxazol-2-ylamine,
(S)-4-{[(4-chloro-phenyl)-ethyl-amino]-methyl}-4,5-dihydro-oxazol-2-ylamine,
(S)-4-{[(3,4-dichloro-phenyl)-isopropyl-amino]-methyl}-4,5-dihydro-oxazol-2-ylamine,
(S)-4-{[(4-bromo-phenyl)-methyl-amino]-methyl}-4,5-dihydro-oxazol-2-ylamine,
(S)-4-{[(4-bromo-phenyl)-ethyl-amino]-methyl}-4,5-dihydro-oxazol-2-ylamine,
(S)-4-{[(3,4-dichloro-phenyl)-ethyl-amino]-methyl}-4,5-dihydro-oxazol-2-ylamine,
(S)-4-{[(3-bromo-phenyl)-methyl-amino]-methyl}-4,5-dihydro-oxazol-2-ylamine,
(S)-4-{[(3-bromo-phenyl)-ethyl-amino]-methyl}-4,5-dihydro-oxazol-2-ylamine,
(S)-4-{[(3-chloro-phenyl)-ethyl-amino]-methyl}-4,5-dihydro-oxazol-2-ylamine,
(S)-4-{[(4-chloro-2-fluoro-phenyl)-ethyl-amino]-methyl}-4,5-dihydro-oxazol-2-ylamine,
(S)-4-{[(4-chloro-2-fluoro-phenyl)-methyl-amino]-methyl}-4,5-dihydro-oxazol-2-ylamine,
(S)-4-{[ethyl-(2-fluoro-phenyl)-amino]-methyl}-4,5-dihydro-oxazol-2-ylamine,
(S)-4-{[(2-chloro-phenyl)-ethyl-amino]-methyl}-4,5-dihydro-oxazol-2-ylamine,
(R)-4-{[(4-chloro-phenyl)-methyl-amino]-methyl}-4,5-dihydro-oxazol-2-ylamine,
(R)-4-{[(4-chloro-phenyl)-ethyl-amino]-methyl}-4,5-dihydro-oxazol-2-ylamine,
(R)-4-{[(4-fluoro-phenyl)-methyl-amino]-methyl}-4,5-dihydro-oxazol-2-ylamine,
(R)-4-{[(4-chloro-phenyl)-isopropyl-amino]-methyl}-4,5-dihydro-oxazol-2-ylamine,
(S)-4-{[(2,4-difluoro-phenyl)-ethyl-amino]-methyl}-4,5-dihydro-oxazol-2-ylamine,
(S)-4-{[(2,4-difluoro-phenyl)-methyl-amino]-methyl}-4,5-dihydro-oxazol-2-ylamine,
(R)-4-{[(3,4-dichloro-phenyl)-methyl-amino]-methyl}-4,5-dihydro-oxazol-2-ylamine,
(R)-4-{[(3,4-dichloro-phenyl)-ethyl-amino]-methyl}-4,5-dihydro-oxazol-2-ylamine,
(R)-4-{[(3,4-dichloro-phenyl)-isopropyl-amino]-methyl}-4,5-dihydro-oxazol-2-ylamine,
(S)-4-{[(3,5-dichloro-phenyl)-methyl-amino]-methyl}-4,5-dihydro-oxazol-2-ylamine, and
(S)-4-{[(3,5-dichloro-phenyl)-ethyl-amino]-methyl}-4,5-dihydro-oxazol-2-ylamine.

Further preferred compounds are those, wherein $R^1$ is phenyl substituted by halogen or $CF_3$, and $R^2$ is hydrogen, for example the following compounds
(S)-4-[(3-chloro-phenylamino)-methyl]-4,5-dihydro-oxazol-2-ylamine,
(S)-4-[(2-chloro-phenylamino)-methyl]-4,5-dihydro-oxazol-2-ylamine,
(S)-4-[(4-trifluoromethyl-phenylamino)-methyl]-4,5-dihydro-oxazol-2-ylamine, and
(S)-4-[(2,4-difluoro-phenylamino)-methyl]-4,5-dihydro-oxazol-2-ylamine.

Further preferred compounds are those, wherein $R^1$ is phenyl substituted by halogen and lower alkyl, and $R^2$ is hydrogen, for example
(S)-4-[(2-fluoro-4-methyl-phenylamino)-methyl]-4,5-dihydro-oxazol-2-ylamine.

Further preferred compounds are those, wherein $R^1$ is phenyl substituted by $CF_3$ and lower alkyl or $CF_3$ alone and $R^2$ is lower alkyl, for example the following compounds
(S)-4-{[ethyl-(4-trifluoromethyl-phenyl)-amino]-methyl}-4,5-dihydro-oxazol-2-ylamine,
(S)-4-{[methyl-(4-trifluoromethyl-phenyl)-amino]-methyl}-4,5-dihydro-oxazol-2-ylamine, and
(S)-4-{[ethyl-(2-methyl-4-trifluoromethyl-phenyl)-amino]-methyl}-4,5-dihydro-oxazol-2-ylamine.

Further preferred compounds are those, wherein $R^1$ is phenyl substituted by $CF_3$ and lower alkyl or $CF_3$ alone and $R^2$ is lower alkyl, for example, the following compounds
(S)-4-{[ethyl-(4-trifluoromethyl-phenyl)-amino]-methyl}-4,5-dihydro-oxazol-2-ylamine,
(S)-4-{[methyl-(4-trifluoromethyl-phenyl)-amino]-methyl}-4,5-dihydro-oxazol-2-ylamine, and
(S)-4-{[ethyl-(2-methyl-4-trifluoromethyl-phenyl)-amino]-methyl}-4,5-dihydro-oxazol-2-ylamine.

Further preferred compounds are those, wherein $R^1$ is pyridine-2-yl and $R^2$ is lower alkyl, for example the following compound
((S)-2-amino-4,5-dihydro-oxazol-4-ylmethyl)-(6-chloro-pyridin-2-yl)-amine.

Further preferred compounds are those, wherein $R^1$ is phenyl, substituted simultaneously by halogen and methoxy, for example
(S)-4-{[(4-chloro-3-methoxy-phenyl)-methyl-amino]-methyl}-4,5-dihydro-oxazol-2-ylamine,
(S)-4-{[(4-chloro-3-methoxy-phenyl)-ethyl-amino]-methyl}-4,5-dihydro-oxazol-2-ylamine,
(S)-4-{[(4-fluoro-3-methoxy-phenyl)-methyl-amino]-methyl}-4,5-dihydro-oxazol-2-ylamine,
(R)-4-{[(4-fluoro-3-methoxy-phenyl)-methyl-amino]-methyl}-4,5-dihydro-oxazol-2-ylamine,
(R)-4-{[ethyl-(4-fluoro-3-methoxy-phenyl)-amino]-methyl}-4,5-dihydro-oxazol-2-ylamine,
(R)-4-{[(4-chloro-3-methoxy-phenyl)-methyl-amino]-methyl}-4,5-dihydro-oxazol-2-ylamine, and
(R)-4-{[(4-chloro-3-methoxy-phenyl)-ethyl-amino]-methyl}-4,5-dihydro-oxazol-2-ylamine.

Preferred compounds of formula I are further those, wherein $R^1$ is phenyl, substituted simultaneously by halogen and methoxy or by halogen and $R^2$ is benzyl, for example
(S)-4-{[benzyl-(4-fluoro-3-methoxy-phenyl)-amino]-methyl}-4,5-dihydro-oxazol-2-ylamine,
(S)-4-{[benzyl-(4-fluoro-phenyl)-amino]-methyl}-4,5-dihydro-oxazol-2-ylamine, and
(S)-4-{[benzyl-(4-chloro-phenyl)-amino]-methyl}-4,5-dihydro-oxazol-2-ylamine.

Preferred compounds of formula I are further those, wherein $R^1$ is phenyl, substituted by lower alkyl and $R^2$ is lower alkyl, for example the following compounds
(S)-4-[(ethyl-m-tolyl-amino)-methyl]-4,5-dihydro-oxazol-2-ylamine,
(S)-4-{[ethyl-(3-ethyl-phenyl)-amino]-methyl}-4,5-dihydro-oxazol-2-ylamine, and
(S)-4-{[ethyl-(4-ethyl-phenyl)-amino]-methyl}-4,5-dihydro-oxazol-2-ylamine.

Preferred compounds of formula I are further those, wherein $R^1$ is naphthyl, and $R^2$ is lower alkyl, for example the following compounds
(S)-4-[(methyl-naphthalen-2-yl-amino)-methyl]-4,5-dihydro-oxazol-2-ylamine,
(R)-4-[(methyl-naphthalen-2-yl-amino)-methyl]-4,5-dihydro-oxazol-2-ylamine, and
(R)-4-[(ethyl-naphthalen-2-yl-amino)-methyl]-4,5-dihydro-oxazol-2-ylamine.

Preferred compounds of formula I are further those, wherein $R^1$ is phenyl, substituted by halogen and $CF_3$, for example (S)-4-{[ethyl-(3-fluoro-5-trifluoromethyl-phenyl)-amino]-methyl}-4,5-dihydro-oxazol-2-ylamine,
(S)-4-[(3-fluoro-4-trifluoromethyl-phenylamino)-methyl]-4,5-dihydro-oxazol-2-ylamine, and
(R)-4-{[ethyl-(3-fluoro-5-trifluoromethyl-phenyl)-amino]-methyl}-4,5-dihydro-oxazol-2-ylamine.

Preferred compounds of formula I are further those, wherein R¹ is indanyl, and R² is lower alkyl, for example the following compound
(S)-4-[(ethyl-indan-5-yl-amino)-methyl]-4,5-dihydro-oxazol-2-ylamine.

Preferred compounds of formula I are further those, wherein R¹ is phenyl, substituted by heteroaryl, for example the following compounds
(S)-4-{[methyl-(3-oxazol-5-yl-phenyl)-amino]-methyl}-4,5-dihydro-oxazol-2-ylamine, and
(S)-4-{[ethyl-(3-oxazol-5-yl-phenyl)-amino]-methyl}-4,5-dihydro-oxazol-2-ylamine.

The present compounds of formula I and their pharmaceutically acceptable salts can be prepared by methods known in the art, for example, by processes described below, which processes comprise
a) reacting a compound of formula

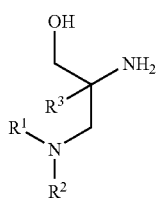

II with cyanogen bromide
to obtain a compound of formula

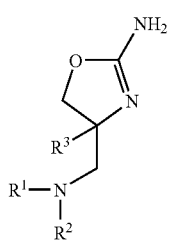

I wherein the definitions are as described above, or b) deprotecting a compound of formula

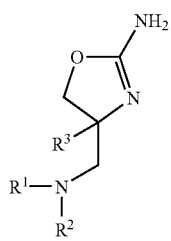

I for R² being benzyl or benzyl substituted by alkoxy
to obtain a compound of formula

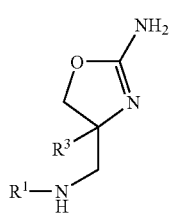

I-1 wherein the definitions are as described above, or
if desired, converting the compounds obtained into pharmaceutically acceptable acid addition salts.

The compounds of formula I can be prepared in accordance with the process variants as described above and with the following schemes 1-4. The starting materials are commercially available (e.g. from one or more of the following chemical suppliers such as Aldrich, Fluka, Acros, Maybridge, Avocado, TCI, or additional suppliers as indicated in databases such as Chemical Abstracts [American Chemical Society, Columbus, Ohio] or Available Chemicals Directory [Elsevier MDL, San Ramon, Calif.]), or are otherwise known in the chemical literature, or can be prepared as described in the Examples section.

General Procedure 1

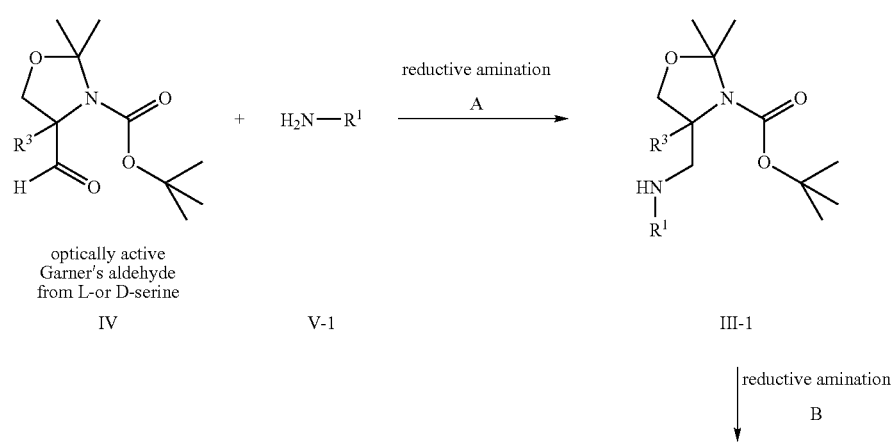

Scheme 1

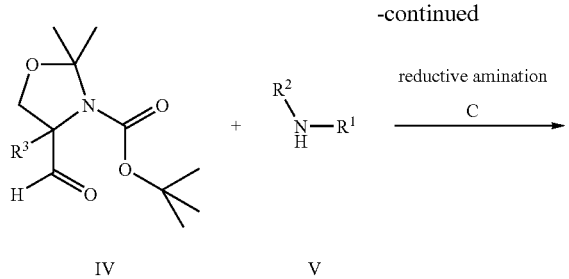 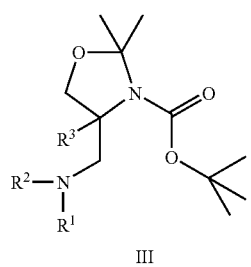

IV   V   III

Step A: Reductive amination of optically active Garner's aldehyde ($R^3$=H; from L- or D-serine; Garner, P.; Park, J. M. *Org. Synth.* 1998, IX, 300) or α-methyl-substituted Garner's aldehyde ($R^3$=methyl; from L- or D-α-methylserine; Avenoza, A. et al. *Tetrahedron Asymm.* 2001, 12, 949) with a compound of formula V-1 can be accomplished by a reducing agent such as $NaBH_4$, $LiBH_4$, $NaBH(OAc)_3$ or $Na(CN)BH_3$ in a solvent such as MeOH, EtOH, dichloromethane, 1,2-dichloroethane, THF, dioxane or mixtures thereof in the presence of an activating protic acid such as HCl or a carboxylic acid or an activating Lewis acid such as $ZnCl_2$ or $Ti(OiPr)_4$ at a temperature of −10 to 60° C. for 1-40 h.

Preferred conditions for $R^1$=aryl and $R^3$=H are $NaBH_3CN$ and $ZnCl_2$ in MeOH at r.t. to 40° C. overnight.

Preferred conditions for $R^1$=aryl and $R^3$=alkyl are heating the aniline and the ketone in MeOH at 80° C. overnight, followed by treatment with $NaBH_4$ in MeOH at 60° C. overnight.

Preferred conditions for $R^1$=heteroaryl and $R^3$=H are $NaBH(OAc)_3$ and HOAc in 1,2-dichloroethane at 60° C. overnight.

Step B: Alkylation of the compound of formula III-1 can by accomplished by treatment with a suitable (protected) aldehyde or ketone in the presence of a reducing agent such as $NaBH_4$, $LiBH_4$, $NaBH(OAc)_3$ or $Na(CN)BH_3$ in a solvent such as MeOH, EtOH, dichloromethane, 1,2-dichloroethane, THF, dioxane or mixtures thereof in the presence of an activating protic acid such as HCl or a carboxylic acid or an activating Lewis acid such as $ZnCl_2$ or $Ti(OiPr)_4$ at a temperature of −10 to 60° C. for 1-40 h.

Preferred conditions for introduction of a methyl group: the corresponding compound of formula III-1 is treated with 37% aqueous formaldehyde solution or paraformaldehyde in the presence of $NaBH_3CN$ and $ZnCl_2$ in MeOH at 40° C. for 2 hrs.

Preferred conditions for introduction of an ethyl group for $R^1$=aryl: the corresponding compound of formula III-1 is treated with acetaldehyde in the presence of $NaBH_3CN$ and $ZnCl_2$ in MeOH at 40° C. for 2 hrs.

Preferred conditions for introduction of an ethyl group for $R^1$=heteroaryl: the corresponding compound of formula III-1 is treated with acetaldehyde in the presence of $NaBH(OAc)_3$ and HOAc in 1,2-dichloroethane at r.t. overnight.

Preferred conditions for introduction of an isopropyl group: the corresponding compound of formula III-1 is treated with 2-methoxypropene in the presence of NaBH (OAc)$_3$ and trifluoro acetic acid in 1,2-dichloroethane overnight.

Preferred conditions for introduction of a benzyl, p-methoxy-benzyl, p-bromo-benzyl or p-chloro-benzyl group: the corresponding compound of formula III-1 is treated with benzaldehyde dimethyl acetal, p-methoxy-benzaldehyde dimethyl acetal, p-bromo-benzaldehyde dimethyl acetal or p-chloro-benzaldehyde dimethyl acetal in the presence of $NaBH(OAc)_3$ and trifluoroacetic acid in 1,2-dichloroethane overnight.

Step C: Preparation of an alkyl-substituted compound of formula III may alternatively be accomplished by reductive amination of a compound of formula V and Garner's aldehyde (from L- or D-serine; Garner, P.; Park, J. M. *Org. Synth.* 1998, IX, 300) in the presence of a reducing agent such as $NaBH_4$, $LiBH_4$, $NaBH(OAc)_3$ or $Na(CN)BH_3$ in a solvent such as MeOH, EtOH, dichloromethane, 1,2-dichloroethane, THF, dioxane or mixtures thereof in the presence of an activating protic acid such as HCl or a carboxylic acid or an activating Lewis acid such as $ZnCl_2$ or $Ti(OiPr)_4$ at a temperature of −10 to 60° C. for 1-40 h.

Preferred conditions are $NaBH_3CN$ and $ZnCl_2$ in MeOH at r.t. −40° C. overnight.

Scheme 2

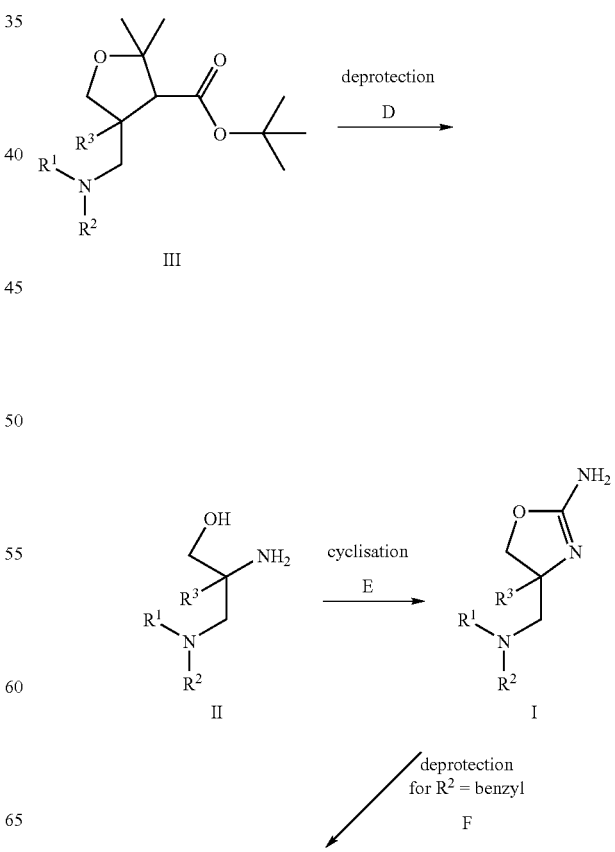

-continued

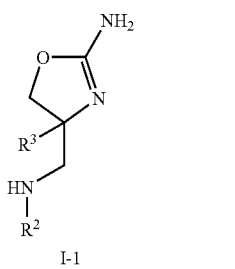

I-1

Step D: Simultaneous cleavage of the amino alcohol protecting groups can be effected with a mineral acid such as HCl, H$_2$SO$_4$ or H$_3$PO$_4$ or a organic acid such as CF$_3$COOH, CHCl$_2$COOH, HOAc or p-toluonesulfonic acid in a solvent such as CH$_2$Cl$_2$, CHCl$_3$, THF, MeOH, EtOH or H$_2$O at 0 to 60° C.

Preferred conditions are 2N HCl in EtOH at reflux for 1-3 hrs or 4N HCl in dioxane at r.t. overnight.

Step E: Cyclisation of the aminoalcohol to the corresponding 2-aminooxazoline of formula I can be accomplished by treatment with cyanogen bromide in THF as solvent and K$_2$CO$_3$ as base at r.t. overnight.

Step F: In cases where R$^2$ is the protecting group benzyl, deprotection can be accomplished by treatment with ammonium formate as reductant and palladium on activated charcoal as catalyst in methanol as solvent at elevated temperature (75° C.) overnight. In cases where R$^2$ is the protecting group p-methoxy-benzyl, deprotection can be accomplished by treatment with acids such as trifluoroacetic acid in the presence of a nucleophilic scavenging agent such as anisole in dichloromethane as solvent at r.t. overnight.

General Procedure 2

If R$^1$ is a heteroaryl substituent such as pyrimidinyl or pyridyl the intermediate III can also be produced as follows:

Scheme 3

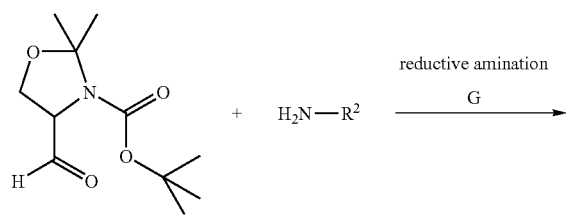

optically active
Garner's aldehyde
from L- or D-serine

IV      VI

-continued

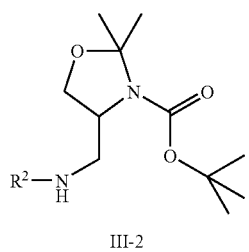

III-2 nucleophilic substitution
with R$^1$-X (if R$^1$ is heteroaryl)
H

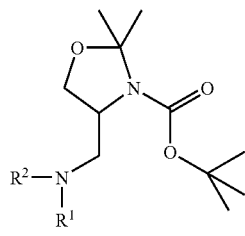

III

Step G: Reductive amination of optically active Garner's aldehyde (from L- or D-serine; Garner, P.; Park, J. M. Org. Synth. 1998, IX, 300) with a compound of formula VI can be accomplished by a reducing agent such as H$_2$ with a catalyst such as palladium, platinum, ruthenium or the like on a carrier such as charcoal or NaBH$_4$, LiBH$_4$, NaBH(OAc)$_3$, Na(CN)BH$_3$ in a solvent such as MeOH, EtOH, dichloromethane, 1,2-dichloroethane, THF, dioxane or mixtures thereof in the presence of molecular sieves or an activating protic acid such as HCl or a carboxylic acid or an activating Lewis acid such as ZnCl$_2$ or Ti(OiPr)$_4$ at a temperature of −10 to 60° C. for 1-40 h. Preferred conditions are Pd/C and H$_2$ in MeOH at r.t. overnight at atmospheric pressure.

Step H: Preparation of an heteroaryl-substituted compound of formula III can be accomplished by nucleophilic substitution of III-2 with an halogen substituted heterocycle such as 2-fluoropyridine, 4-fluoropyridine, 2-chloro-pyrimidine, 4-chloropyrimidine or further substituted analogs at elevated temperature in the range of 60-240° C. in an inert solvent such as ethanol, propanol or isopropanol. This substitution reaction can be achieved by conventional or microwave heating for several minutes to hours.

Preferred conditions are microwave heating in a closed vessel at 180° C. for 30 min in isopropanol.

Intermediate III is then further carried on to product I as described in General Procedure 1 Scheme 2.

General Procedure 3

Compounds of formula I can also be produced as follows:

Scheme 4

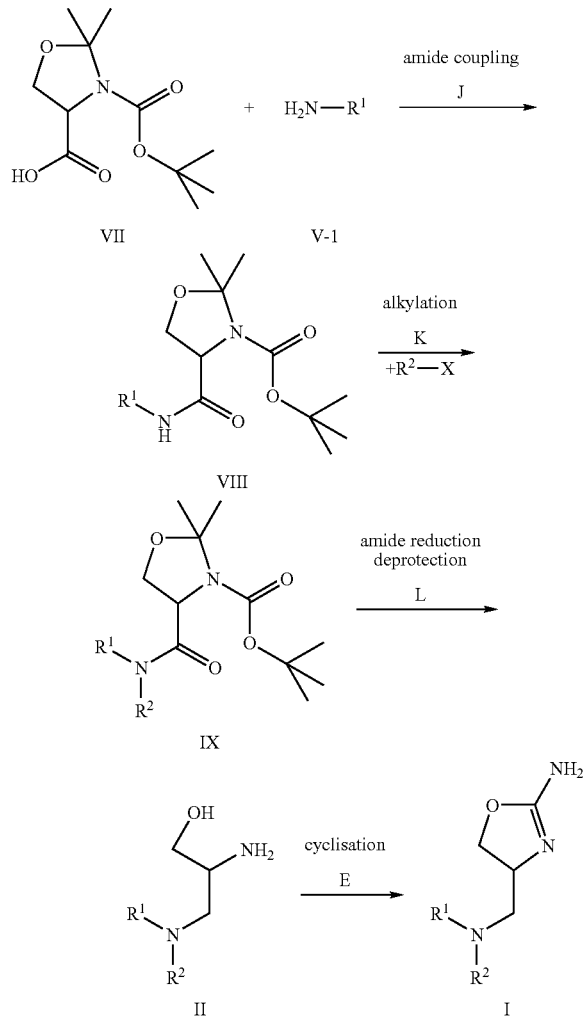

Step J: Amide coupling of chiral acid VII (the (S)-isomer available according to Chattopadhyay et al *Synthesis* 2006, 8, 1289; the (R)-isomer according to Micale et al in *J. Med. Chem.* 2006, 49, 3064) with a compound of formula V-1 can be accomplished by an amide coupling reagent such as bis(2-oxo-3-oxazolidinyl)phosphinic chloride (BOP—Cl), 2-(1h-benzotriazole-1-yl)-1,1,3,3-tetramethyluronium tetrafluoroborate (TBTU) or 2-(1h-benzotriazole-1-yl)-1,1,3,3-tetramethyluronium hexafluorophosphate (HBTU) or o-(7-azabenzotriazol-1-yl)-n,n,n',n'-tetramethyluronium hexafluorophosphate (HATU) and a base such as triethylamine or ethyldiisopropylamine in a solvent such as THF, DMF, or dichloromethane at a temperature of −10 to 60° C. for 1-40 h.

Preferred conditions are the use of bis(2-oxo-3-oxazolidinyl)phosphinic chloride and diisopropylethylamine in dichloromethane at r.t. overnight.

Step K: The alkylation of amide VIII can be accomplished using a base such as NaH, $Cs_2CO_3$, KOH, LiOH, NaOMe or NaOEt in a solvent such as acetone, DMF, DMSO, acetonitrile, toluene, EtOH or MeOH and optionally if appropriate a phase transfer catalyst such as tetrabutylammonium bromide or an additive such as a crown ether, tetrabutylammonium iodide or potassium iodide at r.t. −120° C. for 1-24 hrs.

Preferred conditions are sodium hydride in dimethylsulfoxide at room temperature overnight.

Step L: Reduction of the amide can be achieved by borane, borane-tetrahydrofurane complex, borane-dimethylsulfide complex or sodiumborohydride/bortrifluoride etherate in inert solvents such as tetrahydrofurane, dioxane or other ethers followed by acidic workup that leads in addition to simultaneous cleavage of the amino alcohol protecting groups. Acidic workup can be effected with a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are treatment with borane/THF for 2 hours at 60° C. followed by heating with 4N HCl for 2 hours at 60° C.

Step E: Cyclisation of the aminoalcohol to the corresponding 2-aminooxazoline of formula I can be accomplished by treatment with cyanogen bromide in THF as solvent and $K_2CO_3$ as base at r.t. overnight.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and can be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have a good affinity to the trace amine associated receptors (TAARs), especially TAAR1.

The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR1 were amplified from genomic DNA essentially as described by Lindemann et al. [14]. The Expand High Fidelity PCR System (Roche Diagnostics) was used with 1.5 mM $Mg^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Membrane Preparation and Radioligand Binding

Cells at confluence were rinsed with ice-cold phosphate buffered saline without $Ca^{2+}$ and $Mg^{2+}$ containing 10 mM EDTA and pelleted by centrifugation at 1000 rpm for 5 min at 4° C. The pellet was then washed twice with ice-cold phosphate buffered saline and cell pellet was frozen immediately by immersion in liquid nitrogen and stored until use at −80° C. Cell pellet was then suspended in 20 ml HEPES-NaOH (20 mM), pH 7.4 containing 10 mM EDTA, and homogenized with a Polytron (PT 3000, Kinematica) at 10,000 rpm for 10 s. The homogenate was centrifuged at 48,000×g for 30 min at 4° C. and the pellet resuspended in 20 ml HEPES-NaOH (20 mM), pH 7.4 containing 0.1 mM EDTA (buffer A), and homogenized with a Polytron at 10,000 rpm for 10 s. The homogenate was then centrifuged at 48,000×g for 30 min at 4° C. and the pellet resuspended in 20 ml buffer A, and homogenized with a Polytron at 10,000 rpm for 10 s. Protein concentration was determined by the method of Pierce (Rockford, Ill.). The homogenate was then centrifuged at 48,000×g for 10 min at 4° C., resuspended in HEPES-NaOH (20 mM), pH 7.0 including $MgCl_2$ (10 mM) and $CaCl_2$ g protein per ml and (2 mM) (buffer B) at 200 homogenized with a Polytron at 10,000 rpm for 10 s.

Binding assay was performed at 4° C. in a final volume of 1 ml, and with an incubation time of 30 min. The radioligand [$^3$H]-rac-2-(1,2,3,4-tetrahydro-1-naphthyl)-2-imidazoline was used at a concentration equal to the calculated $K_d$ value of 60 nM to give a bound at around 0.1% of the total added radioligand concentration, and a specific binding which represented approximately 70-80% of the total binding. Non-specific binding was defined as the amount of [$^3$H]-rac-2-(1,2,3,4-tetrahydro-1-naphthyl)-2-imidazoline bound in the presence of the appropriate unlabelled ligand (10 μM). Competing ligands were tested in a wide range of concentrations (10 pM-30 μM). The final dimethylsulphoxide concentration in the assay was 2%, and it did not affect radioligand binding. Each experiment was performed in duplicate. All incubations were terminated by rapid filtration through UniFilter-96 plates (Packard Instrument Company) and glass filter GF/C, pre-soaked for at least 2 h in polyethylenimine 0.3%, and using a Filtermate 96 Cell Harvester (Packard Instrument Company). The tubes and filters were then washed 3 times with 1 ml aliquots of cold buffer B. Filters were not dried and soaked in Ultima gold (45 μl/well, Packard Instrument Company) and bound radioactivity was counted by a TopCount Microplate Scintillation Counter (Packard Instrument Company).

The preferred compounds show a Ki value (μM) in mouse and/or rat on TAAR1 in the range of lower than 0.01 μM. Values for representative compounds are shown in the table below.

| Example | Ki (μM) mouse/rat |
|---|---|
| 1 | 0.0009/0.0019 |
| 3 | 0.001/0.001 |
| 7 | 0.0014/0.0003 |
| 11 | 0.0035/0.0009 |
| 15 | 0.0224/0.0008 |
| 27 | 0.0073/0.0016 |
| 28 | 0.0023/0.0006 |
| 30 | 0.0163/0.0017 |
| 31 | 0.0013/0.0019 |
| 32 | 0.0028/0.0006 |
| 33 | 0.0022/0.0002 |
| 34 | 0.0012/0.0047 |
| 37 | 0.0097/0.0018 |
| 40 | 0.0011/0.002 |
| 42 | 0.0264/0.0011 |
| 53 | 0.0187/0.0009 |
| 55 | 0.0288/0.0006 |
| 65 | 0.0019/0.0027 |
| 77 | 0.0004/— |
| 83 | —/0.001 |
| 87 | —/0.0073 |
| 92 | —/0037 |
| 94 | —/0051 |
| 95 | —/0.0015 |
| 99 | 0.006/0.0032 |
| 100 | 0.0027/0.003 |
| 105 | 0.0038/0.0635 |
| 106 | 0.0041/0.0188 |
| 107 | 0.0039/0.0149 |
| 109 | 0.0025/0.0017 |
| 111 | 0.006/0.0587 |
| 113 | 0.0028/0.0062 |
| 117 | 0.0028/0.0182 |
| 119 | 0.0011/0.0042 |
| 125 | 0.0023/0.0056 |
| 126 | 0.0016/0.0012 |
| 127 | 0.0046/0.0157 |
| 128 | 0.0047/0.0116 |
| 129 | 0.0088/0.0027 |
| 132 | 0.0047/0.0248 |
| 133 | 0.0042/0.0049 |
| 134 | 0.0057/0.0036 |
| 135 | 0.0087/0.0489 |
| 138 | 0.0044/0.0093 |
| 139 | 0.0041/0.0016 |
| 140 | 0.0026/0.0041 |
| 141 | 0.0034/0.0009 |
| 145 | 0.0082/0.0048 |
| 146 | 0.0031/0.0062 |
| 152 | 0.0032/0.0072 |
| 157 | 0.0017/0.0021 |
| 158 | 0.0022/0.0004 |
| 159 | 0.0053/0.0014 |
| 160 | 0.0013/0.0009 |

-continued

| Example | Ki (μM) mouse/rat |
|---|---|
| 162 | 0.0077/0.0155 |
| 163 | 0.0029/0.0052 |
| 165 | 0.0014/0.0009 |
| 167 | 0.0051/0.0097 |
| 175 | 0.0092/0.0083 |

The present invention also provides pharmaceutical compositions containing compounds of the invention, for example compounds of formula (I) and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include disorders of the central nervous system, for example the treatment or prevention of depression, psychosis, Parkinson's disease, anxiety and attention deficit hyperactivity disorder (ADHD).

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Macrocrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXPERIMENTAL

The following examples illustrate the invention but are not intended to limit its scope.

Example 1

(R)-4-[(Ethyl-phenyl-amino)-methyl]-4,5-dihydro-oxazol-2-ylamine a) (R)-2,2-Dimethyl-4-phenylaminomethyl-oxazolidine-3-carboxylic acid tert-butyl ester

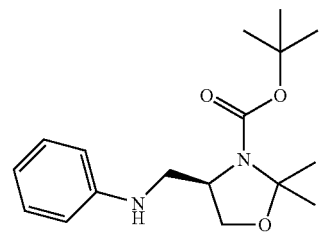

To a stirred solution of tert-butyl (S)-(−)-4-formyl-2,2-dimethyl-3-oxazolinecarboxylate (2.07 g) at r.t. in methanol (25 ml) under an argon atmosphere were added aniline (763 mg), ZnCl$_2$ (4.47 g) and NaBH$_3$CN (1.55 g). The mixture was stirred at 40° C. for 16 h, then cooled to r.t. and concentrated to leave a yellow paste. This was taken up in EtOAc and H$_2$O. The aqueous phase was back extracted with EtOAc. The combined organics were washed with brine, dried over MgSO$_4$, filtered and concentrated. The crude product was purified by column chromatography (SiO$_2$; gradient:cyclohexane->cyclohexane/EtOAc 4:1) to give (R)-2,2-dimethyl-4-phenylaminomethyl-oxazolidine-3-carboxylic acid tert-butyl ester (2.21 g, 88%) as off-white solid. MS (ISP): 307.4 ([M+H]$^+$)

b) (R)-4-[(Ethyl-phenyl-amino)-methyl]-2,2-dimethyl-oxazolidine-3-carboxylic acid tert-butyl ester

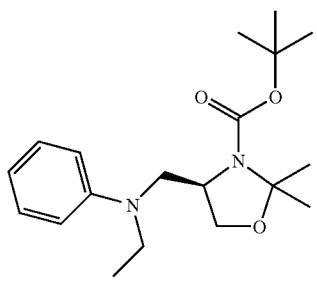

To a stirred solution of (R)-2,2-dimethyl-4-phenylaminomethyl-oxazolidine-3-carboxylic acid tert-butyl ester (730 mg) at r.t. in methanol (20 ml) under an argon atmosphere were added acetaldehyde (0.67 ml), ZnCl$_2$ (1.30 g) and NaBH$_3$CN (0.45 g). The mixture was warmed to 40° C. and stirring at that temperature was continued for 17 h. The mixture was cooled to r.t., directly adsorbed on silica gel and purified by column chromatography (SiO$_2$; gradient:cyclohexane->cyclohexane/EtOAc 4:1) to give (R)-4-[(ethyl-phenyl-amino)-methyl]-2,2-dimethyl-oxazolidine-3-carboxylic acid tert-butyl ester (614 mg, 77%) as colorless viscous oil. MS (ISP): 335.5 ([M+H]$^+$)

c) (R)-2-Amino-3-(ethyl-phenyl-amino)-propan-1-ol

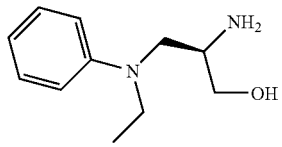

To a stirred solution of (R)-4-[(ethyl-phenyl-amino)-methyl]-2,2-dimethyl-oxazolidine-3-carboxylic acid tert-butyl ester (608 mg) at r.t. in dioxane (5.5 ml) under an argon atmosphere was added HCl solution (4 M in dioxane; 4.54 ml). The mixture was stirred at r.t. overnight and concentrated. The residue was taken up in EtOAc and washed with 1N NaOH. The aqueous layer was back extracted with EtOAc. The combined organics were washed with brine, dried over MgSO$_4$ and concentrated. The crude product was purified by column chromatography (Isolute® SPE flash NH2 column, aminopropyl-functionalized silica; CH$_2$Cl$_2$/MeOH 9:1) to give (R)-2-amino-3-(ethyl-phenyl-amino)-propan-1-ol (297 mg, 84%) as off-white amorphous solid. MS (ISP): 195.3 ([M+H]$^+$)

d) ((R)-4-[(Ethyl-phenyl-amino)-methyl]-4,5-dihydro-oxazol-2-ylamine

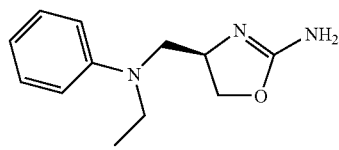

To a stirred solution of (R)-2-amino-3-(ethyl-phenyl-amino)-propan-1-ol (235 mg) at r.t. in THF (10 ml) under an argon atmosphere were added potassium carbonate (334 mg) and a solution of cyanogen bromide (256 mg) in THF (5 ml). Stirring at r.t. was continued for 18 h. The mixture (off-white suspension) was diluted with EtOAc and washed with H$_2$O. The aqueous phase was back extracted with EtOAc. The combined organics were washed with brine, dried over MgSO$_4$, filtered and concentrated. The crude product was purified by column chromatography (Isolute® SPE flash NH2 column, aminopropyl-functionalized silica; gradient: CH$_2$Cl$_2$->CH$_2$Cl$_2$/MeOH 9:1) to provide (R)-4-[(ethyl-phenyl-amino)-methyl]-4,5-dihydro-oxazol-2-ylamine (142 mg, 54%) as off-white solid. MS (ISP): 220.1 ([M+H]$^+$)

Example 2

(S)-4-[(Isopropyl-phenyl-amino)-methyl]-4,5-dihydro-oxazol-2-ylamine a) (S)-2,2-Dimethyl-4-phenylaminomethyl-oxazolidine-3-carboxylic acid tert-butyl ester

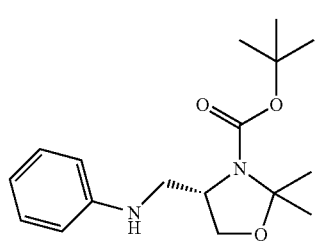

In analogy to example 1.a tert-butyl (R)-(+)-4-formyl-2,2-dimethyl-3-oxazolinecarboxylate was reacted with aniline to give (S)-2,2-dimethyl-4-phenylaminomethyl-oxazolidine-3-carboxylic acid tert-butyl ester. Light yellow solid. MS (ISP): 307.3 ([M+H]$^+$)

b) (S)-4-[(Isopropyl-phenyl-amino)-methyl]-2,2-dimethyl-oxazolidine-3-carboxylic acid tert-butyl ester

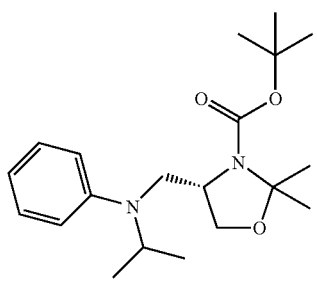

To a stirred solution of (S)-2,2-dimethyl-4-phenylaminomethyl-oxazolidine-3-carboxylic acid tert-butyl ester (650 mg) at r.t. in 1,2-dichloroethane (15 ml) under an argon atmosphere were added 2-methoxypropene (0.30 ml), trifluoroacetic acid (0.16 ml) and sodium triacetoxyborohydride (674 mg). The mixture was heated to 40° C. overnight. The mixture was cooled to r.t., directly adsorbed on silica gel and purified by chromatography (SiO$_2$; gradient:cyclohexane->cyclohexane/EtOAc 7:3) to give (S)-4-[(isopropyl-phenyl-amino)-methyl]-2,2-dimethyl-oxazolidine-3-carboxylic acid tert-butyl ester (659 mg, 89%) as light yellow viscous oil. MS (ISP): 349.5 ([M+H]$^+$)

c) ((S)-2-Amino-3-(isopropyl-phenyl-amino)-propan-1-ol dihydrochloride

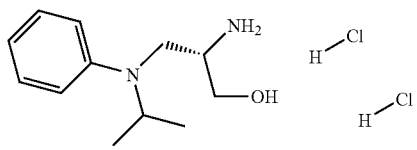

To a stirred solution of (S)-4-[(isopropyl-phenyl-amino)-methyl]-2,2-dimethyl-oxazolidine-3-carboxylic acid tert-butyl ester (650 mg) in dioxane (5 ml) under an argon atmosphere was added HCl solution (4M in dioxane; 9.33 ml). The mixture was stirred overnight. The mixture was concentrated and the residue was dried to give (S)-2-amino-3-(isopropyl-phenyl-amino)-propan-1-ol dihydrochloride (616 mg, quant.) as off-white amorphous solid. MS (ISP): 209.3 ([M+H]$^+$)

d) (S)-4-[(Isopropyl-phenyl-amino)-methyl]-4,5-dihydro-oxazol-2-ylamine

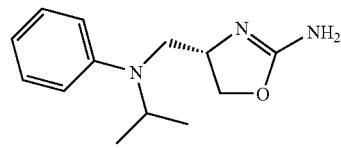

In analogy to example 1.d (S)-2-amino-3-(isopropyl-phenyl-amino)-propan-1-ol dihydrochloride was reacted with cyanogen bromide to give (S)-4-[(isopropyl-phenyl-amino)-methyl]-4,5-dihydro-oxazol-2-ylamine as light yellow amorphous solid. MS (ISP): 234.3 ([M+H]$^+$)

Example 3

(S)-4-[(Ethyl-phenyl-amino)-methyl]-4,5-dihydro-oxazol-2-ylamine a) (S)-4-[(Ethyl-phenyl-amino)-methyl]-2,2-dimethyl-oxazolidine-3-carboxylic acid tert-butyl ester

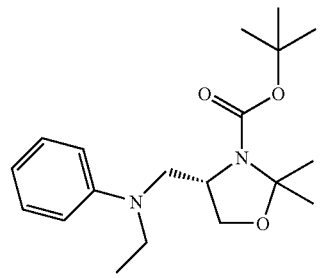

To a stirred solution of tert-butyl (R)-(+)-4-formyl-2,2-dimethyl-3-oxazolinecarboxylate (681 mg) at r.t. in 1,2-dichloroethane (10 ml) under an argon atmosphere were added molecular sieves 4 Å (1.5 g) and N-ethylaniline (0.25 ml). After stirring for 15 min at r.t., sodium triacetoxyborohydride (1.68 g) was added in one portion, followed by acetic acid (5 drops) and stirring at r.t. was continued overnight. The mixture was quenched by the careful addition of 10% KHCO$_3$ (15 ml). The biphasic mixture was stirred at r.t. for 20 min and filtered. The aqueous phase of the filtrate was back extracted with CH$_2$Cl$_2$. The combined organics were washed with H$_2$O and brine, dried over MgSO$_4$, filtered and concentrated. The crude product was purified by column chromatography (SiO$_2$; gradient:cyclohexane->cyclohexane/EtOAc 4:1) to give (S)-4-[(ethyl-phenyl-amino)-methyl]-2,2-dimethyl-oxazolidine-3-carboxylic acid tert-butyl ester (469 mg, 57%) as orange viscous oil. MS (ISP): 335.5 ([M+H]⁺)

b) (S)-2-Amino-3-(ethyl-phenyl-amino)-propan-1-ol

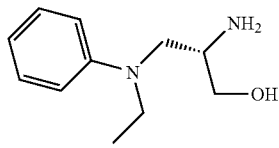

In analogy to example 1.c (S)-4-[(ethyl-phenyl-amino)-methyl]-2,2-dimethyl-oxazolidine-3-carboxylic acid tert-butyl ester was converted to (S)-2-amino-3-(ethyl-phenyl-amino)-propan-1-ol. Light brown viscous oil. MS (ISP): 195.1 ([M+H]⁺)

c) (S)-4-[(Ethyl-phenyl-amino)-methyl]-4,5-dihydro-oxazol-2-ylamine

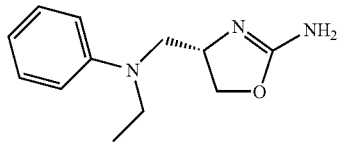

In analogy to example 1.d (S)-2-amino-3-(ethyl-phenyl-amino)-propan-1-ol was reacted with cyanogen bromide to give (S)-4-[(ethyl-phenyl-amino)-methyl]-4,5-dihydro-oxazol-2-ylamine. Off-white solid. MS (ISP): 220.4 ([M+H]⁺)

Example 4

(R)-4-[(Isopropyl-phenyl-amino)-methyl]-4,5-dihydro-oxazol-2-ylamine

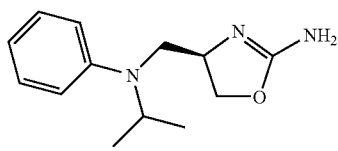

The title compound was prepared in analogy to example 2 starting from tert-butyl (S)-(−)-4-formyl-2,2-dimethyl-3-oxazolinecarboxylate and aniline. MS (ISP): 234.3 ([M+H]⁺)

Example 5

(S)-4-{[(4-Benzyl-phenyl)-ethyl-amino]-methyl}-4,5-dihydro-oxazol-2-ylamine a) (S)-2-Amino-3-[(4-benzyl-phenyl)-ethyl-amino]-propan-1-ol

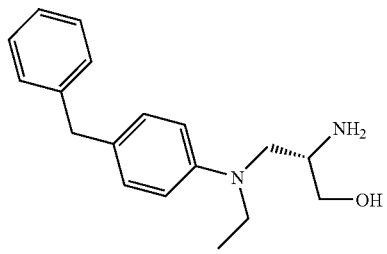

To a stirred solution of (S)-4-{[(4-benzyl-phenyl)-ethyl-amino]-methyl}-2,2-dimethyl-oxazolidine-3-carboxylic acid tert-butyl ester (405 mg; prepared in analogy to example 1.a and 1.b starting from tert-butyl (R)-(+)-4-formyl-2,2-dimethyl-3-oxazolinecarboxylate and 4-benzylaniline) at r.t. in dioxane (5 ml) under an argon atmosphere was added HCl solution (4M in dioxane; 4.77 ml). The mixture was stirred overnight 16 h, then concentrated. The residue was taken up in CH₂Cl₂/MeOH 95:5 and 1N NaOH. The aqueous phase was back extracted with CH₂Cl₂/MeOH 95:5. The combined organics were washed with brine, dried over MgSO₄, filtered and concentrated. The crude product was purified by column chromatography (Isolute® SPE flash NH₂ column, aminopropyl-functionalized silica; gradient:CH₂Cl₂->CH₂Cl₂/MeOH 9:1) to give (S)-2-amino-3-[(4-benzyl-phenyl)-isopropyl-amino]-propan-1-ol (192 mg, 71%) as colorless amorphous solid. MS (ISP): 285.3 ([M+H]⁺)

b) (S)-4-{[(4-Benzyl-phenyl)-ethyl-amino]-methyl}-4,5-dihydro-oxazol-2-ylamine

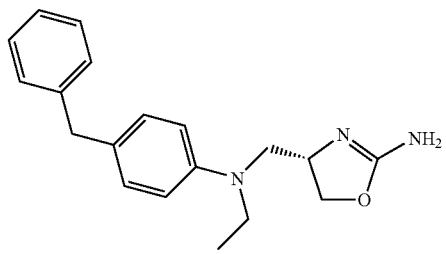

In analogy to example 1.d (S)-2-amino-3-[(4-benzyl-phenyl)-isopropyl-amino]-propan-1-ol was reacted with cyanogen bromide to give S)-4-{[(4-benzyl-phenyl)-ethyl-amino]-methyl}-4,5-dihydro-oxazol-2-ylamine. Colorless gum. MS (ISP): 310.4 ([M+H]$^+$)

Example 6

(S)-4-{[(4-Benzyl-phenyl)-isopropyl-amino]-methyl}-4,5-dihydro-oxazol-2-ylamine a) (S)-2-Amino-3-[(4-benzyl-phenyl)-isopropyl-amino]-propan-1-ol

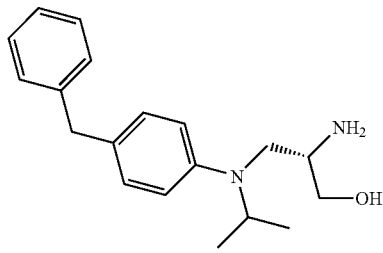

In analogy to example 5.a (S)-4-{[(4-benzyl-phenyl)-isopropyl-amino]-methyl}-2,2-dimethyl-oxazolidine-3-carboxylic acid tert-butyl ester (prepared in analogy to example 2.a and 2.b starting from tert-butyl (R)-(+)-4-formyl-2,2-dimethyl-3-oxazolinecarboxylate and 4-benzylaniline) was converted to (S)-2-amino-3-[(4-benzyl-phenyl)-isopropyl-amino]-propan-1-ol. Colorless amorphous solid. MS (ISP): 299.5 ([M+H]$^+$)

b) (S)-4-{[(4-Benzyl-phenyl)-isopropyl-amino]-methyl}-4,5-dihydro-oxazol-2-ylamine

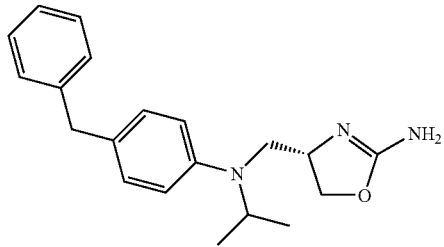

In analogy to example 1.d (S)-2-amino-3-[(4-benzyl-phenyl)-isopropyl-amino]-propan-1-ol was reacted with cyanogen bromide to give (S)-4-{[(4-benzyl-phenyl)-isopropyl-amino]-methyl}-4,5-dihydro-oxazol-2-ylamine. Light yellow gum. MS (ISP): 324.4 ([M+H]$^+$)

Example 7

(S)-4-{[(3,4-Dichloro-phenyl)-methyl-amino]-methyl}-4,5-dihydro-oxazol-2-ylamine

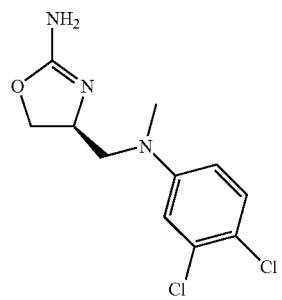

In analogy to example 30 the title compound was prepared starting from tert-butyl (R)-(+)-4-formyl-2,2-dimethyl-3-oxazolinecarboxylate and 3,4-dichloroaniline. White solid. MS (ISP): 278.2 ([{$^{37}$Cl$^{37}$Cl}M+H]$^+$), 276.1 ([{$^{37}$Cl$^{35}$Cl}M+H]$^+$), 274.2 ([{$^{35}$Cl$^{35}$Cl}M+H]$^+$)

Example 8

(S)-4-[(Biphenyl-4-yl-ethyl-amino)-methyl]-4,5-dihydro-oxazol-2-ylamine

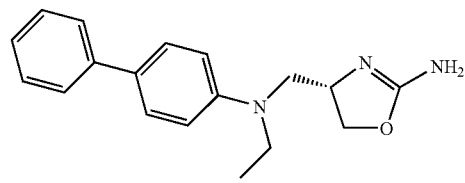

In analogy to example 1 the title compound was prepared starting from tert-butyl (R)-(+)-4-formyl-2,2-dimethyl-3-oxazolinecarboxylate and 4-aminobiphenyl. White solid. MS (ISP): 296.1 ([M+H]$^+$)

Example 9

(S)-4-{[(4-Chloro-phenyl)-methyl-amino]-methyl}-4,5-dihydro-oxazol-2-ylamine

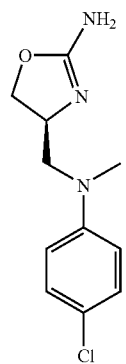

In analogy to example 30 the title compound was prepared starting from tert-butyl (R)-(+)-4-formyl-2,2-dimethyl-3-oxazolinecarboxylate and 4-chloroaniline. White solid. MS (ISP): 242.2 ([{$^{37}$Cl}M+H]$^+$), 240.2 ([{$^{35}$Cl}M+H]$^+$)

Example 10

(S)-4-{[(3-Benzyloxy-phenyl)-ethyl-amino]-methyl}-4,5-dihydro-oxazol-2-ylamine

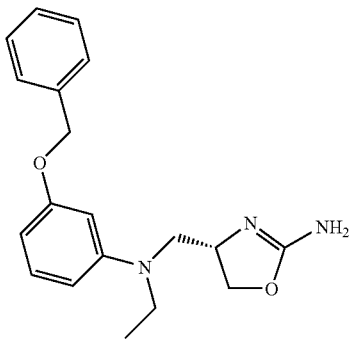

In analogy to example 1 the title compound was prepared starting from tert-butyl (R)-(+)-4-formyl-2,2-dimethyl-3-oxazolinecarboxylate and 3-benzyloxyaniline. Amorphous colorless solid. MS (ISP): 326.3 ([M+H]$^+$)

Example 11

(S)-4-{[(4-Chloro-phenyl)-ethyl-amino]-methyl}-4,5-dihydro-oxazol-2-ylamine

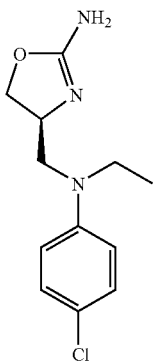

In analogy to example 1 the title compound was prepared starting from tert-butyl (R)-(+)-4-formyl-2,2-dimethyl-3-oxazolinecarboxylate and 4-chloroaniline. Light yellow gum. MS (ISP): 256.3 ([{$^{37}$Cl}M+H]$^+$), 254.2 ([{$^{35}$Cl}M+H]$^+$)

Example 12

(S)-4-{[(4-Chloro-phenyl)-isopropyl-amino]-methyl}-4,5-dihydro-oxazol-2-ylamine

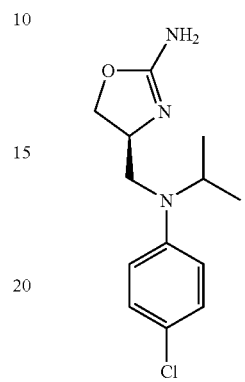

The title compound was prepared in analogy to example 2 starting from tert-butyl (R)-(+)-4-formyl-2,2-dimethyl-3-oxazolinecarboxylate and 4-chloroaniline. Colourless gum. MS (ISP): 270.3 ([{$^{37}$Cl}M+H]$^+$), 268.3 ([{$^{35}$Cl}M+H]$^+$)

Example 13

(S)-4-(2,3-Dihydro-indol-1-ylmethyl)-4,5-dihydro-oxazol-2-ylamine

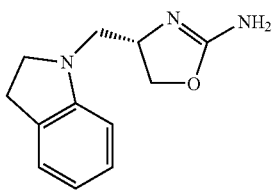

In analogy to example 3 the title compound was prepared starting from tert-butyl (R)-(+)-4-formyl-2,2-dimethyl-3-oxazolinecarboxylate and indoline. White solid. MS (ISP): 218.4 ([M+H]$^+$)

Example 14

(S)-4-[(Biphenyl-3-yl-ethyl-amino)-methyl]-4,5-dihydro-oxazol-2-ylamine

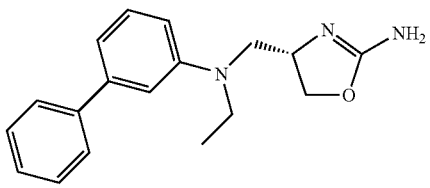

In analogy to example 1 the title compound was prepared starting from tert-butyl (R)-(+)-4-formyl-2,2-dimethyl-3-oxazolinecarboxylate and 3-aminobiphenyl. Colorless amorphous solid. MS (ISP): 296.5 ([M+H]$^+$)

Example 15

(S)-4-{[(3,4-Dichloro-phenyl)-isopropyl-amino]-methyl}-4,5-dihydro-oxazol-2-ylamine

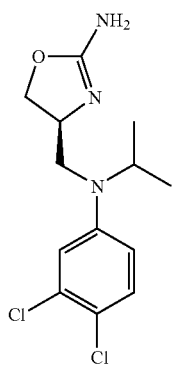

The title compound was prepared in analogy to example 2 starting from tert-butyl (R)-(+)-4-formyl-2,2-dimethyl-3-oxazolinecarboxylate and 3,4-dichloroaniline. Colourless gum. MS (ISP): 306.2 ([{$^{37}$Cl$^{37}$Cl}M+H]$^+$), 304.1 ([{$^{37}$Cl$^{35}$Cl}M+H]$^+$), 302.2 ([{$^{35}$Cl$^{35}$Cl}M+H]$^+$)

Example 16

(S)-4-{[(4-Fluoro-phenyl)-methyl-amino]-methyl}-4,5-dihydro-oxazol-2-ylamine

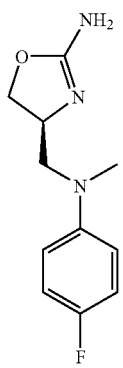

In analogy to example 30 the title compound was prepared starting from tert-butyl (R)-(+)-4-formyl-2,2-dimethyl-3-oxazolinecarboxylate and 4-fluoroaniline. Light yellow gum. MS (ISP): 224.4 ([M+H]$^+$)

Example 17

(S)-4-{[Ethyl-(4-fluoro-phenyl)-amino]-methyl}-4,5-dihydro-oxazol-2-ylamine

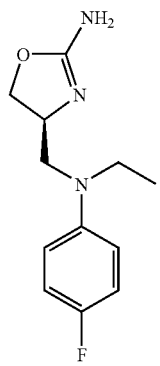

In analogy to example 1 the title compound was prepared starting from tert-butyl (R)-(+)-4-formyl-2,2-dimethyl-3-oxazolinecarboxylate and 4-fluoroaniline. Light yellow gum. MS (ISP): 238.3 ([M+H]$^+$)

Example 18

(S)-4-{[(4-Fluoro-phenyl)-isopropyl-amino]-methyl}-4,5-dihydro-oxazol-2-ylamine

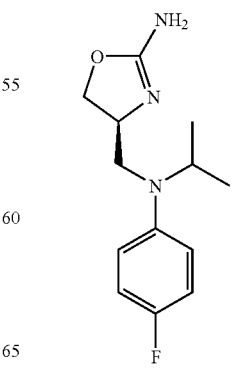

The title compound was prepared in analogy to example 2 starting from tert-butyl (R)-(+)-4-formyl-2,2-dimethyl-3-oxazolinecarboxylate and 4-fluoroaniline. Light yellow gum. MS (ISP): 252.1 ([M+H]$^+$)

Example 19

(S)-4-{[Ethyl-(3-phenoxy-phenyl)-amino]-methyl}-4,5-dihydro-oxazol-2-ylamine

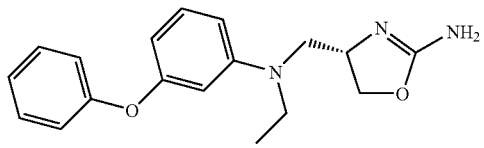

In analogy to example 1 the title compound was prepared starting from tert-butyl (R)-(+)-4-formyl-2,2-dimethyl-3-oxazolinecarboxylate and 3-phenoxyaniline. Amorphous yellow solid. MS (ISP): 312.3 ([M+H]$^+$)

Example 20

(S)-4-[(Benzyl-phenyl-amino)-methyl]-4,5-dihydro-oxazol-2-ylamine a) (S)-4-[(Benzyl-phenyl-amino)-methyl]-2,2-dimethyl-oxazolidine-3-carboxylic acid tert-butyl ester

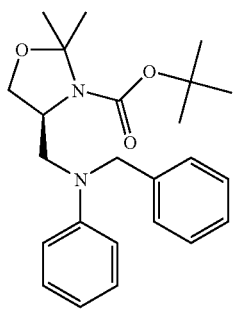

To a stirred solution of (S)-2,2-dimethyl-4-phenylaminomethyl-oxazolidine-3-carboxylic acid tert-butyl ester (495 mg; example 2.a) at r.t. in 1,2-dichloroethane (10 ml) under an argon atmosphere were added benzaldehyde dimethyl acetal (0.37 ml), trifluoroacetic acid (0.13 ml) and sodium triacetoxyborohydride (571 mg). The mixture was stirred at room temperature overnight. The mixture was directly adsorbed on silica gel and purified by chromatography (SiO$_2$; gradient: heptane->heptane/EtOAc 7:3) to give (S)-4-[(benzyl-phenyl-amino)-methyl]-2,2-dimethyl-oxazolidine-3-carboxylic acid tert-butyl ester (492 mg, 77%) as a colourless viscous oil. MS (ISP): 397.4 ([M+H]$^+$)

b) (S)-4-[(Benzyl-phenyl-amino)-methyl]-4,5-dihydro-oxazol-2-ylamine

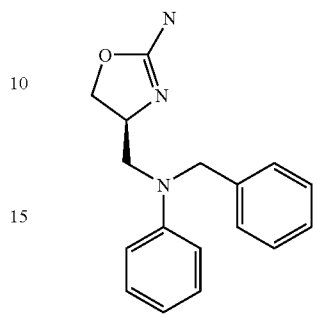

In analogy to example 1.c and 1.d (S)-4-[(benzyl-phenyl-amino)-methyl]-2,2-dimethyl-oxazolidine-3-carboxylic acid tert-butyl ester was converted to (S)-4-[(benzyl-phenyl-amino)-methyl]-4,5-dihydro-oxazol-2-ylamine. Colorless gum. MS (ISP): 282.1 ([M+H]$^+$)

Example 21

(S)-4-{[(3-Fluoro-phenyl)-methyl-amino]-methyl}-4,5-dihydro-oxazol-2-ylamine

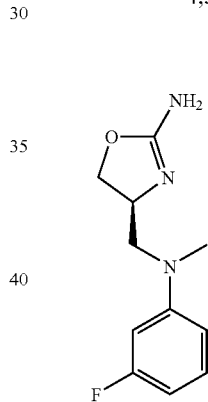

In analogy to example 30 the title compound was prepared starting from tert-butyl (R)-(+)-4-formyl-2,2-dimethyl-3-oxazolinecarboxylate and 3-fluoroaniline. Light yellow gum. MS (ISP): 224.1 ([M+H]$^+$)

Example 22

(R)-4-(2,3-Dihydro-indol-1-ylmethyl)-4,5-dihydro-oxazol-2-ylamine

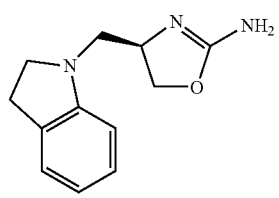

In analogy to example 3 the title compound was prepared starting from tert-butyl (S)-(−)-4-formyl-2,2-dimethyl-3-oxazolinecarboxylate and indoline. Off-white solid. MS (ISP): 218.4 ([M+H]$^+$)

Example 23

(R)-4-(3,4-Dihydro-2H-quinolin-1-ylmethyl)-4,5-dihydro-oxazol-2-ylamine

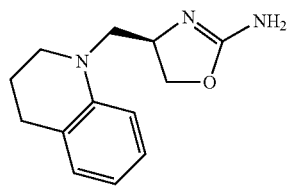

In analogy to example 3 the title compound was prepared starting from tert-butyl (S)-(−)-4-formyl-2,2-dimethyl-3-oxazolinecarboxylate and 1,2,3,4-tetrahydro-quinoline. Off-white solid. MS (ISP): 232.1 ([M+H]$^+$)

Example 24

(S)-4-{[(3-Fluoro-phenyl)-isopropyl-amino]-methyl}-4,5-dihydro-oxazol-2-ylamine

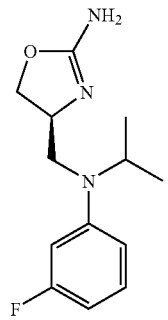

The title compound was prepared in analogy to example 2 starting from tert-butyl (R)-(+)-4-formyl-2,2-dimethyl-3-oxazolinecarboxylate and 3-fluoroaniline. Light yellow gum. MS (ISP): 252.4 ([M+H]$^+$)

Example 25

(S)-4-{[Ethyl-(3-fluoro-phenyl)-amino]-methyl}-4,5-dihydro-oxazol-2-ylamine

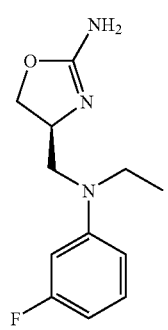

In analogy to example 1 the title compound was prepared starting from tert-butyl (R)-(+)-4-formyl-2,2-dimethyl-3-oxazolinecarboxylate and 3-fluoroaniline. Light yellow gum. MS (ISP): 238.1 ([M+H]$^+$)

Example 26

(S)-4-(3,4-Dihydro-2H-quinolin-1-ylmethyl)-4,5-dihydro-oxazol-2-ylamine

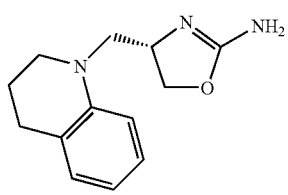

In analogy to example 3 the title compound was prepared starting from tert-butyl (R)-(+)-4-formyl-2,2-dimethyl-3-oxazolinecarboxylate and 1,2,3,4-tetrahydro-quinoline. Off-white solid. MS (ISP): 232.1 ([M+H]$^+$)

Example 27

(S)-4-{[(4-Chloro-3-methoxy-phenyl)-methyl-amino]-methyl}-4,5-dihydro-oxazol-2-ylamine

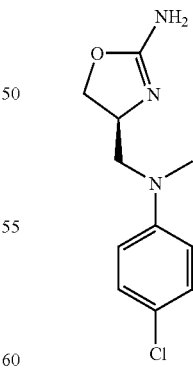

In analogy to example 30 the title compound was prepared starting from tert-butyl (R)-(+)-4-formyl-2,2-dimethyl-3-oxazolinecarboxylate and 4-chloro-3-methoxyaniline. White solid. MS (ISP): 272.3 ([{$^{37}$Cl}M+H]$^+$), 270.3 ([{$^{35}$Cl}M+H]$^+$)

Example 28

(S)-4-{[(4-Chloro-3-methoxy-phenyl)-ethyl-amino]-methyl}-4,5-dihydro-oxazol-2-ylamine

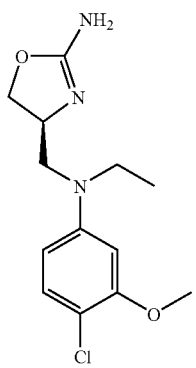

In analogy to example 1 the title compound was prepared starting from tert-butyl (R)-(+)-4-formyl-2,2-dimethyl-3-oxazolinecarboxylate and 4-chloro-3-methoxyaniline. Colourless viscous oil. MS (ISP): 286.2 ([{$^{37}$Cl}M+H]$^+$), 284.3 ([{$^{35}$Cl}M+H]$^+$)

Example 29

(S)-4-{[(4-Chloro-3-methoxy-phenyl)-isopropyl-amino]-methyl}-4,5-dihydro-oxazol-2-ylamine

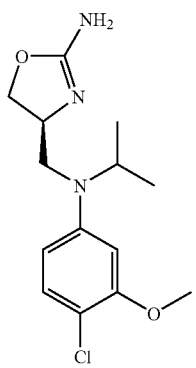

The title compound was prepared in analogy to example 2 starting from tert-butyl (R)-(+)-4-formyl-2,2-dimethyl-3-oxazolinecarboxylate and 4-chloro-3-methoxyaniline. Off-white gum. MS (ISP): MS (ISP): 300.2 ([{$^{37}$Cl}M+H]$^+$), 298.3 ([{$^{35}$Cl}M+H]$^+$)

Example 30

(S)-4-[(Methyl-phenyl-amino)-methyl]-4,5-dihydro-oxazol-2-ylamine a) (S)-2,2-Dimethyl-4-[(methyl-phenyl-amino)-methyl]-oxazolidine-3-carboxylic acid tert-butyl ester

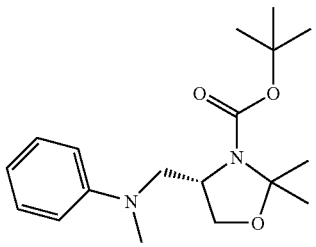

To a stirred solution of (S)-2,2-dimethyl-4-phenylaminomethyl-oxazolidine-3-carboxylic acid tert-butyl ester (500 mg; example 2.a) at r.t. in methanol (10 ml) under an argon atmosphere were added formaldehyde (37% solution in H$_2$O; 0.62 ml), zinc chloride (890 mg) and NaBH$_3$CN (308 mg). The mixture was heated to 40° C. and stirring at that temperature was continued for 2 h. The mixture was concentrated and the residue was taken up in EtOAc/H$_2$O. The biphasic mixture was filtered. The aqueous layer from the filtrate was back extracted with EtOAc. The combined organics were washed with brine, dried over MgSO$_4$, filtered and concentrated. The crude product was purified by column chromatography (silica gel; gradient:cyclohexane->cyclohexane/EtOAc 85:15) to give (S)-2,2-dimethyl-4-[(methyl-phenyl-amino)-methyl]-oxazolidine-3-carboxylic acid tert-butyl ester (462 mg, 88%) as colorless viscous oil. MS (ISP): 321.4 ([M+H]$^+$)

b) (S)-4-[(Methyl-phenyl-amino)-methyl]-4,5-dihydro-oxazol-2-ylamine

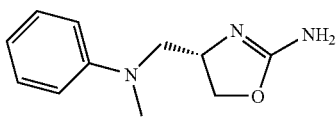

In analogy to example 1.c and 1.d (S)-2,2-dimethyl-4-[(methyl-phenyl-amino)-methyl]-oxazolidine-3-carboxylic acid tert-butyl ester was converted to (S)-4-[(methyl-phenylamino)-methyl]-4,5-dihydro-oxazol-2-ylamine. Colorless gum. MS (ISP): 206.1 ([M+H]+)

Example 31

(S)-4-{[(4-Bromo-phenyl)-methyl-amino]-methyl}-4,5-dihydro-oxazol-2-ylamine

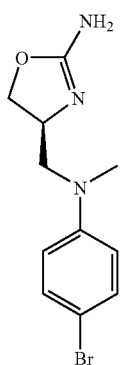

In analogy to example 30 the title compound was prepared starting from tert-butyl (R)-(+)-4-formyl-2,2-dimethyl-3-oxazolinecarboxylate and 4-bromoaniline. White solid. MS (ISP): 286.1 ([{$^{81}$Br}M+H]+), 284.2 ([{$^{79}$Br}M+H]+)

Example 32

(S)-4-{[(4-Bromo-phenyl)-ethyl-amino]-methyl}-4,5-dihydro-oxazol-2-ylamine

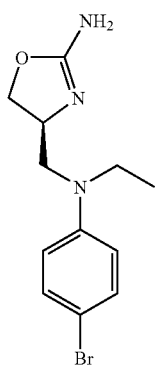

In analogy to example 1 the title compound was prepared starting from tert-butyl (R)-(+)-4-formyl-2,2-dimethyl-3-oxazolinecarboxylate and 4-bromoaniline. Colourless gum. MS (ISP): 300.2 ([{$^{81}$Br}M+H]+), 298.2 ([{$^{79}$Br}M+H]+)

Example 33

(S)-4-{[(3,4-Dichloro-phenyl)-ethyl-amino]-methyl}-4,5-dihydro-oxazol-2-ylamine

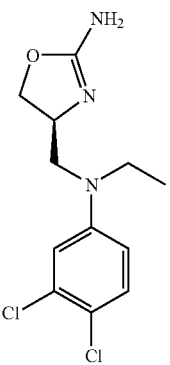

In analogy to example 1 the title compound was prepared starting from tert-butyl (R)-(+)-4-formyl-2,2-dimethyl-3-oxazolinecarboxylate and 3,4-dichloroaniline. Colourless gum. MS (ISP): 292.1 ([{$^{37}$Cl$^{37}$Cl}M+H]+), 290.1 ([{$^{37}$Cl$^{35}$Cl}M+H]+), 288.1 ([{$^{35}$Cl$^{35}$Cl}M+H]+)

Example 34

(S)-4-{[(3-Bromo-phenyl)-methyl-amino]-methyl}-4,5-dihydro-oxazol-2-ylamine

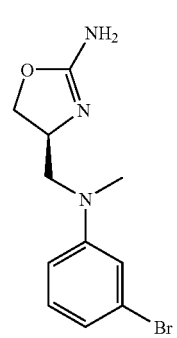

In analogy to example 30 the title compound was prepared starting from tert-butyl (R)-(+)-4-formyl-2,2-dimethyl-3-oxazolinecarboxylate and 3-bromoaniline. Colourless gum. MS (ISP): 286.1 ([{$^{81}$Br}M+H]$^+$), 284.2 ([{$^{79}$Br}M+H]$^+$)

Example 35

(R)-4-[(Methyl-phenyl-amino)-methyl]-4,5-dihydro-oxazol-2-ylamine

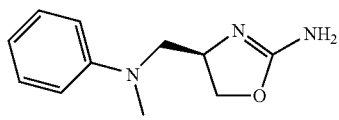

The title compound was prepared in analogy to example 30 starting from (R)-2,2-dimethyl-4-phenylaminomethyl-oxazolidine-3-carboxylic acid tert-butyl ester (example 1.a). Colorless gum. MS (ISP): 206.1 ([M+H]$^+$)

Example 36

(S)-4-{[(3-Bromo-phenyl)-isopropyl-amino]-methyl}-4,5-dihydro-oxazol-2-ylamine

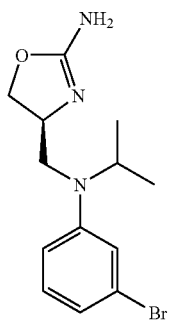

The title compound was prepared in analogy to example 2 starting from tert-butyl (R)-(+)-4-formyl-2,2-dimethyl-3-oxazolinecarboxylate and 3-bromoaniline. Colourless gum. MS (ISP): MS (ISP): 314.2 ([{$^{81}$Br}M+H]$^+$), 312.2 ([{$^{79}$Br}M+H]$^+$)

Example 37

(S)-4-{[(3-Bromo-phenyl)-ethyl-amino]-methyl}-4,5-dihydro-oxazol-2-ylamine

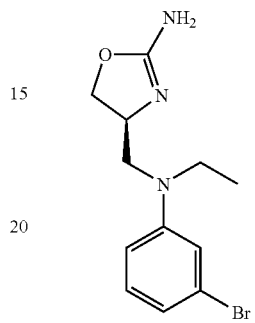

In analogy to example 1 the title compound was prepared starting from tert-butyl (R)-(+)-4-formyl-2,2-dimethyl-3-oxazolinecarboxylate and 3-bromoaniline. Light yellow viscous oil. MS (ISP): 300.2 ([{$^{81}$Br}M+H]$^+$), 298.2 ([{$^{79}$Br}M+H]$^+$)

Example 38

(S)-4-{[(4-Benzyloxy-phenyl)-ethyl-amino]-methyl}-4,5-dihydro-oxazol-2-ylamine

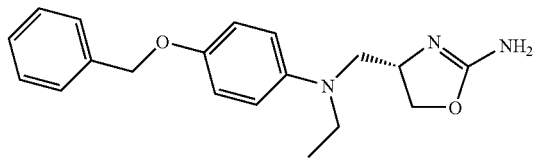

In analogy to example 1 the title compound was prepared starting from tert-butyl (R)-(+)-4-formyl-2,2-dimethyl-3-oxazolinecarboxylate and 4-benzyloxyaniline. Light brown viscous oil. MS (ISP): 326.3 ([M+H]$^+$)

Example 39

(S)-4-{[(3-Benzyl-phenyl)-ethyl-amino]-methyl}-4,5-dihydro-oxazol-2-ylamine

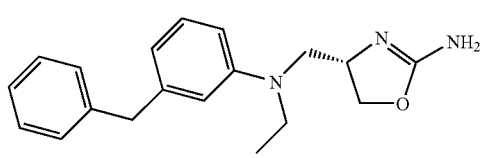

In analogy to example 1 the title compound was prepared starting from tert-butyl (R)-(+)-4-formyl-2,2-dimethyl-3-oxazolinecarboxylate and 3-benzylaniline. Light brown viscous oil. MS (ISP): 310.3 ([M+H]⁺)

Example 40

(S)-4-{[(4-Fluoro-3-methoxy-phenyl)-methyl-amino]-methyl}-4,5-dihydro-oxazol-2-ylamine

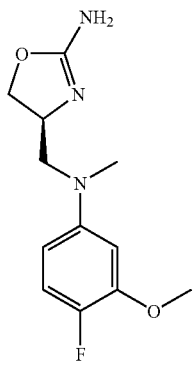

In analogy to example 30 the title compound was prepared starting from tert-butyl (R)-(+)-4-formyl-2,2-dimethyl-3-oxazolinecarboxylate and 4-fluoro-3-methoxyaniline. Colourless gum. MS (ISP): 254.4 ([M+H]⁺)

Example 41

(S)-4-{[(4-Fluoro-3-methoxy-phenyl)-isopropyl-amino]-methyl}-4,5-dihydro-oxazol-2-ylamine

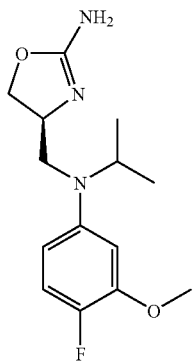

The title compound was prepared in analogy to example 2 starting from tert-butyl (R)-(+)-4-formyl-2,2-dimethyl-3-oxazolinecarboxylate and 4-fluoro-3-methoxyaniline. Light yellow gum. MS (ISP): 282.4 ([M+H]⁺)

Example 42

(S)-4-{[Benzyl-(4-fluoro-3-methoxy-phenyl)-amino]-methyl}-4,5-dihydro-oxazol-2-ylamine

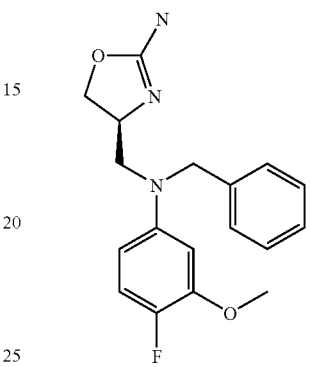

In analogy to example 20 the title compound was prepared starting from tert-butyl (R)-(+)-4-formyl-2,2-dimethyl-3-oxazolinecarboxylate and 4-fluoro-3-methoxyaniline. Colourless gum. MS (ISP): 330.4 ([M+H]⁺)

Example 43

(S)-4-[(4-Fluoro-3-methoxy-phenylamino)-methyl]-4,5-dihydro-oxazol-2-ylamine

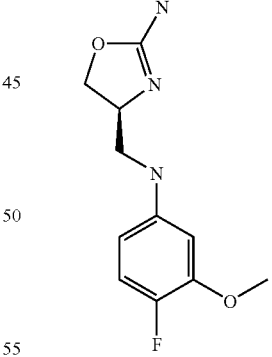

To a stirred solution of (S)-4-{[benzyl-(4-fluoro-3-methoxy-phenyl)-amino]-methyl}-4,5-dihydro-oxazol-2-ylamine (150 mg, example 42) at r.t. in methanol (25 ml) were added ammonium formate (30 mg) and 10% palladium on activated charcoal (48 mg). The resulting suspension was stirred at 75° C. overnight and the mixture was then cooled to room temperature, filtered, and the filtrate was concentrated in vacuo. The residue was purified by column chromatography (SiO₂; gradient:dichloromethane->dichloromethane/ methanol 9:1) to give (S)-4-[(4-fluoro-3-methoxy-phenylamino)-methyl]-4,5-dihydro-oxazol-2-ylamine (39 mg, 36%) as a light yellow gum. MS (ISP): 240.1 ([M+H]⁺)

Example 44

(S)-4-[(Methyl-p-tolyl-amino)-methyl]-4,5-dihydro-oxazol-2-ylamine

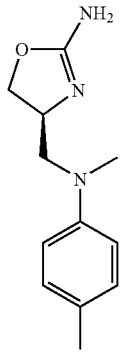

In analogy to example 30 the title compound was prepared starting from tert-butyl (R)-(+)-4-formyl-2,2-dimethyl-3-oxazolinecarboxylate and 4-methylaniline. Colourless gum. MS (ISP): 220.2 ([M+H]⁺)

Example 45

(S)-4-[(Isopropyl-p-tolyl-amino)-methyl]-4,5-dihydro-oxazol-2-ylamine

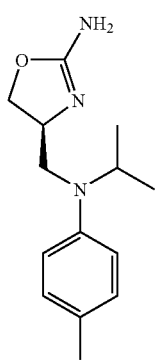

The title compound was prepared in analogy to example 2 starting from tert-butyl (R)-(+)-4-formyl-2,2-dimethyl-3-oxazolinecarboxylate and 4-methylaniline. Colourless gum. MS (ISP): 248.4 ([M+H]⁺)

Example 46

(S)-4-[(Benzyl-p-tolyl-amino)-methyl]-4,5-dihydro-oxazol-2-ylamine

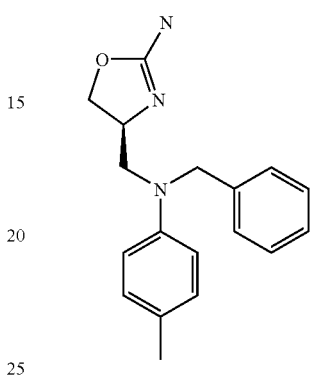

In analogy to example 20 the title compound was prepared starting from tert-butyl (R)-(+)-4-formyl-2,2-dimethyl-3-oxazolinecarboxylate and 4-methylaniline. Colourless gum. MS (ISP): 296.3 ([M+H]⁺)

Example 47

(S)-4-{[Ethyl-(4-fluoro-3-methoxy-phenyl)-amino]-methyl}-4,5-dihydro-oxazol-2-ylamine

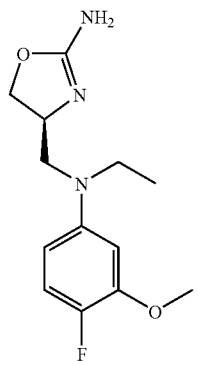

In analogy to example 1 the title compound was prepared starting from tert-butyl (R)-(+)-4-formyl-2,2-dimethyl-3-oxazolinecarboxylate and 4-fluoro-3-methoxyaniline. Light yellow gum. MS (ISP): 268.3 ([M+H]⁺)

Example 48

(S)-4-(p-Tolylamino-methyl)-4,5-dihydro-oxazol-2-ylamine

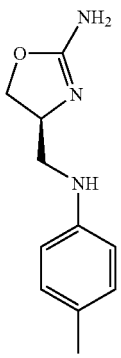

In analogy to example 43 the title compound was prepared starting from (S)-4-[(benzyl-p-tolyl-amino)-methyl]-4,5-dihydro-oxazol-2-ylamine (example 46). Colourless gum. MS (ISP): 206.3 ([M+H]⁺)

Example 49

(S)-4-{[Methyl-(4-phenoxy-phenyl)-amino]-methyl}-4,5-dihydro-oxazol-2-ylamine

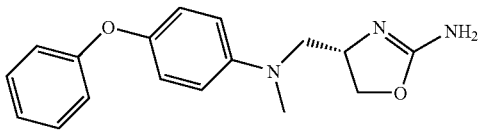

In analogy to example 30 the title compound was prepared starting from tert-butyl (R)-(+)-4-formyl-2,2-dimethyl-3-oxazolinecarboxylate and 4-phenoxyaniline. Colorless viscous oil. MS (ISP): 298.3 ([M+H]⁺)

Example 50

(S)-4-{[Ethyl-(4-phenoxy-phenyl)-amino]-methyl}-4,5-dihydro-oxazol-2-ylamine

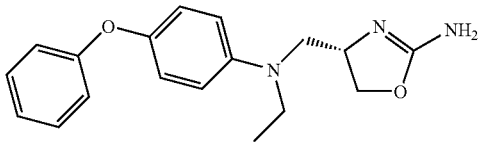

In analogy to example 1 the title compound was prepared starting from tert-butyl (R)-(+)-4-formyl-2,2-dimethyl-3-oxazolinecarboxylate and 4-phenoxyaniline. Light yellow viscous oil. MS (ISP): 312.4 ([M+H]⁺)

Example 51

(S)-4-[(Benzyl-m-tolyl-amino)-methyl]-4,5-dihydro-oxazol-2-ylamine

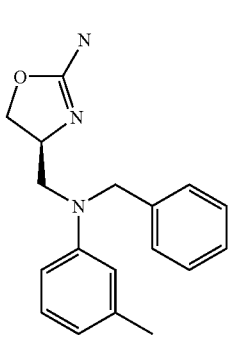

In analogy to example 20 the title compound was prepared starting from tert-butyl (R)-(+)-4-formyl-2,2-dimethyl-3-oxazolinecarboxylate and 3-methylaniline. Colourless gum. MS (ISP): 296.4 ([M+H]⁺)

Example 52

(S)-4-[(Methyl-m-tolyl-amino)-methyl]-4,5-dihydro-oxazol-2-ylamine

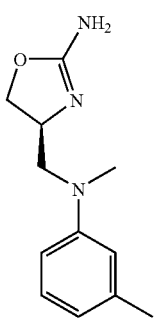

In analogy to example 30 the title compound was prepared starting from tert-butyl (R)-(+)-4-formyl-2,2-dimethyl-3-oxazolinecarboxylate and 3-methylaniline. Colourless gum. MS (ISP): 220.3 ([M+H]⁺)

Example 53

(S)-4-{[Benzyl-(4-fluoro-phenyl)-amino]-methyl}-4,5-dihydro-oxazol-2-ylamine

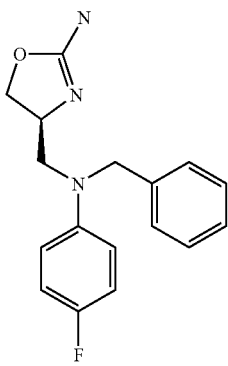

In analogy to example 20 the title compound was prepared starting from tert-butyl (R)-(+)-4-formyl-2,2-dimethyl-3-oxazolinecarboxylate and 4-fluoroaniline. Light brown gum. MS (ISP): 300.3 ([M+H]$^+$)

Example 54

(S)-4-{[Benzyl-(3,4-dichloro-phenyl)-amino]-methyl}-4,5-dihydro-oxazol-2-ylamine

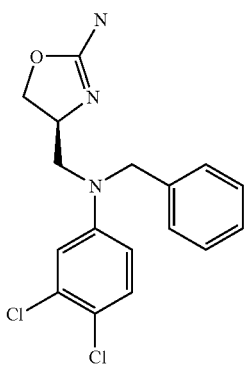

In analogy to example 20 the title compound was prepared starting from tert-butyl (R)-(+)-4-formyl-2,2-dimethyl-3-oxazolinecarboxylate and 3,4-dichloroaniline. Colourless gum. MS (ISP): 354.2 ([{$^{37}$Cl$^{37}$Cl}M+H]$^+$), 352.1 ([{$^{37}$Cl$^{35}$Cl}M+H]$^+$), 350.3 ([{$^{35}$Cl$^{35}$Cl}M+H]$^+$)

Example 55

(S)-4-[{Benzyl-(4-chloro-phenyl)-amino]-methyl}-4,5-dihydro-oxazol-2-ylamine

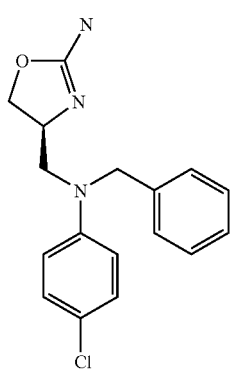

In analogy to example 20 the title compound was prepared starting from tert-butyl (R)-(+)-4-formyl-2,2-dimethyl-3-oxazolinecarboxylate and 4-chloroaniline. Colourless gum. MS (ISP): 318.1 ([{$^{37}$Cl}M+H]$^+$), 316.1 ([{$^{35}$Cl}M+H]$^+$)

Example 56

(S)-4-(m-Tolylamino-methyl)-4,5-dihydro-oxazol-2-ylamine

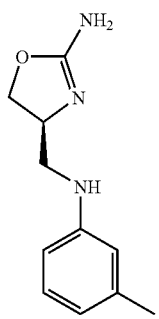

In analogy to example 43 the title compound was prepared starting from (S)-4-[(benzyl-m-tolyl-amino)-methyl]-4,5-dihydro-oxazol-2-ylamine (example 51). Colourless gum. MS (ISP): 206.4 ([M+H]$^+$)

Example 57

(S)-4-Phenylaminomethyl-4,5-dihydro-oxazol-2-ylamine

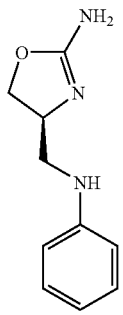

In analogy to example 43 the title compound was prepared starting from (S)-4-[(benzyl-phenyl-amino)-methyl]-4,5-dihydro-oxazol-2-ylamine (example 20). Colourless gum. MS (ISP): 192.3 ([M+H]$^+$)

Example 58

(S)-4-{[(4-Methoxy-3-trifluoromethyl-phenyl)-methyl-amino]-methyl}-4,5-dihydro-oxazol-2-ylamine

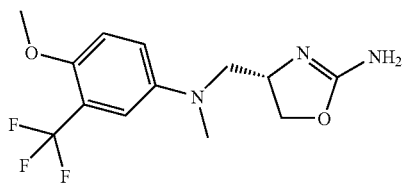

In analogy to example 30 the title compound was prepared starting from tert-butyl (R)-(+)-4-formyl-2,2-dimethyl-3-oxazolinecarboxylate and 4-methoxy-3-trifluoromethylaniline. Colorless viscous oil. MS (ISP): 304.0 ([M+H]$^+$)

Example 59

(R)-4-{[(4-Bromo-phenyl)-methyl-amino]-methyl}-4,5-dihydro-oxazol-2-ylamine

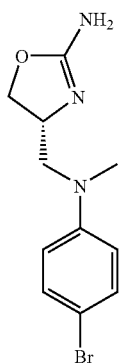

In analogy to example 30 the title compound was prepared starting from tert-butyl (R)-(+)-4-formyl-2,2-dimethyl-3-oxazolinecarboxylate and 4-bromoaniline. White solid. MS (ISP): 285.9 ([{$^{81}$Br}M+H]$^+$), 283.9 ([{$^{79}$Br}M+H]$^+$)

Example 60

(S)-4-{[Ethyl-(3-methoxy-5-trifluoromethyl-phenyl)-amino]-methyl}-4,5-dihydro-oxazol-2-ylamine

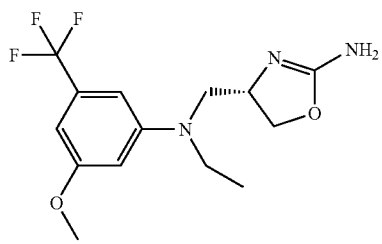

In analogy to example 1 the title compound was prepared starting from tert-butyl (R)-(+)-4-formyl-2,2-dimethyl-3-oxazolinecarboxylate and 3-methoxy-5-trifluoromethylaniline. Light yellow viscous oil. MS (ISP): 318.1 ([M+H]$^+$)

Example 61

(S)-4-{[Ethyl-(3-isopropyl-phenyl)-amino]-methyl}-4,5-dihydro-oxazol-2-ylamine

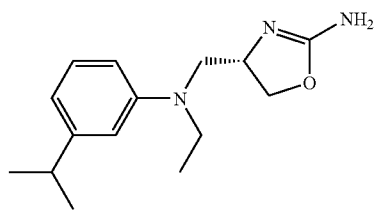

In analogy to example 1 the title compound was prepared starting from tert-butyl (R)-(+)-4-formyl-2,2-dimethyl-3-oxazolinecarboxylate and 3-isopropylaniline. Light yellow viscous oil. MS (ISP): 262.3 ([M+H]$^+$)

Example 62

(S)-4-{[(3-Isopropyl-phenyl)-methyl-amino]-methyl}-4,5-dihydro-oxazol-2-ylamine

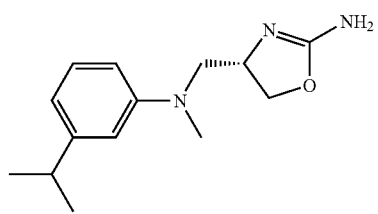

In analogy to example 30 the title compound was prepared starting from tert-butyl (R)-(+)-4-formyl-2,2-dimethyl-3-oxazolinecarboxylate and 3-isopropylaniline. Colorless viscous oil. MS (ISP): 248.1 ([M+H]⁺)

Example 63

(S)-4-{[(3-Methoxy-5-trifluoromethyl-phenyl)-methyl-amino]-methyl}-4,5-dihydro-oxazol-2-ylamine

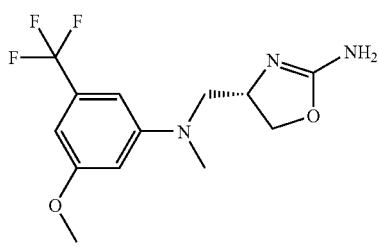

In analogy to example 30 the title compound was prepared starting from tert-butyl (R)-(+)-4-formyl-2,2-dimethyl-3-oxazolinecarboxylate and 3-methoxy-5-trifluoromethylaniline. Colorless viscous oil. MS (ISP): 304.0 ([M+H]⁺)

Example 64

(S)-4-{[(3-Fluoro-phenyl)-(4-methoxy-benzyl)-amino]-methyl}-4,5-dihydro-oxazol-2-ylamine a) (3-Fluoro-phenyl)-(4-methoxy-benzyl)-amine

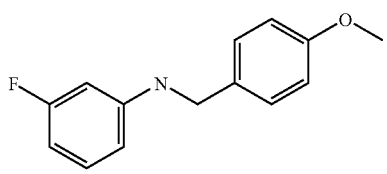

To a stirred solution of anisaldehyde (0.30 ml) at r.t. in methanol (15 ml) under an argon atmosphere were added 3-fluoroaniline (0.22 ml), ZnCl₂ (1.21 g) and NaBH₃CN (0.43 g). The mixture was stirred at 40° C. for 1 h, then cooled to r.t. and concentrated in vacuo. The residue was purified by column chromatography (SiO₂; gradient:heptane->heptane/ EtOAc 7:3) to give (3-fluoro-phenyl)-(4-methoxy-benzyl)-amine (617 mg) as a light yellow oil. MS (ISP): 232.1 ([M+H]⁺)

b) (S)-4-{[(3-Fluoro-phenyl)-(4-methoxy-benzyl)-amino]-methyl}-2,2-dimethyl-oxazolidine-3-carboxylic acid tert-butyl ester

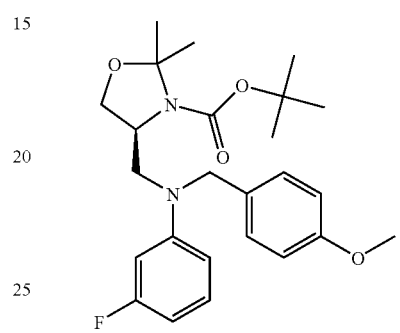

To a stirred solution of tert-butyl (R)-(+)-4-formyl-2,2-dimethyl-3-oxazolinecarboxylate (600 mg) at r.t. in methanol (15 ml) under an argon atmosphere were added (3-fluoro-phenyl)-(4-methoxy-benzyl)-amine (654 mg), ZnCl₂ (1.44 g) and NaBH₃CN (0.52 g). The mixture was stirred at 50° C. for 16 h, then cooled to r.t. and concentrated in vacuo. The residue was purified by column chromatography (SiO₂; gradient: heptane->heptane/EtOAc 7:3) to give (S)-4-{[(3-fluoro-phenyl)-(4-methoxy-benzyl)-amino]-methyl}-2,2-dimethyl-oxazolidine-3-carboxylic acid tert-butyl ester (191 mg, 17%) as a colourless viscous oil. MS (ISP): 445.5 ([M+H]⁺)

c) (S)-2-Amino-3-[(3-fluoro-phenyl)-(4-methoxy-benzyl)-amino]-propan-1-ol

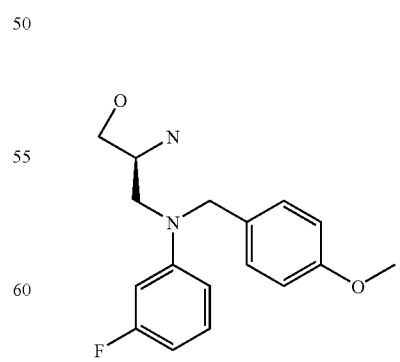

In analogy to example 1.c (S)-4-{[(3-fluoro-phenyl)-(4-methoxy-benzyl)-amino]-methyl}-2,2-dimethyl-oxazolidine-3-carboxylic acid tert-butyl ester was converted to (S)-

2-amino-3-[(3-fluoro-phenyl)-(4-methoxy-benzyl)-amino]-propan-1-ol. Light yellow viscous oil. MS (ISP): 305.4 ([M+H]$^+$)

d) (S)-4-{[(3-Fluoro-phenyl)-(4-methoxy-benzyl)-amino]-methyl}-4,5-dihydro-oxazol-2-ylamine

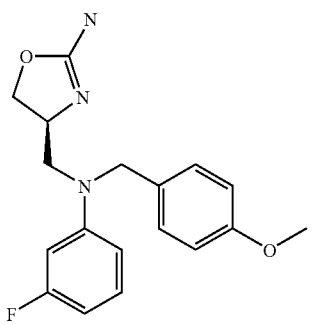

In analogy to example 1.d (S)-2-amino-3-[(3-fluoro-phenyl)-(4-methoxy-benzyl)-amino]-propan-1-ol was reacted with cyanogen bromide to give (S)-4-{[(3-fluoro-phenyl)-(4-methoxy-benzyl)-amino]-methyl}-4,5-dihydro-oxazol-2-ylamine. Light yellow gum. MS (ISP): 330.3 ([M+H]$^+$)

Example 65

(S)-4-[(Ethyl-m-tolyl-amino)-methyl]-4,5-dihydro-oxazol-2-ylamine

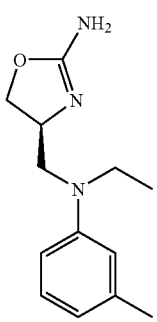

In analogy to example 1 the title compound was prepared starting from tert-butyl (R)-(+)-4-formyl-2,2-dimethyl-3-oxazolinecarboxylate and 3-methylaniline. Colourless gum. MS (ISP): 234.3 ([M+H]$^+$)

Example 66

(S)-4-{[Ethyl-(4-methoxy-3-trifluoromethyl-phenyl)-amino]-methyl}-4,5-dihydro-oxazol-2-ylamine

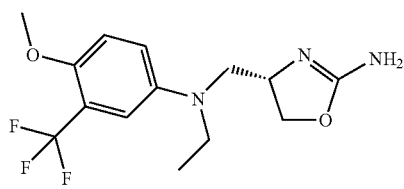

In analogy to example 1 the title compound was prepared starting from tert-butyl (R)-(+)-4-formyl-2,2-dimethyl-3-oxazolinecarboxylate and 4-methoxy-3-trifluoromethylaniline. Colorless viscous oil. MS (ISP): 318.1 ([M+H]$^+$)

Example 67

(S)-4-{[(4-Cyclohexyl-phenyl)-methyl-amino]-methyl}-4,5-dihydro-oxazol-2-ylamine

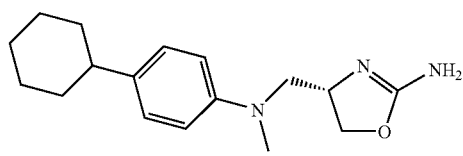

In analogy to example 30 the title compound was prepared starting from tert-butyl (R)-(+)-4-formyl-2,2-dimethyl-3-oxazolinecarboxylate and 4-cyclohexylaniline. Off-white solid. MS (ISP): 288.0 ([M+H]$^+$)

Example 68

(S)-4-{[(3-Fluoro-4-trifluoromethyl-phenyl)-methyl-amino]-methyl}-4,5-dihydro-oxazol-2-ylamine

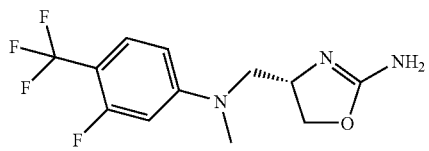

In analogy to example 30 the title compound was prepared starting from tert-butyl (R)-(+)-4-formyl-2,2-dimethyl-3-oxazolinecarboxylate and 3-fluoro-4-trifluoromethylaniline. Light yellow viscous oil. MS (ISP): 292.3 ([M+H]$^+$)

Example 69

(S)-4-{[(4-Cyclohexyl-phenyl)-ethyl-amino]-methyl}-4,5-dihydro-oxazol-2-ylamine

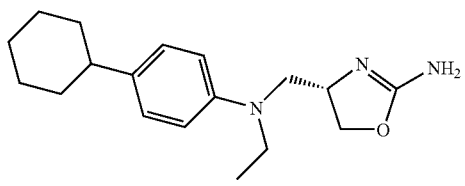

In analogy to example 1 the title compound was prepared starting from tert-butyl (R)-(+)-4-formyl-2,2-dimethyl-3-oxazolinecarboxylate and 4-cyclohexylaniline. Light brown viscous oil. MS (ISP): 302.3 ([M+H]$^+$)

Example 70

(S)-4-{[Ethyl-(3-fluoro-4-trifluoromethyl-phenyl)-amino]-methyl}-4,5-dihydro-oxazol-2-ylamine

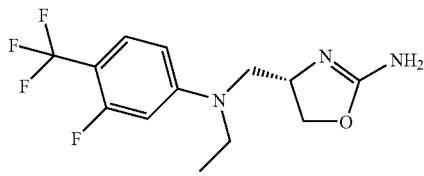

In analogy to example 1 the title compound was prepared starting from tert-butyl (R)-(+)-4-formyl-2,2-dimethyl-3-oxazolinecarboxylate and 3-fluoro-4-trifluoromethylaniline. Off-white solid. MS (ISP): 306.1 ([M+H]$^+$)

Example 71

(S)-4-{[Methyl-(3-trifluoromethyl-phenyl)-amino]-methyl}-4,5-dihydro-oxazol-2-ylamine

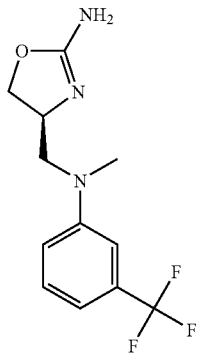

In analogy to example 30 the title compound was prepared starting from tert-butyl (R)-(+)-4-formyl-2,2-dimethyl-3-ox-azolinecarboxylate and 3-trifluoromethylaniline. Light yellow viscous oil. MS (ISP): 273.9 ([M+H]$^+$)

Example 72

(S)-4-[(Methyl-o-tolyl-amino)-methyl]-4,5-dihydro-oxazol-2-ylamine

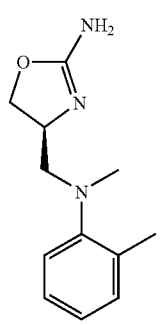

In analogy to example 30 the title compound was prepared starting from tert-butyl (R)-(+)-4-formyl-2,2-dimethyl-3-oxazolinecarboxylate and 2-methylaniline. Light yellow viscous oil. MS (ISP): 220.3 ([M+H]$^+$)

Example 73

(S)-4-{[Ethyl-(3-trifluoromethyl-phenyl)-amino]-methyl}-4,5-dihydro-oxazol-2-ylamine

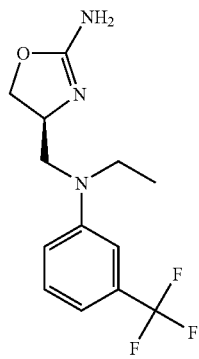

In analogy to example 1 the title compound was prepared starting from tert-butyl (R)-(+)-4-formyl-2,2-dimethyl-3-oxazolinecarboxylate and 3-trifluoromethylaniline. Light yellow viscous oil. MS (ISP): 288.0 ([M+H]$^+$)

Example 74

(S)-4-{[(2-Fluoro-phenyl)-methyl-amino]-methyl}-4,5-dihydro-oxazol-2-ylamine

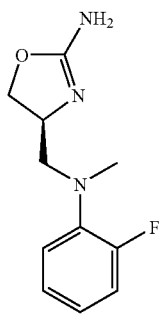

In analogy to example 30 the title compound was prepared starting from tert-butyl (R)-(+)-4-formyl-2,2-dimethyl-3-oxazolinecarboxylate and 2-fluoroaniline. Light yellow viscous oil. MS (ISP): 224.1 ([M+H]$^+$)

Example 75

(S)-4-{[Ethyl-(4-isopropyl-phenyl)-amino]-methyl}-4,5-dihydro-oxazol-2-ylamine

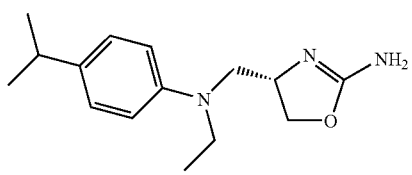

In analogy to example 1 the title compound was prepared starting from tert-butyl (R)-(+)-4-formyl-2,2-dimethyl-3-oxazolinecarboxylate and 4-isopropylaniline. Off-white waxy solid. MS (ISP): 262.3 ([M+H]$^+$)

Example 76

(S)-4-{[(4-Isopropyl-phenyl)-methyl-amino]-methyl}-4,5-dihydro-oxazol-2-ylamine

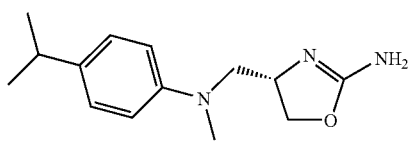

In analogy to example 30 the title compound was prepared starting from tert-butyl (R)-(+)-4-formyl-2,2-dimethyl-3-ox-azolinecarboxylate and 4-isopropylaniline. Light yellow waxy solid. MS (ISP): 248.3 ([M+H]$^+$)

Example 77

(S)-4-[(Methyl-naphthalen-2-yl-amino)-methyl]-4,5-dihydro-oxazol-2-ylamine

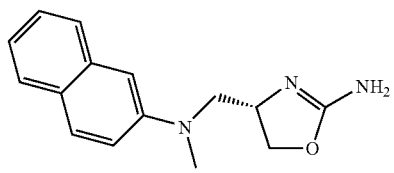

In analogy to example 30 the title compound was prepared starting from tert-butyl (R)-(+)-4-formyl-2,2-dimethyl-3-oxazolinecarboxylate and β-naphthyl amine. Off-white solid. MS (ISP): 256.1 ([M+H]$^+$)

Example 78

(S)-4-[(Ethyl-naphthalen-1-yl-amino)-methyl]-4,5-dihydro-oxazol-2-ylamine

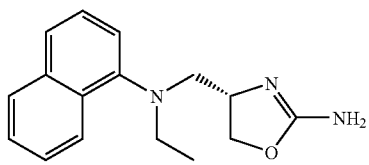

In analogy to example 1 the title compound was prepared starting from tert-butyl (R)-(+)-4-formyl-2,2-dimethyl-3-oxazolinecarboxylate and α-naphthyl amine. Colorless waxy solid. MS (ISP): 270.4 ([M+H]$^+$)

Example 79

(S)-4-[(Methyl-naphthalen-1-yl-amino)-methyl]-4,5-dihydro-oxazol-2-ylamine

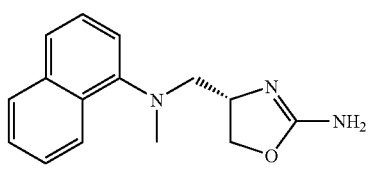

In analogy to example 30 the title compound was prepared starting from tert-butyl (R)-(+)-4-formyl-2,2-dimethyl-3-oxazolinecarboxylate and α-naphthyl amine. Colorless waxy solid. MS (ISP): 256.1 ([M+H]⁺)

Example 80

(S)-4-[(Ethyl-naphthalen-2-yl-amino)-methyl]-4,5-dihydro-oxazol-2-ylamine

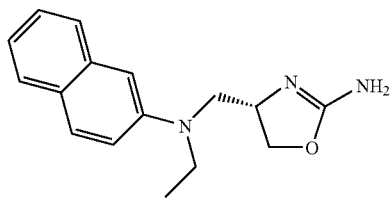

In analogy to example 1 the title compound was prepared starting from tert-butyl (R)-(+)-4-formyl-2,2-dimethyl-3-oxazolinecarboxylate and β-naphthyl amine. Light brown viscous oil. MS (ISP): 270.1 ([M+H]⁺)

Example 81

(S)-4-{[Ethyl-(4-oxazol-5-yl-phenyl)-amino]-methyl}-4,5-dihydro-oxazol-2-ylamine

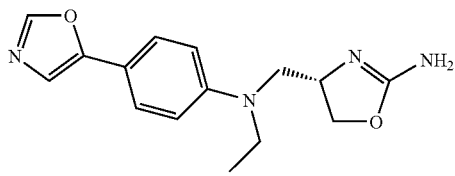

In analogy to example 1 the title compound was prepared starting from tert-butyl (R)-(+)-4-formyl-2,2-dimethyl-3-oxazolinecarboxylate and 4-oxazol-5-yl-phenylamine. Light brown viscous oil. MS (ISP): 287.1 ([M+H]⁺)

Example 82

(S)-4-{[(3-Chloro-phenyl)-methyl-amino]-methyl}-4,5-dihydro-oxazol-2-ylamine

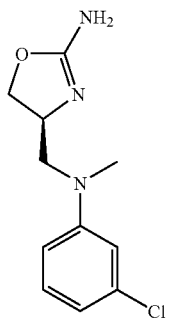

In analogy to example 30 the title compound was prepared starting from tert-butyl (R)-(+)-4-formyl-2,2-dimethyl-3-oxazolinecarboxylate and 3-chloroaniline. Colourless gum. MS (ISP): 242.2 ([{³⁷Cl}M+H]⁺), 240.1 ([{³⁵Cl}M+H]⁺)

Example 83

(S)-4-{[(3-Chloro-phenyl)-ethyl-amino]-methyl}-4,5-dihydro-oxazol-2-ylamine

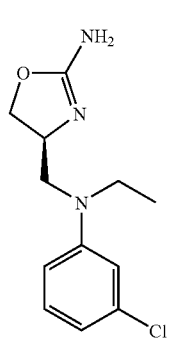

In analogy to example 1 the title compound was prepared starting from tert-butyl (R)-(+)-4-formyl-2,2-dimethyl-3-oxazolinecarboxylate and 3-chloroaniline. Colourless gum. MS (ISP): 256.2 ([{³⁷Cl}M+H]⁺), 254.1 ([{³⁵Cl}M+H]⁺)

Example 84

(S)-4-{[(3-Cyclopropyl-phenyl)-methyl-amino]-methyl}-4,5-dihydro-oxazol-2-ylamine

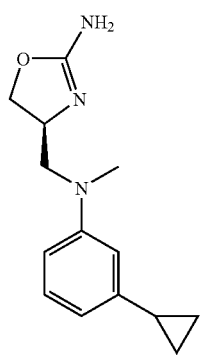

In analogy to example 30 the title compound was prepared starting from tert-butyl (R)-(+)-4-formyl-2,2-dimethyl-3-oxazolinecarboxylate and 3-cyclopropylaniline. Colourless gum. MS (ISP): 246.2 ([M+H]$^+$)

Example 85

(S)-4-{[(3-Cyclopropyl-phenyl)-ethyl-amino]-methyl}-4,5-dihydro-oxazol-2-ylamine

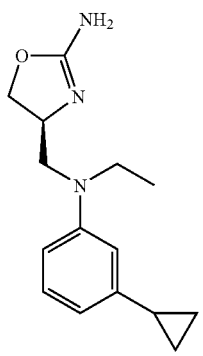

In analogy to example 1 the title compound was prepared starting from tert-butyl (R)-(+)-4-formyl-2,2-dimethyl-3-oxazolinecarboxylate and 3-cyclopropylaniline. Colourless gum. MS (ISP): 260.2 ([M+H]$^+$)

Example 86

(S)-4-{[Methyl-(4-oxazol-5-yl-phenyl)-amino]-methyl}-4,5-dihydro-oxazol-2-ylamine

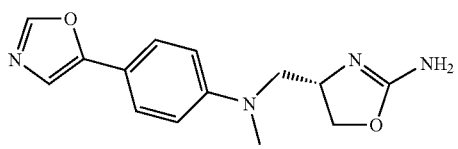

In analogy to example 30 the title compound was prepared starting from tert-butyl (R)-(+)-4-formyl-2,2-dimethyl-3-ox-azolinecarboxylate and 4-oxazol-5-yl-phenylamine. Off-white solid. MS (ISP): 273.0 ([M+H]$^+$)

Example 87

(S)-4-[(3-Chloro-phenylamino)-methyl]-4,5-dihydro-oxazol-2-ylamine a) (S)-4-[(3-Chloro-phenylamino)-methyl]-2,2-dimethyl-oxazolidine-3-carboxylic acid tert-butyl ester

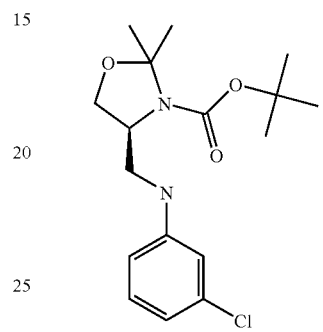

In analogy to example 1.a tert-butyl (R)-(+)-4-formyl-2,2-dimethyl-3-oxazolinecarboxylate was reacted with 3-chloroaniline to give (S)-4-[(3-chloro-phenylamino)-methyl]-2,2-dimethyl-oxazolidine-3-carboxylic acid tert-butyl ester. Off-white solid. MS (ISP): 343.2 ([$^{37}$Cl]M+H]$^+$), 341.1 ([$^{35}$Cl]M+H]$^+$)

b) (S)-4-{[(3-Chloro-phenyl)-(4-methoxy-benzyl)-amino]-methyl}-2,2-dimethyl-oxazolidine-3-carboxylic acid tert-butyl ester

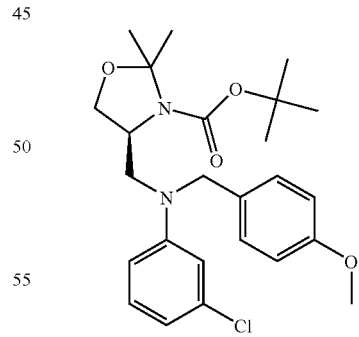

In analogy to example 20.a tert-butyl (S)-4-[(3-chloro-phenylamino)-methyl]-2,2-dimethyl-oxazolidine-3-carboxylic acid tert-butyl ester was reacted with p-anisaldehyde dimethyl acetal to give (S)-4-{[(3-chloro-phenyl)-(4-methoxy-benzyl)-amino]-methyl}-2,2-dimethyl-oxazolidine-3- carboxylic acid tert-butyl ester. White solid. MS (ISP): 463.1 ([{$^{37}$Cl}M+H]$^+$), 461.1 ([{$^{35}$Cl}M+H]$^+$)

c) (S)-4-{[(3-Chloro-phenyl)-(4-methoxy-benzyl)-amino]-methyl}-4,5-dihydro-oxazol-2-ylamine

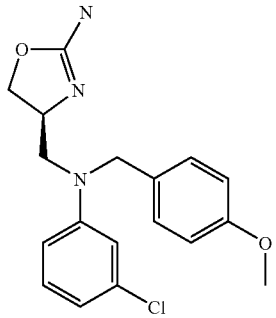

In analogy to example 1.c and 1.d (S)-4-{[(3-chloro-phenyl)-(4-methoxy-benzyl)-amino]-methyl}-2,2-dimethyl-oxazolidine-3-carboxylic acid tert-butyl ester was converted to (S)-4-{[(3-chloro-phenyl)-(4-methoxy-benzyl)-amino]-methyl}-4,5-dihydro-oxazol-2-ylamine. White solid. MS (ISP): 348.3 ([{$^{37}$Cl}M+H]$^+$), 346.1 ([{$^{35}$Cl}M+H]$^+$)

d) (S)-4-[(3-Chloro-phenylamino)-methyl]-4,5-dihydro-oxazol-2-ylamine

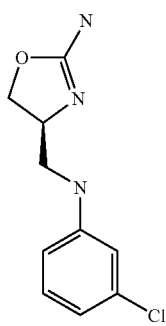

To a stirred solution of (S)-4-{[(3-chloro-phenyl)-(4-methoxy-benzyl)-amino]-methyl}-4,5-dihydro-oxazol-2-ylamine (97 mg) at r.t. in dichloromethane (10 ml) were added anisole (0.31 ml) and trifluoroacetic acid (2.74 ml). The mixture was stirred at r.t. for 48 h and was then concentrated in vacuo. The residue was partitioned between ethyl acetate and saturated aq. sodium bicarbonate solution, the phases were separated, and the organic phase was dried and concentrated in vacuo. The residue was purified by column chromatography (SiO$_2$; gradient:dichloromethane->dichloromethane/methanol 85:15) to give (S)-4-[(3-chloro-phenylamino)-methyl]-4,5-dihydro-oxazol-2-ylamine (22 mg, 35%) as a white gum. MS (ISP): 228.1 ([{$^{37}$Cl}M+H]$^+$), 226.2 ([{$^{35}$Cl}M+H]$^+$)

Example 88

(S)-4-{[(2-Chloro-phenyl)-methyl-amino]-methyl}-4,5-dihydro-oxazol-2-ylamine

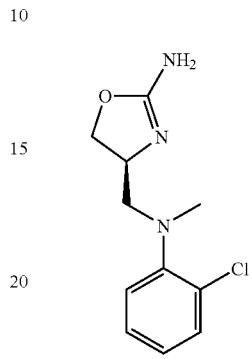

In analogy to example 30 the title compound was prepared starting from tert-butyl (R)-(+)-4-formyl-2,2-dimethyl-3-oxazolinecarboxylate and 2-chloroaniline. Colourless gum. MS (ISP): 242.1 ([{$^{37}$Cl}M+H]$^+$), 240.1 ([{$^{35}$Cl}M+H]$^+$)

Example 89

(S)-4-{[Methyl-(5,6,7,8-tetrahydro-naphthalen-1-yl)-amino]-methyl}-4,5-dihydro-oxazol-2-ylamine

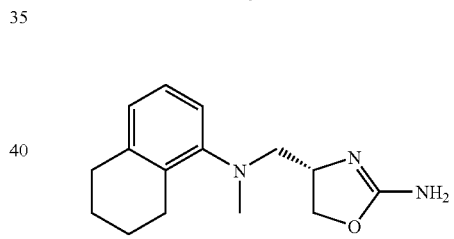

In analogy to example 30 the title compound was prepared starting from tert-butyl (R)-(+)-4-formyl-2,2-dimethyl-3-oxazolinecarboxylate and 5,6,7,8-tetrahydro-naphthalen-1-ylamine. White solid. MS (ISP): 260.0 ([M+H]$^+$)

Example 90

(S)-4-{[Ethyl-(5,6,7,8-tetrahydro-naphthalen-1-yl)-amino]-methyl}-4,5-dihydro-oxazol-2-ylamine

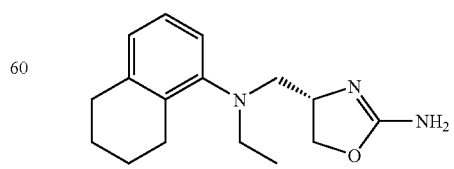

In analogy to example 1 the title compound was prepared starting from tert-butyl (R)-(+)-4-formyl-2,2-dimethyl-3-oxazolinecarboxylate and 5,6,7,8-tetrahydro-naphthalen-1-ylamine. Yellow viscous oil. MS (ISP): 274.4 ([M+H]⁺)

Example 91

(S)-4-{[(3-Ethyl-phenyl)-methyl-amino]-methyl}-4,5-dihydro-oxazol-2-ylamine

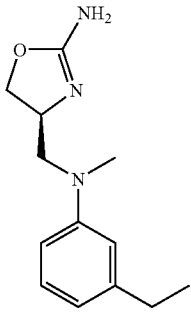

In analogy to example 30 the title compound was prepared starting from tert-butyl (R)-(+)-4-formyl-2,2-dimethyl-3-oxazolinecarboxylate and 3-ethylaniline. Colourless gum. MS (ISP): 234.1 ([M+H]⁺)

Example 92

(S)-4-{[Ethyl-(3-ethyl-phenyl)-amino]-methyl}-4,5-dihydro-oxazol-2-ylamine

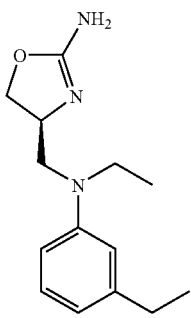

In analogy to example 1 the title compound was prepared starting from tert-butyl (R)-(+)-4-formyl-2,2-dimethyl-3-oxazolinecarboxylate and 3-ethylaniline. Colourless gum. MS (ISP): 248.3 ([M+H]⁺)

Example 93

(S)-4-{[(4-Ethyl-phenyl)-methyl-amino]-methyl}-4,5-dihydro-oxazol-2-ylamine

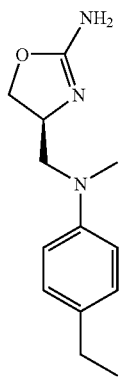

In analogy to example 30 the title compound was prepared starting from tert-butyl (R)-(+)-4-formyl-2,2-dimethyl-3-oxazolinecarboxylate and 4-ethylaniline. Colourless gum. MS (ISP): 234.1 ([M+H]⁺)

Example 94

(S)-4-{[Ethyl-(4-ethyl-phenyl)-amino]-methyl}-4,5-dihydro-oxazol-2-ylamine

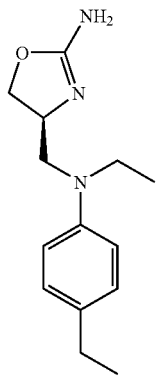

In analogy to example 1 the title compound was prepared starting from tert-butyl (R)-(+)-4-formyl-2,2-dimethyl-3-oxazolinecarboxylate and 4-ethylaniline. Colourless gum. MS (ISP): 248.2 ([M+H]⁺)

Example 95

(S)-4-{[(4-Chloro-2-fluoro-phenyl)-ethyl-amino]-methyl}-4,5-dihydro-oxazol-2-ylamine

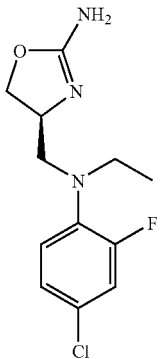

In analogy to example 1 the title compound was prepared starting from tert-butyl (R)-(+)-4-formyl-2,2-dimethyl-3-oxazolinecarboxylate and 4-chloro-2-fluoroaniline. Light yellow viscous oil. MS (ISP): 274.0 ([{$^{37}$Cl}M+H]$^+$), 272.2 ([{$^{35}$Cl}M+H]$^+$)

Example 96

(S)-4-{[Ethyl-(3-[$^2$H]-phenyl)-amino]-methyl}-4,5-dihydro-oxazol-2-ylamine

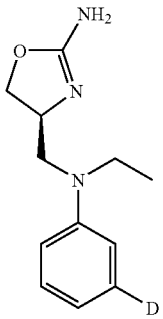

5.0 mg of (S)-4-{[(3-bromo-phenyl)-ethyl-amino]-methyl}-4,5-dihydro-oxazol-2-ylamine (example 37) was dissolved in 0.5 ml of THF and treated with 9.4 µl of triethylamine and 1.8 mg of Pd/C (10%). After cooling to −78° C. the black suspension was evacuated three times and purged with D$_2$. After stirring for 1 h at room temperature the black reaction mixture was filtered over Dicalite. The Dicalite-Pd/C-solid was washed with 2×1 ml of CH$_2$Cl$_2$. The clear solution was concentrated and purified by silica gel column chromatography (CH$_2$Cl$_2$/MeOH 96:4 and 1% of NH$_4$OH (25% in water)). A second purification was necessary in order to obtain product in 98% purity, which was obtained by an RP-18 column (H$_2$O/MeCN 9:1+1% AcOH).

Example 97

(S)-4-{[Ethyl-(3-[$^3$H]-phenyl)-amino]-methyl}-4,5-dihydro-oxazol-2-ylamine

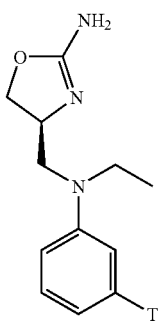

In a 1-ml tritiation-flask was added 2.5 mg of Pd/C (10%). 5.0 mg of (S)-4-{[(3-bromo-phenyl)-ethyl-amino]-methyl}-4,5-dihydro-oxazol-2-ylamine (example 37) was dissolved in 0.4 ml of THF and treated with 4.7 µl of triethylamine and 0.4 ml of MeOH. This solution was also added to the tritiation-flask. The black suspension was degassed four times, frozen with liquid N$_2$ and purged with tritium (13 Ci). The reaction mixture was allowed to warm to RT and a starting pressure of 808 mbar was observed. After 1 h and 20 min, the reaction mixture was cooled with liquid N$_2$ and the tritium gas was taken back to the waste-storage. The suspension was degassed once and the solvent condensed to an ampoule. The black solid was treated 3 times with 1 ml of MeOH and the solvent back-condensed to the ampoule. The residue was suspended in 10 ml of EtOH and filtered over 0.2 µm nylon, obtaining a colorless solution of the crude product with an activity of 385 mCi, which was further dissolved with EtOH to 50 ml. The crude product was obtained in 88.3% purity, which was disclosed by radio-TLC (solid phase: Merck RP-18 F254s, eluent: MeCN/H$_2$O 1:1+1% AcOH, R$_f$ (product): 0.46, R$_f$ (starting material) 0.38).

53.9 mCi (7.7 ml) of the ethanol-solution was concentrated and purified by an RP-18 column chromatography (eluent H$_2$O/MeCN 9:1+1% AcOH). The fractions were analysed by HPLC (see conditions below), and those fractions with a purity of >98% were adjusted to pH~10 with NH$_4$OH (25% in water). The combined fractions were filtered over an RP-18 plaque and washed with water. This aqueous solution was discarded. The product was eluted from the RP-plaque with EtOH and diluted to 25 ml. 25.0 mCi (46.4%) of the product having 98.9% purity were obtained.

Example 98

(S)-4-[(Indan-5-yl-methyl-amino)-methyl]-4,5-dihydro-oxazol-2-ylamine

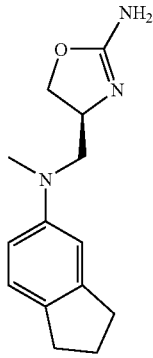

In analogy to example 30 the title compound was prepared starting from tert-butyl (R)-(+)-4-formyl-2,2-dimethyl-3-oxazolinecarboxylate and 5-aminoindane. White solid. MS (ISP): 246.4 ([M+H]$^+$)

Example 99

(S)-4-[(Ethyl-indan-5-yl-amino)-methyl]-4,5-dihydro-oxazol-2-ylamine

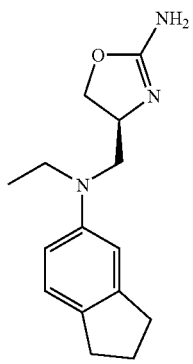

In analogy to example 1 the title compound was prepared starting from tert-butyl (R)-(+)-4-formyl-2,2-dimethyl-3-oxazolinecarboxylate and 5-aminoindane. Off-white solid. MS (ISP): 260.3 ([M+H]$^+$)

Example 100

(S)-4-{[(4-Chloro-2-fluoro-phenyl)-methyl-amino]-methyl}-4,5-dihydro-oxazol-2-ylamine

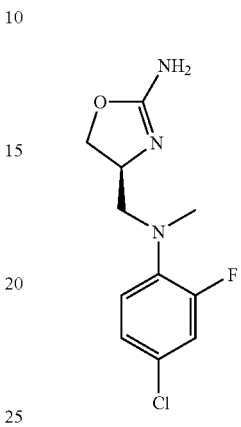

In analogy to example 30 the title compound was prepared starting from tert-butyl (R)-(+)-4-formyl-2,2-dimethyl-3-oxazolinecarboxylate and 4-chloro-2-fluoroaniline. White solid. MS (ISP): 260.1 ([{$^{37}$Cl}M+H]$^+$), 258.0 ([{$^{35}$Cl}M+H]$^+$).

Example 101

(S)-4-[{Methyl-(3-piperidin-1-yl-phenyl)-amino]-methyl}-4,5-dihydro-oxazol-2-ylamine

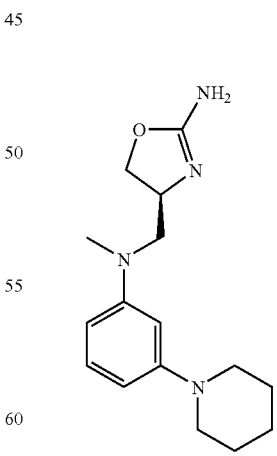

In analogy to example 30 the title compound was prepared starting from tert-butyl (R)-(+)-4-formyl-2,2-dimethyl-3-oxazolinecarboxylate and 3-piperidin-1-yl aniline. Viscous yellow oil. MS (ISP): 289.3 ([M+H]⁺)

Example 102

(S)-4-{[Ethyl-(3-piperidin-1-yl-phenyl)-amino]-methyl}-4,5-dihydro-oxazol-2-ylamine

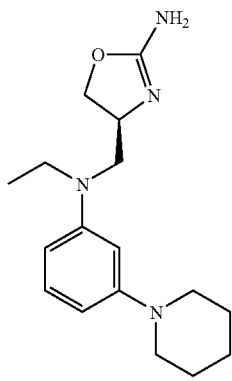

In analogy to example 1 the title compound was prepared starting from tert-butyl (R)-(+)-4-formyl-2,2-dimethyl-3-oxazolinecarboxylate and 3-piperidin-1-yl aniline. Viscous colourless oil. MS (ISP): 303.3 ([M+H]⁺)

Example 103

(S)-4-{[(2,6-Dimethyl-phenyl)-ethyl-amino]-methyl}-4,5-dihydro-oxazol-2-ylamine

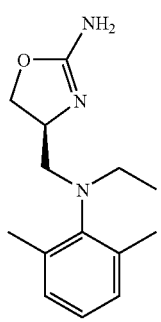

In analogy to example 1 the title compound was prepared starting from tert-butyl (R)-(+)-4-formyl-2,2-dimethyl-3-ox-azolinecarboxylate and 2,6-dimethylaniline. Colourless gum. MS (ISP): 248.1 ([M+H]⁺).

Example 104

(S)-4-{[(2,6-Dimethyl-phenyl)-methyl-amino]-methyl}-4,5-dihydro-oxazol-2-ylamine

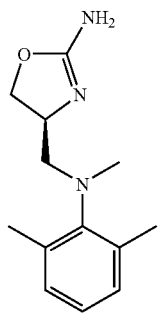

In analogy to example 30 the title compound was prepared starting from tert-butyl (R)-(+)-4-formyl-2,2-dimethyl-3-oxazolinecarboxylate and 2,6-dimethylaniline. Light yellow gum. MS (ISP): 234.3 ([M+H]⁺)

Example 105

(S)-4-{[Methyl-(3-oxazol-5-yl-phenyl)-amino]-methyl}-4,5-dihydro-oxazol-2-ylamine

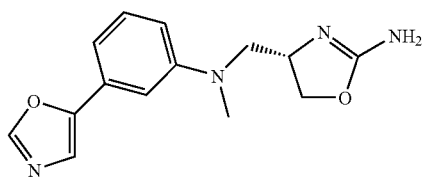

In analogy to example 30 the title compound was prepared starting from tert-butyl (R)-(+)-4-formyl-2,2-dimethyl-3-oxazolinecarboxylate and 3-(1,3-oxazol-5-yl)amine. Off-white solid. MS (ISP): 273.3 ([M+H]⁺)

Example 106

(S)-4-{[Ethyl-(3-oxazol-5-yl-phenyl)-amino]-methyl}-4,5-dihydro-oxazol-2-ylamine

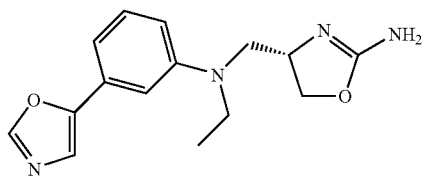

In analogy to example 1 the title compound was prepared starting from tert-butyl (R)-(+)-4-formyl-2,2-dimethyl-3-oxazolinecarboxylate and 3-(1,3-oxazol-5-yl)amine. Viscous yellow oil. MS (ISP): 287.0 ([M+H]⁺)

Example 107

(S)-4-{[Ethyl-(2-fluoro-phenyl)-amino]-methyl}-4,5-dihydro-oxazol-2-ylamine

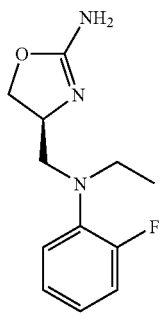

In analogy to example 1 the title compound was prepared starting from tert-butyl (R)-(+)-4-formyl-2,2-dimethyl-3-oxazolinecarboxylate and 2-fluoro-aniline. Colourless gum. MS (ISP): 238.1 ([M+H]⁺).

Example 108

(RS)-4-[(Ethyl-phenyl-amino)-methyl]-4-methyl-4,5-dihydro-oxazol-2-ylamine

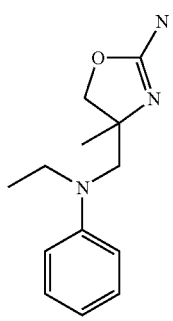

a) (RS)-2,2,4-Trimethyl-4-phenylaminomethyl-oxazolidine-3-carboxylic acid tert-butyl ester

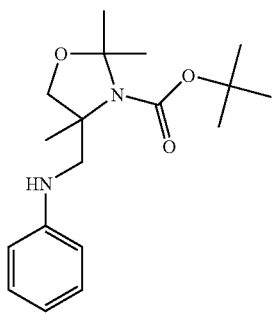

To a stirred solution of (RS)-4-formyl-2,2,4-trimethyl-oxazolidine-3-carboxylic acid tert-butyl ester (300 mg) at r.t. in methanol (3 ml) was added aniline (132 mg) and the mixture was heated at 80° C. for 3 h. NaBH₄ (93 mg) was then added and the mixture was stirred at 60° C. for 16 h, then cooled to r.t. and concentrated in vacuo. The residue was purified by column chromatography (SiO₂; gradient:heptane/ethyl acetate) to give (RS)-2,2,4-trimethyl-4-phenylaminomethyl-oxazolidine-3-carboxylic acid tert-butyl ester (181 mg, 46%) as a yellow oil. MS (ISP): 321.1 ([M+H]⁺).

b) (RS)-4-[(Ethyl-phenyl-amino)-methyl]-2,2,4-trimethyl-oxazolidine-3-carboxylic acid tert-butyl ester

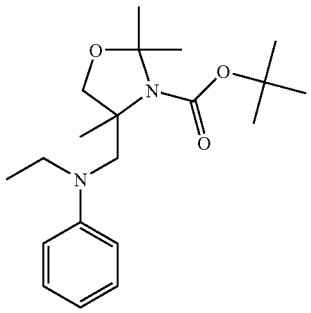

In analogy to example 1.b (RS)-2,2,4-trimethyl-4-phenylaminomethyl-oxazolidine-3-carboxylic acid tert-butyl ester was reacted with acetaldehyde to give (RS)-4-[(ethyl-phenyl-amino)-methyl]-2,2,4-trimethyl-oxazolidine-3-carboxylic acid tert-butyl ester. Colourless oil. MS (ISP): 349.5 ([M+H]⁺).

c) (RS)-2-Amino-3-(ethyl-phenyl-amino)-2-methyl-propan-1-ol

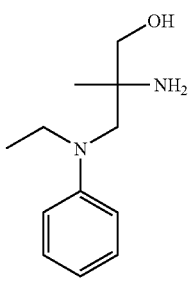

In analogy to example 1.c (RS)-4-[(ethyl-phenyl-amino)-methyl]-2,2,4-trimethyl-oxazolidine-3-carboxylic acid tert-butyl ester was reacted with hydrogen chloride to give (RS)-

2-amino-3-(ethyl-phenyl-amino)-2-methyl-propan-1-ol. Colourless oil. MS (ISP): 209.3 ([M+H]⁺).

d) (RS)-4-[(Ethyl-phenyl-amino)-methyl]-4-methyl-4,5-dihydro-oxazol-2-ylamine

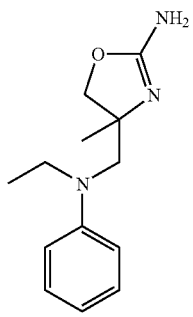

In analogy to example 1.d (RS)-2-amino-3-(ethyl-phenyl-amino)-2-methyl-propan-1-ol was reacted with cyanogen bromide to give (RS)-4-[(ethyl-phenyl-amino)-methyl]-4-methyl-4,5-dihydro-oxazol-2-ylamine as a colourless gum. MS (ISP): 234.0 ([M+H]⁺).

Example 109

(S)-4-{[Ethyl-(3-fluoro-5-trifluoromethyl-phenyl)-amino]-methyl}-4,5-dihydro-oxazol-2-ylamine

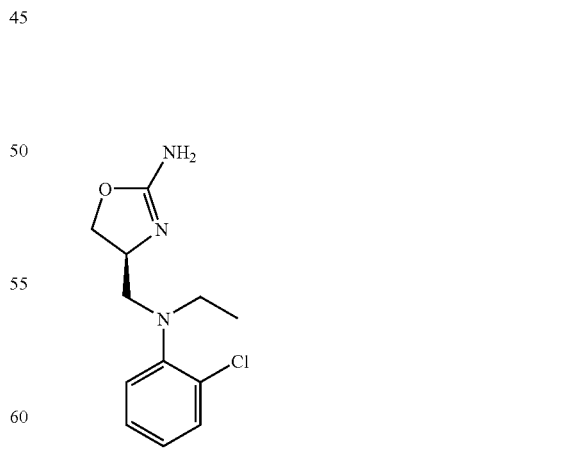

In analogy to example 1 the title compound was prepared starting from tert-butyl (R)-(+)-4-formyl-2,2-dimethyl-3-oxazolinecarboxylate and 3-fluoro-5-trifluoromethylaniline. White waxy solid. MS (ISP): 306.1 ([M+H]⁺)

Example 110

(S)-4-{[Benzyl-(4-bromo-phenyl)-amino]-methyl}-4,5-dihydro-oxazol-2-ylamine

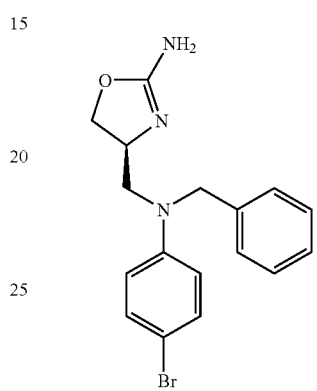

In analogy to example 20 the title compound was prepared starting from tert-butyl (R)-(+)-4-formyl-2,2-dimethyl-3-oxazolinecarboxylate and 4-bromoaniline. Colourless gum. MS (ISP): 362.2 ([{⁸¹Br}M+H]⁺), 360.1 ([{⁷⁹Br}M+H]⁺).

Example 111

(S)-4-{[(2-Chloro-phenyl)-ethyl-amino]-methyl}-4,5-dihydro-oxazol-2-ylamine

In analogy to example 1 the title compound was prepared starting from tert-butyl (R)-(+)-4-formyl-2,2-dimethyl-3-oxazolinecarboxylate and 2-chloro-aniline. Colourless gum. MS (ISP): 256.2 ([{$^{37}$Cl}M+H]$^+$), 254.1 ([{$^{35}$Cl}M+H]$^+$).

Example 112

(S)-4-[(Ethyl-o-tolyl-amino)-methyl]-4,5-dihydro-oxazol-2-ylamine

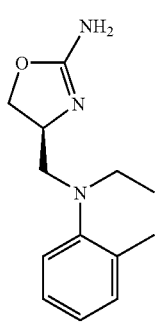

In analogy to example 1 the title compound was prepared starting from tert-butyl (R)-(+)-4-formyl-2,2-dimethyl-3-oxazolinecarboxylate and o-toluidine. Colourless gum. MS (ISP): 234.3 ([M+H]$^+$).

Example 113

(S)-4-{[(2-Fluoro-4-methyl-phenyl)-methyl-amino]-methyl}-4,5-dihydro-oxazol-2-ylamine

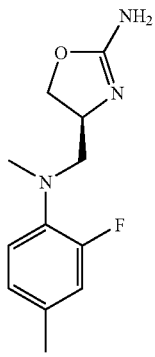

In analogy to example 30 the title compound was prepared starting from tert-butyl (R)-(+)-4-formyl-2,2-dimethyl-3-ox-azolinecarboxylate and 2-fluoro-4-methylaniline. White waxy solid. MS (ISP): 238.1 ([M+H]$^+$)

Example 114

(S)-4-{[(2-Fluoro-4-methyl-phenyl)-isopropyl-amino]-methyl}-4,5-dihydro-oxazol-2-ylamine

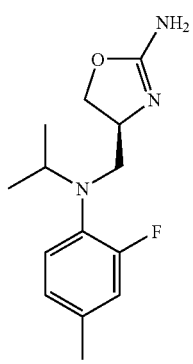

In analogy to example 2 the title compound was prepared starting from tert-butyl (R)-(+)-4-formyl-2,2-dimethyl-3-oxazolinecarboxylate and 2-fluoro-4-methylaniline. Light yellow waxy solid. MS (ISP): 266.0 ([M+H]$^+$)

Example 115

(S)-4-{[Benzyl-(2-fluoro-4-methyl-phenyl)-amino]-methyl}-4,5-dihydro-oxazol-2-ylamine

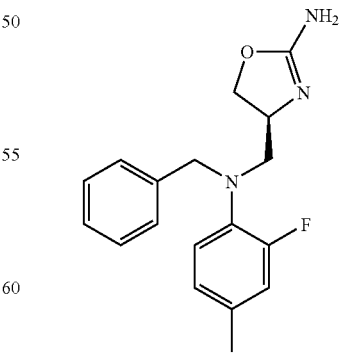

In analogy to example 20 the title compound was prepared starting from tert-butyl (R)-(+)-4-formyl-2,2-dimethyl-3-oxazolinecarboxylate and 2-fluoro-4-methylaniline. Viscous colorless oil. MS (ISP): 314.1 ([M+H]+)

Example 116

(RS)-4-{[(4-Chloro-phenyl)-ethyl-amino]-methyl}-4-methyl-4,5-dihydro-oxazol-2-ylamine

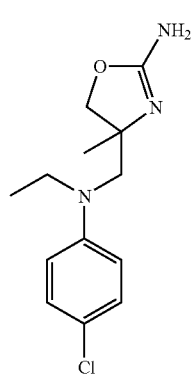

In analogy to example 109 the title compound was prepared starting from (RS)-4-formyl-2,2,4-trimethyl-oxazolidine-3-carboxylic acid tert-butyl ester and 4-chloro-aniline. Colourless gum. MS (ISP): 270.3 ([{$^{37}$Cl}M+H]+), 268.2 ([{$^{35}$Cl}M+H]+).

Example 117

(S)-4-[(2-Fluoro-4-methyl-phenylamino)-methyl]-4,5-dihydro-oxazol-2-ylamine

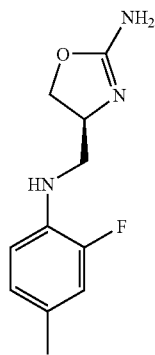

In analogy to examples 20 and 43 the title compound was prepared starting from tert-butyl (R)—(+)-4-formyl-2,2-dimethyl-3-oxazolinecarboxylate and 2-fluoro-4-methylaniline. Waxy white solid. MS (ISP): 224.4 ([M+H]+)

Example 118

(S)-4-{[(4-Chloro-benzyl)-(4-fluoro-3-methoxy-phenyl)-amino]-methyl}-4,5-dihydro-oxazol-2-ylamine

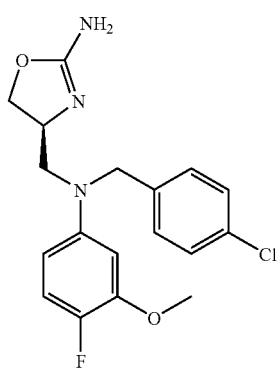

In analogy to example 20 the title compound was prepared starting from tert-butyl (R)-(+)-4-formyl-2,2-dimethyl-3-oxazolinecarboxylate, 4-fluoro-3-methoxyaniline and 4-chlorobenzaldehyde dimethyl acetal. Light yellow gum. MS (ISP): 366.1 ([{$^{37}$Cl}M+H]+), 364.2 ([{$^{35}$Cl}M+H]+).

Example 119

(S)-4-[(2-Chloro-phenylamino)-methyl]-4,5-dihydro-oxazol-2-ylamine

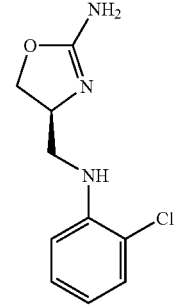

a) (S)-4-[(2-Chloro-phenylamino)-methyl]-2,2-dimethyl-oxazolidine-3-carboxylic acid tert-butyl ester

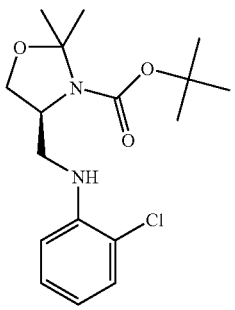

In analogy to example 1.a tert-butyl (R)-(+)-4-formyl-2,2-dimethyl-3-oxazolinecarboxylate was reacted with 2-chloroaniline to give (S)-4-[(2-chloro-phenylamino)-methyl]-2,2-dimethyl-oxazolidine-3-carboxylic acid tert-butyl ester. White solid. MS (ISP): 343.2 ([{$^{37}$Cl}M+H]$^+$), 341.1 ([{$^{35}$Cl}M+H]$^+$).

b) (S)-2-Amino-3-(2-chloro-phenylamino)-propan-1-ol

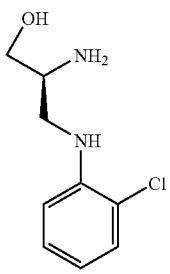

In analogy to example 1.c (S)-4-[(2-chloro-phenylamino)-methyl]-2,2-dimethyl-oxazolidine-3-carboxylic acid tert-butyl ester was reacted with hydrogen chloride to give (S)-2-amino-3-(2-chloro-phenylamino)-propan-1-ol. White solid. MS (ISP): 203.2 ([{$^{37}$Cl}M+H]$^+$), 201.2 ([{$^{35}$Cl}M+H]$^+$).

c) (S)-4-[(Isopropyl-phenyl-amino)-methyl]-4,5-dihydro-oxazol-2-ylamine

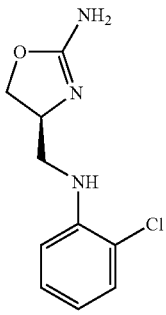

In analogy to example 1.d (S)-2-amino-3-(2-chloro-phenylamino)-propan-1-ol was reacted with cyanogen bromide to give (S)-4-[(isopropyl-phenyl-amino)-methyl]-4,5-dihydro-oxazol-2-ylamine as a colourless gum. MS (ISP): 228.1 ([{$^{37}$Cl}M+H]$^+$), 226.1 ([{$^{35}$Cl}M+H]$^+$).

Examples 120 & 121

(S)-4-{[(4-Chloro-phenyl)-ethyl-amino]-methyl}-4-methyl-4,5-dihydro-oxazol-2-ylamine and (R)-4-{[(4-Chloro-phenyl)-ethyl-amino]-methyl}-4-methyl-4,5-dihydro-oxazol-2-ylamine

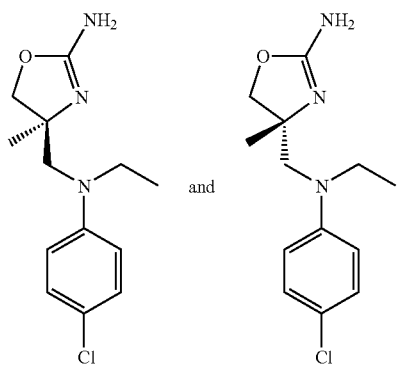

(RS)-4-{[(4-Chloro-phenyl)-ethyl-amino]-methyl}-4-methyl-4,5-dihydro-oxazol-2-ylamine (example 116) was separated by chiral column chromatography (Chiralpak A D, EtOH/heptane=1:10) to yield (S)-4-{[(4-chloro-phenyl)-ethyl-amino]-methyl}-4-methyl-4,5-dihydro-oxazol-2-ylamine (white solid; MS (ISP): 270.3 ([{$^{37}$Cl}M+H]$^+$), 268.2 ([{$^{35}$Cl}M+H]$^+$)) and (R)-4-{[(4-chloro-phenyl)-ethyl-amino]-methyl}-4-methyl-4,5-dihydro-oxazol-2-ylamine (white solid; MS (ISP): 270.3 ([{$^{37}$Cl}M+H]$^+$), 268.2 ([{$^{35}$Cl}M+H]$^+$)).

Example 122

(S)-4-{[Benzyl-(3-fluoro-4-trifluoromethyl-phenyl)-amino]-methyl}-4,5-dihydro-oxazol-2-ylamine

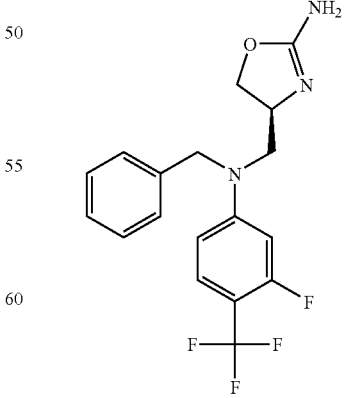

In analogy to example 20 the title compound was prepared starting from tert-butyl (R)-(+)-4-formyl-2,2-dimethyl-3-oxazolinecarboxylate and 3-fluoro-4-trifluoromethylaniline. Viscous colorless oil. MS (ISP): 368.1 ([M+H]⁺)

Example 123

((S)-2-Amino-4,5-dihydro-oxazol-4-ylmethyl)-(2-chloro-pyridin-4-yl)-amine

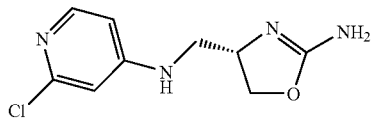

a) ((S)-4-[(2-Chloro-pyridin-4-ylamino)-methyl]-2,2-dimethyl-oxazolidine-3-carboxylic acid tert-butyl ester

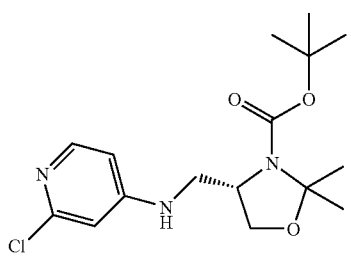

To a stirred solution of tert-butyl (R)-(+)-4-formyl-2,2-dimethyl-3-oxazolinecarboxylate (500 mg) at r.t. in 1,2-dichloroethane (10 ml) under an argon atmosphere was added 2-chloro-4-aminopyridine (255 mg). After 30 min stirring at r.t. were added sodium tri-acetoxyborohydride (523 mg) and acetic acid (0.11 ml). The reaction mixture was stirred overnight at 60° C., then cooled to r.t., diluted with CH$_2$Cl$_2$ and washed with 10% aqueous Na$_2$CO$_3$. The aqueous phase was back extracted with CH$_2$Cl$_2$. The combined organics were washed with brine, dried over MgSO$_4$, filtered and concentrated. The crude product was purified by column chromatography (SiO$_2$; gradient:cyclohexane->cyclo-hexane/EtOAc 3:2) to give (S)-4-[(2-chloro-pyridin-4-ylamino)-methyl]-2,2-dimethyl-oxazolidine-3-carboxylic acid tert-butyl ester (179 mg, 26%) as colorless amorphous solid. MS (ISP): 342.1 ([M+H]⁺)

b) ((S)-2-Amino-4,5-dihydro-oxazol-4-ylmethyl)-(2-chloro-pyridin-4-yl)-amine

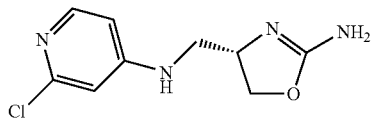

In analogy to example 1.c and 1.d (S)-4-[(2-chloro-pyridin-4-ylamino)-methyl]-2,2-dimethyl-oxazolidine-3-carboxylic acid tert-butyl ester was converted to the title compound. White solid. MS (ISP): 227.3 ([M+H]⁺)

Example 124

(S)-4-(o-Tolylamino-methyl)-4,5-dihydro-oxazol-2-ylamine

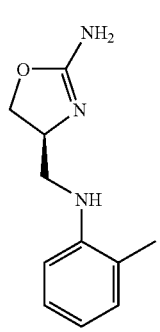

In analogy to example 119 the title compound was prepared starting from tert-butyl (R)-(+)-4-formyl-2,2-dimethyl-3-oxazolinecarboxylate and o-toluidine. Light yellow gum. MS (ISP): 206.1 ([M+H]⁺).

Example 125

(R)-4-{[(4-Chloro-phenyl)-methyl-amino]-methyl}-4,5-dihydro-oxazol-2-ylamine

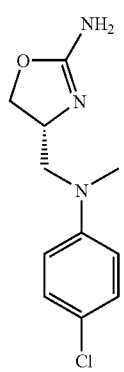

In analogy to example 3 the title compound was prepared starting from tert-butyl (S)-(−)-4-formyl-2,2-dimethyl-3-oxazolinecarboxylate and 4-chloro-N-methylaniline. Colourless gum. MS (ISP): 242.1 ([{$^{37}$Cl}M+H]$^+$), 240.1 ([{$^{35}$Cl}M+H]$^+$).

Example 126

(R)-4-{[(4-Chloro-phenyl)-ethyl-amino]-methyl}-4,5-dihydro-oxazol-2-ylamine

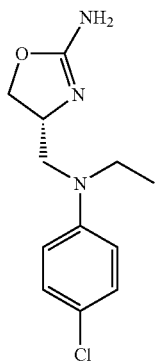

In analogy to example 1 the title compound was prepared starting from tert-butyl (S)-(−)-4-formyl-2,2-dimethyl-3-oxazolinecarboxylate and 4-chloroaniline. Light yellow gum. MS (ISP): 256.2 ([{$^{37}$Cl}M+H]$^+$), 254.1 ([{$^{35}$Cl}M+H]$^+$).

Example 127

(S)-4-[(3-Fluoro-4-trifluoromethyl-phenylamino)-methyl]-4,5-dihydro-oxazol-2-ylamine

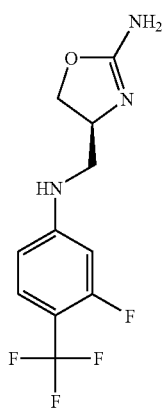

In analogy to examples 20 and 43 the title compound was prepared starting from tert-butyl (R)-(+)-4-formyl-2,2-dimethyl-3-oxazolinecarboxylate and 3-fluoro-4-trifluoromethyl-aniline. Viscous colorless oil. MS (ISP): 278.1 ([M+H]$^+$)

Example 128

(R)-4-{[(4-Fluoro-phenyl)-methyl-amino]-methyl}-4,5-dihydro-oxazol-2-ylamine

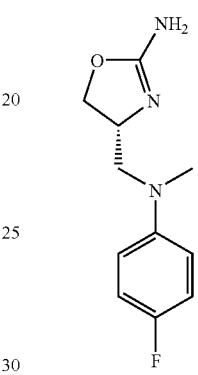

In analogy to example 3 the title compound was prepared starting from tert-butyl (S)-(−)-4-formyl-2,2-dimethyl-3-oxazolinecarboxylate and 4-fluoro-N-methylaniline. Light yellow gum. MS (ISP): 224.4 ([M+H]$^+$).

Example 129

(R)-4-{[(4-Chloro-phenyl)-isopropyl-amino]-methyl}-4,5-dihydro-oxazol-2-ylamine

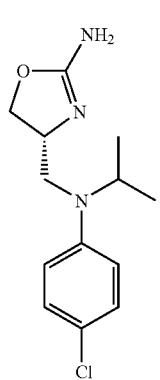

The title compound was prepared in analogy to example 2 starting from tert-butyl (S)-(−)-4-formyl-2,2-dimethyl-3-oxazolinecarboxylate and 4-chloroaniline. Colourless gum. MS (ISP): 270.2 ([{$^{37}$Cl}M+H]$^+$), 268.2 ([{$^{35}$Cl}M+H]$^+$).

Example 130

(S)-4-{[Benzyl-(4-trifluoromethyl-phenyl)-amino]-methyl}-4,5-dihydro-oxazol-2-ylamine

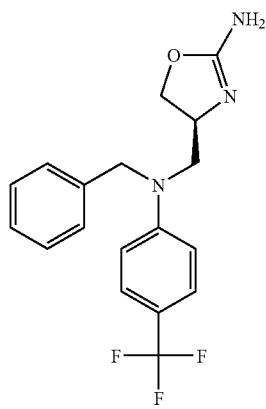

In analogy to example 20 the title compound was prepared starting from tert-butyl (R)-(+)-4-formyl-2,2-dimethyl-3-oxazolinecarboxylate and 4-trifluoromethylaniline. Viscous colorless oil. MS (ISP): 350.3 ([M+H]$^+$)

Example 131

(S)-4-{[Isopropyl-(4-trifluoromethyl-phenyl)-amino]-methyl}-4,5-dihydro-oxazol-2-ylamine

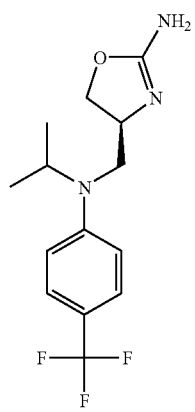

In analogy to example 2 the title compound was prepared starting from tert-butyl (R)-(+)-4-formyl-2,2-dimethyl-3-oxazolinecarboxylate and 4-trifluoromethylaniline. Viscous colorless oil. MS (ISP): 302.1 ([M+H]$^+$)

Example 132

(S)-4-[(4-Trifluoromethyl-phenylamino)-methyl]-4,5-dihydro-oxazol-2-ylamine

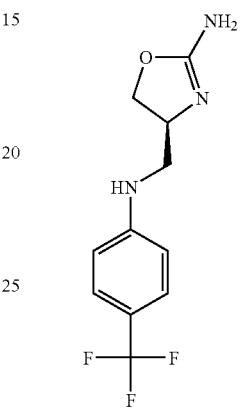

In analogy to examples 20 and 43 the title compound was prepared starting from tert-butyl (R)-(+)-4-formyl-2,2-dimethyl-3-oxazolinecarboxylate and 4-trifluoromethyl-aniline. Waxy white solid. MS (ISP): 260.1 ([M+H]$^+$)

Example 133

(S)-4-{[Ethyl-(4-trifluoromethyl-phenyl)-amino]-methyl}-4,5-dihydro-oxazol-2-ylamine

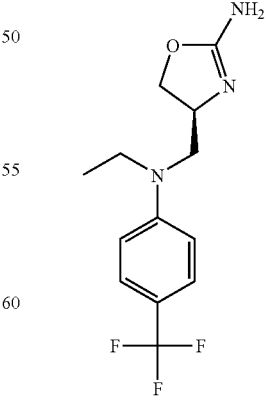

In analogy to example 1 the title compound was prepared starting from tert-butyl (R)-(+)-4-formyl-2,2-dimethyl-3-oxazolinecarboxylate and 4-trifluoromethyl-aniline. Viscous colorless oil. MS (ISP): 288.0 ([M+H]⁺)

Example 134

(S)-4-{[Methyl-(4-trifluoromethyl-phenyl)-amino]-methyl}-4,5-dihydro-oxazol-2-ylamine

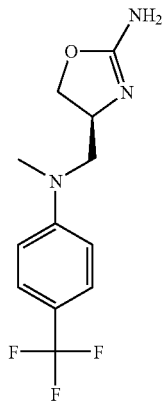

In analogy to example 30 the title compound was prepared starting from tert-butyl (R)-(+)-4-formyl-2,2-dimethyl-3-oxazolinecarboxylate and 4-trifluoromethyl-aniline. Viscous colorless oil. MS (ISP): 274.0 ([M+H]⁺)

Example 135

((S)-2-Amino-4,5-dihydro-oxazol-4-ylmethyl)-(6-chloro-pyridin-2-yl)-amine

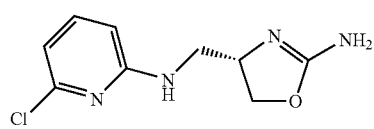

In analogy to example 123 the title compound was prepared starting from tert-butyl (R)-(+)-4-formyl-2,2-dim-ethyl-3-oxazolinecarboxylate and 2-amino-6-chloropyridine. Colorless viscous oil. MS (ISP): 227.4 ([M+H]⁺)

Example 136

(S)-4-{[(2,4-Difluoro-phenyl)-isopropyl-amino]-methyl}-4,5-dihydro-oxazol-2-ylamine

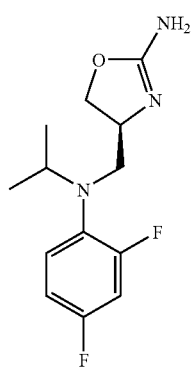

In analogy to example 2 the title compound was prepared starting from tert-butyl (R)-(+)-4-formyl-2,2-dimethyl-3-oxazolinecarboxylate and 2,4-difluoroaniline. Viscous colorless oil. MS (ISP): 270.4 ([M+H]⁺)

Example 137

(S)-4-{[Benzyl-(2,4-difluoro-phenyl)-amino]-methyl}-4,5-dihydro-oxazol-2-ylamine

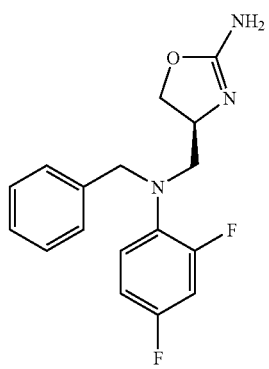

In analogy to example 2 the title compound was prepared starting from tert-butyl (R)-(+)-4-formyl-2,2-dimethyl-3-oxazolinecarboxylate and 2,4-difluoroaniline. Viscous colorless oil. MS (ISP): 318.3 ([M+H]⁺)

Example 138

(R)-4-{[(4-Fluoro-3-methoxy-phenyl)-methyl-amino]-methyl}-4,5-dihydro-oxazol-2-ylamine

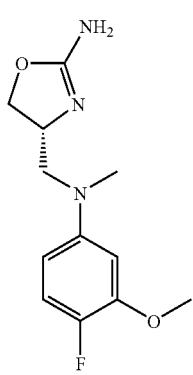

In analogy to example 30 the title compound was prepared starting from tert-butyl (S)-(−)-4-formyl-2,2-dimethyl-3-oxazolinecarboxylate and 4-fluoro-3-methoxyaniline. Off-white solid. MS (ISP): 254.1 ([M+H]⁺).

Example 139

(R)-4-{[Ethyl-(4-fluoro-3-methoxy-phenyl)-amino]-methyl}-4,5-dihydro-oxazol-2-ylamine

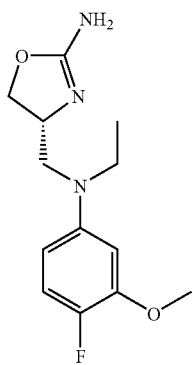

In analogy to example 1 the title compound was prepared starting from tert-butyl (S)-(−)-4-formyl-2,2-dimethyl-3-oxazolinecarboxylate and 4-fluoro-3-methoxyaniline. Light yellow gum. MS (ISP): 268.4 ([M+H]⁺).

Example 140

(R)-4-{[(4-Chloro-3-methoxy-phenyl)-methyl-amino]-methyl}-4,5-dihydro-oxazol-2-ylamine

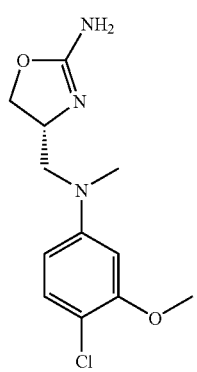

In analogy to example 30 the title compound was prepared starting from tert-butyl (S)-(−)-4-formyl-2,2-dimethyl-3-oxazolinecarboxylate and 4-chloro-3-methoxyaniline. White solid. MS (ISP): 272.3 ([{³⁷Cl}M+H]⁺), 270.3 ([{³⁵Cl}M+H]⁺).

Example 141

(R)-4-{[(4-Chloro-3-methoxy-phenyl)-ethyl-amino]-methyl}-4,5-dihydro-oxazol-2-ylamine

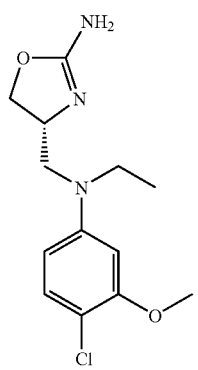

In analogy to example 1 the title compound was prepared starting from tert-butyl (S)-(−)-4-formyl-2,2-dimethyl-3-oxazolinecarboxylate and 4-chloro-3-methoxyaniline. Off-white solid. MS (ISP): 286.1 ([{$^{37}$Cl}M+H]$^+$), 284.3 ([{$^{35}$Cl}M+H]$^+$).

Example 142

(S)-4-{[(4-Chloro-benzyl)-(4-chloro-phenyl)-amino]-methyl}-4,5-dihydro-oxazol-2-ylamine

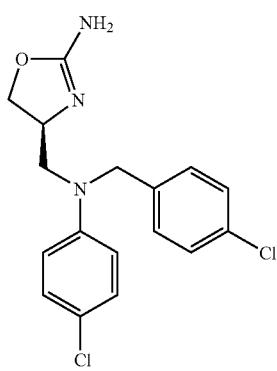

In analogy to example 20 the title compound was prepared starting from tert-butyl (R)-(+)-4-formyl-2,2-dimethyl-3-oxazolinecarboxylate, 4-chloroaniline and 4-chlorobenzaldehyde dimethyl acetal. White gum. MS (ISP): 354.1 ([{$^{37}$Cl}M+H]$^+$), 352.2 ([{$^{37}$Cl$^{35}$Cl}M+H]$^+$), 350.2 ([{$^{35}$Cl}M+H]$^+$).

Example 143

(S)-4-{[(4-Chloro-benzyl)-(4-fluoro-phenyl)-amino]-methyl}-4,5-dihydro-oxazol-2-ylamine

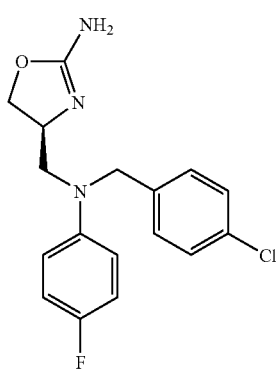

In analogy to example 20 the title compound was prepared starting from tert-butyl (R)-(+)-4-formyl-2,2-dimethyl-3-oxazolinecarboxylate, 4-fluoroaniline and 4-chlorobenzaldehyde dimethyl acetal. Colourless gum. MS (ISP): 336.2 ([{$^{37}$Cl}M+H]$^+$), 334.2 ([{$^{35}$Cl}M+H]$^+$).

Example 144

(R)-4-[(Methyl-p-tolyl-amino)-methyl]-4,5-dihydro-oxazol-2-ylamine

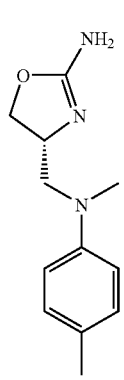

In analogy to example 3 the title compound was prepared starting from tert-butyl (S)-(−)-4-formyl-2,2-dimethyl-3-oxazolinecarboxylate and N-methyl-p-toluidine. Colourless gum. MS (ISP): 220.1 ([M+H]$^+$).

Example 145

(S)-4-{[(2,4-Difluoro-phenyl)-ethyl-amino]-methyl}-4,5-dihydro-oxazol-2-ylamine

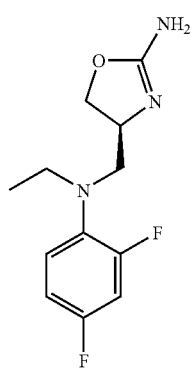

In analogy to example 1 the title compound was prepared starting from tert-butyl (R)-(+)-4-formyl-2,2-dimethyl-3-oxazolinecarboxylate and 2,4-difluoroaniline. Viscous colorless oil. MS (ISP): 256.1 ([M+H]$^+$)

Example 146

(S)-4-{[(2,4-Difluoro-phenyl)-methyl-amino]-methyl}-4,5-dihydro-oxazol-2-ylamine

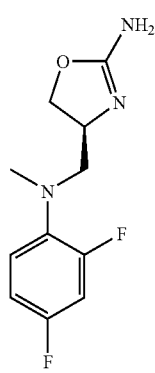

In analogy to example 30 the title compound was prepared starting from tert-butyl (R)-(+)-4-formyl-2,2-dimethyl-3-oxazolinecarboxylate and 2,4-difluoroaniline. Waxy white solid. MS (ISP): 242.1 ([M+H]$^+$)

Example 147

(R)-4-{[(4-Chloro-phenyl)-methyl-amino]-methyl}-4-methyl-4,5-dihydro-oxazol-2-ylamine

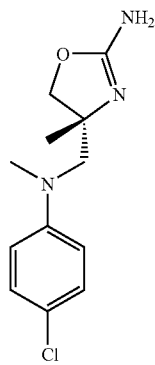

In analogy to example 109 the title compound was prepared starting from (S)-4-formyl-2,2,4-trimethyl-oxazolidine-3-carboxylic acid tert-butyl ester, 4-chloro-aniline and formaldehyde. White solid. MS (ISP): 256.1 ([{$^{37}$Cl}M+H]$^+$), 254.1 ([{$^{35}$Cl}M+H]$^+$).

Example 148

(S)-4-{[(4-Chloro-benzyl)-(3,4-dichloro-phenyl)-amino]-methyl}-4,5-dihydro-oxazol-2-ylamine

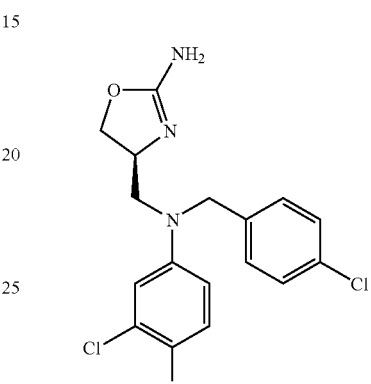

In analogy to example 20 the title compound was prepared starting from tert-butyl (R)-(+)-4-formyl-2,2-dimethyl-3-oxazolinecarboxylate, 3,4-dichloroaniline and 4-chlorobenzaldehyde dimethyl acetal. White solid. MS (ISP): 390.0 ([{$^{37}$Cl}M+H]$^+$), 388.1 ([{$^{37}$Cl$^{35}$Cl}M+H]$^+$), 386.0 ([{$^{37}$Cl$^{35}$Cl}M+H]$^+$), 384.1 ([{$^{35}$Cl}M+H]$^+$).

Example 149

(S)-4-{[(4-Bromo-phenyl)-(4-chloro-benzyl)-amino]-methyl}-4,5-dihydro-oxazol-2-ylamine

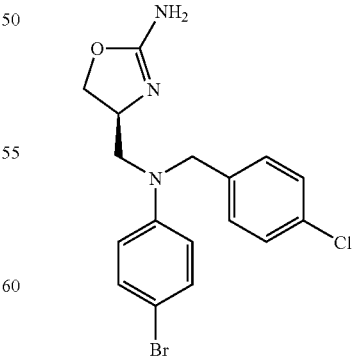

In analogy to example 20 the title compound was prepared starting from tert-butyl (R)-(+)-4-formyl-2,2-dimethyl-3-oxazolinecarboxylate, 4-bromoaniline and 4-chlorobenzaldehyde dimethyl acetal. White solid. MS (ISP): 398.0 ([{$^{37}$Cl$^{81}$Br}M+H]$^+$), 396.0 ([{$^{37}$Cl$^{79}$Br, $^{35}$Cl$^{81}$Br}M+H]$^+$), 394.0 ([{$^{35}$Cl$^{79}$Cl}M+H]$^+$).

Example 150

(S)-4-{[(4-Chloro-phenyl)-methyl-amino]-methyl}-4-methyl-4,5-dihydro-oxazol-2-ylamine

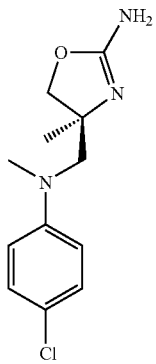

In analogy to example 109 the title compound was prepared starting from (R)-4-formyl-2,2,4-trimethyl-oxazolidine-3-carboxylic acid tert-butyl ester, 4-chloro-aniline and formaldehyde. White solid. MS (ISP): 256.1 ([{$^{37}$Cl}M+H]$^+$), 254.1 ([{$^{35}$Cl}M+H]$^+$).

Example 151

((S)-2-Amino-4,5-dihydro-oxazol-4-ylmethyl)-(6-chloro-pyridin-2-yl)-ethyl-amine a) (S)-4-[(6-Chloro-pyridin-2-ylamino)-methyl]-2,2-dimethyl-oxazolidine-3-carboxylic acid tert-butyl ester

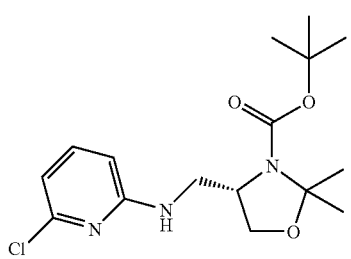

In analogy to example 123.a tert-butyl (R)-(+)-4-formyl-2,2-dimethyl-3-oxazolinecarboxylate was reacted with 2-amino-6-chloropyridin. Light yellow solid. MS (ISP): 342.3 ([M+H]$^+$)

b) (((S)-4-{[(6-Chloro-pyridin-2-yl)-ethyl-amino]-methyl}-2,2-dimethyl-oxazolidine-3-carboxylic acid tert-butyl ester

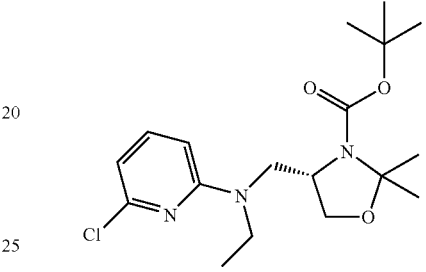

To a stirred solution of (S)-4-[(6-chloro-pyridin-2-ylamino)-methyl]-2,2-dimethyl-oxazo-lidine-3-carboxylic acid tert-butyl ester (528 mg) at r.t. in 1,2-dichloroethane (20 ml) under an argon atmosphere were added molecular sieves 4 A (~2 g) and acetaldehyde (044 ml). After 30 min stirring at r.t., sodium triacetoxyborohydride (1.02 g) was added, followed by acetic acid (0.13 ml). The mixture was stirred for at r.t. over night, then diluted with CH$_2$Cl$_2$ and washed with sat. aq. Na$_2$CO$_3$. The biphasic mixture was filtered. The aqueous phase of the filtrate was back extracted with CH$_2$Cl$_2$. The combined organics were washed with brine, dried over MgSO$_4$, filtered and concentrated. The crude product was purified by column chromatography (SiO$_2$; gradient:cyclohexane->cyclohexane/EtOAc 85:15) to give (S)-4-{[(6-chloro-pyridin-2-yl)-ethyl-amino]-methyl}-2,2-dimethyl-oxazolidine-3-carboxylic acid tert-butyl ester (244 mg, 43%) as viscous yellow oil. MS (ISP): 370.3 ([M+H]$^+$)

c) ((S)-2-Amino-4,5-dihydro-oxazol-4-ylmethyl)-(6-chloro-pyridin-2-yl)-ethyl-amine

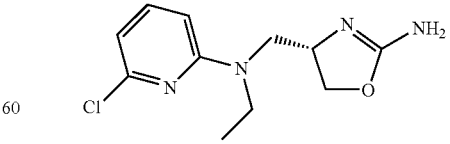

In analogy to example 1.c and 1.d (S)-4-{[(6-chloro-pyridin-2-yl)-ethyl-amino]-methyl}-2,2-dimethyl-oxazolidine- 3-carboxylic acid tert-butyl ester was converted to the title compound. Light yellow viscous oil. MS (ISP): 255.1 ([M+H]$^+$)

Example 152

(S)-4-[(2,4-Difluoro-phenylamino)-methyl]-4,5-dihydro-oxazol-2-ylamine

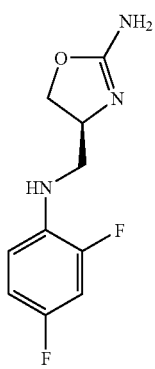

In analogy to examples 20 and 43 the title compound was prepared starting from tert-butyl (R)-(+)-4-formyl-2,2-dimethyl-3-oxazolinecarboxylate and 2,4-difluoroaniline. Waxy colorless solid. MS (ISP): 228.1 ([M+H]$^+$)

Example 153

(S)-4-{[(3,5-Dichloro-phenyl)-isopropyl-amino]-methyl}-4,5-dihydro-oxazol-2-ylamine

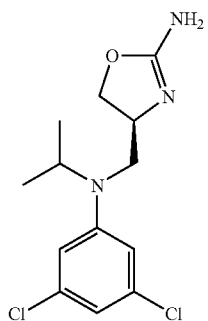

In analogy to example 2 the title compound was prepared starting from tert-butyl (R)-(+)-4-formyl-2,2-dimethyl-3-ox-azolinecarboxylate and 3,5-dichloroaniline. Viscous colorless oil. MS (ISP): 302.1 ([M+H]$^+$)

Example 154

(S)-4-{[Benzyl-(3,5-dichloro-phenyl)-amino]-methyl}-4,5-dihydro-oxazol-2-ylamine

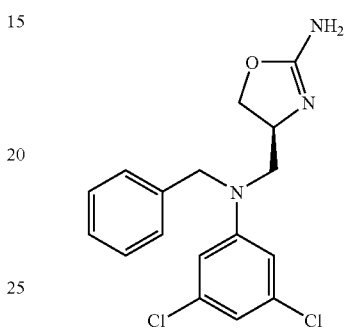

In analogy to example 20 the title compound was prepared starting from tert-butyl (R)-(+)-4-formyl-2,2-dimethyl-3-oxazolinecarboxylate and 3,5-dichloroaniline. Viscous colorless oil. MS (ISP): 350.1 ([M+H]$^+$)

Example 155

(S)-4-{[Benzyl-(4-chloro-3-methoxy-phenyl)-amino]-methyl}-4,5-dihydro-oxazol-2-ylamine

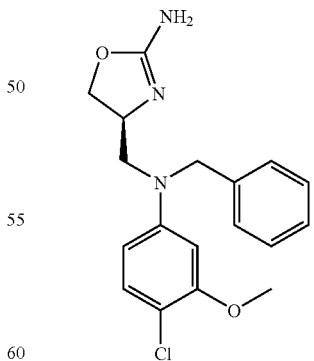

In analogy to example 20 the title compound was prepared starting from tert-butyl (R)-(+)-4-formyl-2,2-dimethyl-3-oxazolinecarboxylate, 4-chloro-3-methoxyaniline and benzaldehyde dimethyl acetal. White solid. MS (ISP): 348.1 ([{$^{37}$Cl}M+H]$^+$), 346.0 ([{$^{35}$Cl}M+H]$^+$).

Example 156

(S)-4-{[(4-Chloro-benzyl)-(4-chloro-3-methoxy-phenyl)-amino]-methyl}-4,5-dihydro-oxazol-2-ylamine

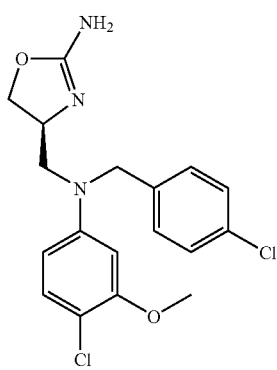

In analogy to example 20 the title compound was prepared starting from tert-butyl (R)-(+)-4-formyl-2,2-dimethyl-3-oxazolinecarboxylate, 4-chloro-3-methoxyaniline and 4-chlorobenzaldehyde dimethyl acetal. Colourless gum. MS (ISP): 384.2 ([{$^{37}$Cl}M+H]$^+$), 382.3 ([{$^{37}$Cl$^{35}$Cl}M+H]$^+$), 380.2 ([{$^{35}$Cl}M+H]$^+$).

Example 157

(R)-4-{[(3,4-Dichloro-phenyl)-methyl-amino]-methyl}-4,5-dihydro-oxazol-2-ylamine

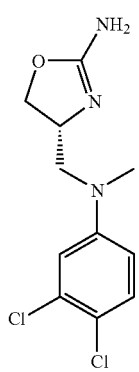

In analogy to example 30 the title compound was prepared starting from tert-butyl (S)-(−)-4-formyl-2,2-dimethyl-3-ox-azolinecarboxylate and 3,4-dichloroaniline. Colourless gum. MS (ISP): 278.1 ([{$^{37}$Cl}M+H]$^+$), 276.1 ([{$^{37}$Cl$^{35}$Cl}M+H]$^+$), 274.1 ([{$^{35}$Cl}M+H]$^+$).

Example 158

(R)-4-{[(3,4-Dichloro-phenyl)-ethyl-amino]-methyl}-4,5-dihydro-oxazol-2-ylamine

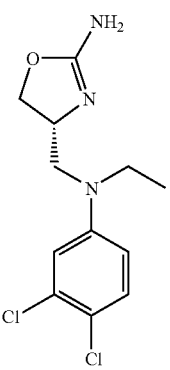

In analogy to example 1 the title compound was prepared starting from tert-butyl (S)-(−)-4-formyl-2,2-dimethyl-3-ox-azolinecarboxylate and 3,4-dichloroaniline. Colourless gum. MS (ISP): 292.1 ([{$^{37}$Cl}M+H]$^+$), 290.0 ([{$^{37}$Cl$^{35}$Cl}M+H]$^+$), 288.1 ([{$^{35}$Cl}M+H]$^+$).

Example 159

(R)-4-{[(3,4-Dichloro-phenyl)-isopropyl-amino]-methyl}-4,5-dihydro-oxazol-2-ylamine

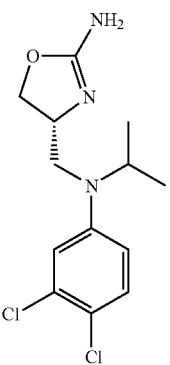

The title compound was prepared in analogy to example 2 starting from tert-butyl (S)-(−)-4-formyl-2,2-dimethyl-3-oxazolinecarboxylate and 3,4-dichloroaniline. Colourless gum. MS (ISP): 306.1 ([{$^{37}$Cl}M+H]$^+$), 304.1 ([{$^{37}$Cl$^{35}$Cl}M+H]$^+$), 302.1 ([{$^{35}$Cl}M+H]$^+$).

Example 160

(S)-4-{[(3,5-Dichloro-phenyl)-methyl-amino]-methyl}-4,5-dihydro-oxazol-2-ylamine

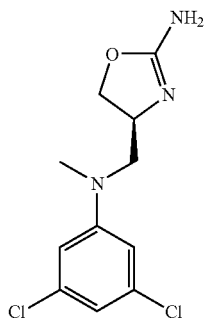

In analogy to example 30 the title compound was prepared starting from tert-butyl (R)-(+)-4-formyl-2,2-dimethyl-3-oxazolinecarboxylate and 3,5-dichloroaniline. White solid. MS (ISP): 274.0 ([M+H]$^+$)

Example 161

((S)-2-Amino-4,5-dihydro-oxazol-4-ylmethyl)-(6-trifluoromethyl-pyridin-2-yl)-amine

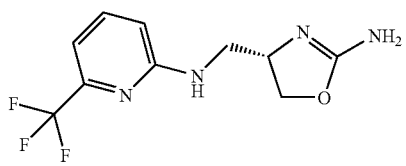

In analogy to example 123 the title compound was prepared starting from tert-butyl (R)-(+)-4-formyl-2,2-dimethyl-3-oxazolinecarboxylate and 2-amino-6-trifluoromethyl-pyridine. Colorless viscous oil. Light yellow viscous oil. MS (ISP): 261.5 ([M+H]$^+$)

Example 162

(R)-4-[(Methyl-naphthalen-2-yl-amino)-methyl]-4,5-dihydro-oxazol-2-ylamine

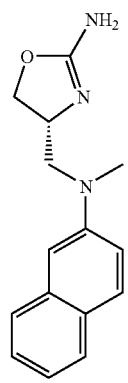

In analogy to example 30 the title compound was prepared starting from tert-butyl (S)-(−)-4-formyl-2,2-dimethyl-3-oxazolinecarboxylate and 2-aminonaphthalene. White solid. MS (ISP): 256.3 ([M+H]$^+$).

Example 163

(R)-4-[(Ethyl-naphthalen-2-yl-amino)-methyl]-4,5-dihydro-oxazol-2-ylamine

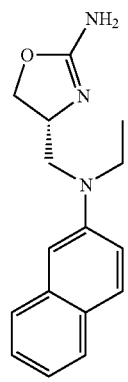

In analogy to example 1 the title compound was prepared starting from tert-butyl (S)-(−)-4-formyl-2,2-dimethyl-3-oxazolinecarboxylate and 2-aminonaphthalene. Off-white solid. MS (ISP): 270.4 ([M+H]⁺).

Example 164

(R)-4-[{Benzyl-(3-fluoro-4-trifluoromethyl-phenyl)-amino]-methyl}-4,5-dihydro-oxazol-2-ylamine

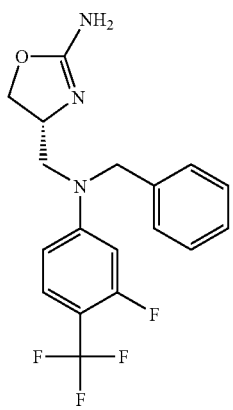

In analogy to example 20 the title compound was prepared starting from tert-butyl (S)-(−)-4-formyl-2,2-dimethyl-3-oxazolinecarboxylate, 4-amino-2-fluorobenzonitrile and benzaldehyde dimethyl acetal. Colourless gum. MS (ISP): 368.1 ([M+H]⁺).

Example 165

(S)-4-{[(3,5-Dichloro-phenyl)-ethyl-amino]-methyl}-4,5-dihydro-oxazol-2-ylamine

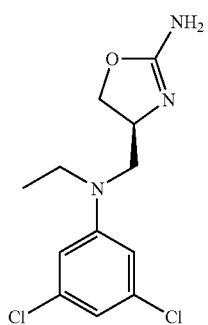

In analogy to example 1 the title compound was prepared starting from tert-butyl (R)-(+)-4-formyl-2,2-dimethyl-3-oxazolinecarboxylate and 3,5-dichloroaniline. Light yellow viscous oil. MS (ISP): 288.0 ([M+H]⁺)

Example 166

(R)-4-{[Ethyl-(3-fluoro-4-trifluoromethyl-phenyl)-amino]-methyl}-4,5-dihydro-oxazol-2-ylamine

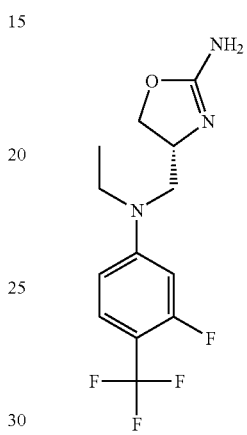

In analogy to example 1 the title compound was prepared starting from tert-butyl (S)-(−)-4-formyl-2,2-dimethyl-3-oxazolinecarboxylate and 3-fluoro-4-trifluoromethylaniline. Waxy white solid. MS (ISP): 306.0 ([M+H]⁺)

Example 167

(R)-4-{[Ethyl-(3-fluoro-5-trifluoromethyl-phenyl)-amino]-methyl}-4,5-dihydro-oxazol-2-ylamine

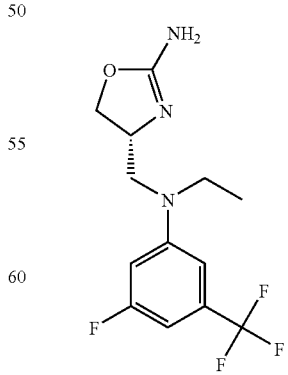

In analogy to example 1 the title compound was prepared starting from tert-butyl (S)-(−)-4-formyl-2,2-dimethyl-3-oxazolinecarboxylate and 3-amino-5-fluorobenzotrifluoride. Colourless gum. MS (ISP): 306.3 ([M+H]+).

Example 168

(R)-4-{[Isopropyl-(4-trifluoromethyl-phenyl)-amino]-methyl}-4,5-dihydro-oxazol-2-ylamine

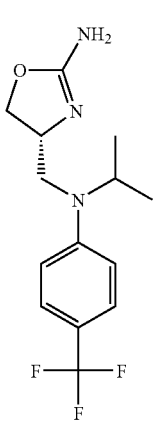

Chiral

The title compound was prepared in analogy to example 2 starting from tert-butyl (S)-(−)-4-formyl-2,2-dimethyl-3-oxazolinecarboxylate and 4-amino-benzotrifluoride. Colourless gum. MS (ISP): 302.4 ([M+H]+).

Example 169

(R)-4-{[(4-Chloro-2-fluoro-phenyl)-ethyl-amino]-methyl}-4,5-dihydro-oxazol-2-ylamine

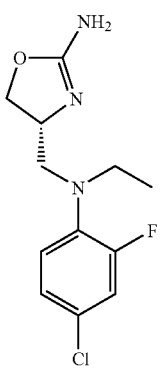

In analogy to example 1 the title compound was prepared starting from tert-butyl (S)-(−)-4-formyl-2,2-dimethyl-3-oxazolinecarboxylate and 4-chloro-2-fluoro-aniline. Colourless gum. MS (ISP): 274.2 ([{37Cl}M+H]+), 272.3 ([{35Cl}M+H]+).

Example 170

(R)-4-{[(4-Bromo-phenyl)-(4-chloro-benzyl)-amino]-methyl}-4,5-dihydro-oxazol-2-ylamine

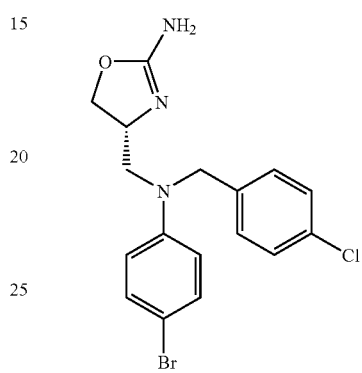

In analogy to example 20 the title compound was prepared starting from tert-butyl (S)-(−)-4-formyl-2,2-dimethyl-3-oxazolinecarboxylate, 4-bromoaniline and 4-chlorobenzaldehyde dimethyl acetal. Yellow gum. MS (ISP): 398.1 ([{37Cl81Br}M+H]+), 396.0 ([{37Cl79Br, 35Cl81Br}M+H]+), 394.0 ([{35Cl79Cl}M+H]+).

Example 171

(R)-4-{[(4-Chloro-benzyl)-(3,4-dichloro-phenyl)-amino]-methyl}-4,5-dihydro-oxazol-2-ylamine

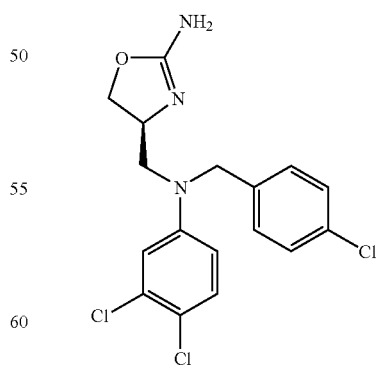

In analogy to example 20 the title compound was prepared starting from tert-butyl (S)-(−)-4-formyl-2,2-dimethyl-3-oxazolinecarboxylate, 3,4-dichloroaniline and 4-chlorobenzaldehyde dimethyl acetal. White solid. MS (ISP): 390.0

Example 172

(S)-4-{[(4-Bromo-benzyl)-(4-bromo-phenyl)-amino]-methyl}-4,5-dihydro-oxazol-2-ylamine

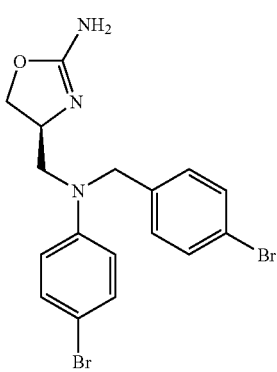

In analogy to example 20 the title compound was prepared starting from tert-butyl (R)-(+)-4-formyl-2,2-dimethyl-3-oxazolinecarboxylate, 4-bromoaniline and 4-bromobenzaldehyde dimethyl acetal. Colourless gum. MS (ISP): 442.0 ([{$^{81}$Br}M+H]$^+$), 440.1 ([{$^{81}$Br$^{79}$Br}M+H]$^+$), 438.0 ([{$^{79}$Br}M+H]$^+$).

Example 173

(S)-4-{[(4-Bromo-benzyl)-(4-chloro-phenyl)-amino]-methyl}-4,5-dihydro-oxazol-2-ylamine

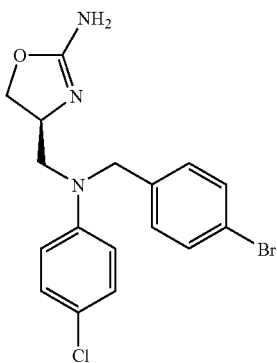

In analogy to example 20 the title compound was prepared starting from tert-butyl (R)-(+)-4-formyl-2,2-dimethyl-3-oxazolinecarboxylate, 4-chloroaniline and 4-bromobenzaldehyde dimethyl acetal. Colourless gum. MS (ISP): 398.1 ([{$^{81}$Br$^{37}$Cl}M+H]$^+$), 395.9 ([{$^{79}$Br$^{37}$Cl, $^{81}$Br$^{35}$Cl}M+H]$^+$), 394.0 ([{$^{79}$Cl$^{35}$Cl}M+H]$^+$).

Example 174

(S)-4-{[Benzyl-(2-methyl-4-trifluoromethyl-phenyl)-amino]-methyl}-4,5-dihydro-oxazol-2-ylamine

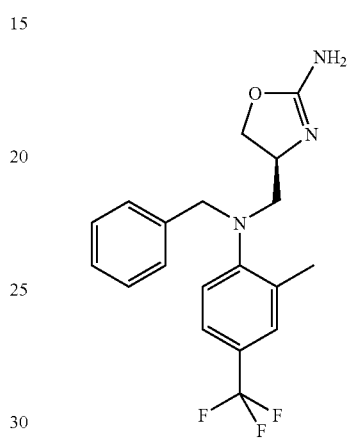

In analogy to example 20 the title compound was prepared starting from tert-butyl (R)-(+)-4-formyl-2,2-dimethyl-3-oxazolinecarboxylate and 2-methyl-4-trifluoromethylaniline. Viscous colorless oil. MS (ISP): 364.3 ([M+H]$^+$)

Example 175

(S)-4-{[Ethyl-(2-methyl-4-trifluoromethyl-phenyl)-amino]-methyl}-4,5-dihydro-oxazol-2-ylamine

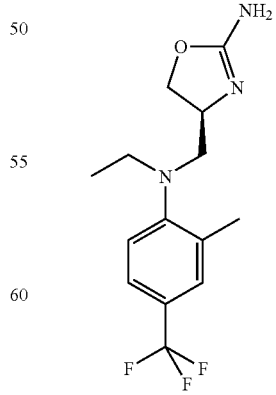

In analogy to example 1 the title compound was prepared starting from tert-butyl (R)-(+)-4-formyl-2,2-dimethyl-3-oxazolinecarboxylate and 2-methyl-4-trifluoromethylaniline. Viscous colorless oil. MS (ISP): 302.4 ([M+H]+)

Example 176

(S)-4-[(2-Methyl-4-trifluoromethyl-phenylamino)-methyl]-4,5-dihydro-oxazol-2-ylamine

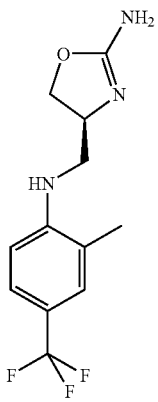

In analogy to examples 20 and 43 the title compound was prepared starting from tert-butyl (R)-(+)-4-formyl-2,2-dimethyl-3-oxazolinecarboxylate and 2-methyl-4-trifluoromethylaniline. Viscous colorless oil. MS (ISP): 274.4 ([M+H]+)

Example 177

(S)-4-{[Isopropyl-(2-methyl-4-trifluoromethyl-phenyl)-amino]-methyl}-4,5-dihydro-oxazol-2-ylamine

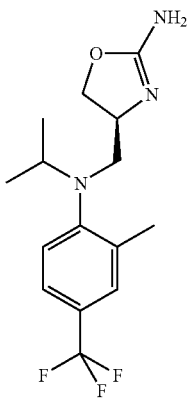

In analogy to example 2 the title compound was prepared starting from tert-butyl (R)-(+)-4-formyl-2,2-dimethyl-3-ox-azolinecarboxylate and 2-methyl-4-trifluoromethylaniline. Viscous colorless oil. MS (ISP): 316.4 ([M+H]+)

Example 178

((S)-2-Amino-4,5-dihydro-oxazol-4-ylmethyl)-ethyl-(6-trifluoromethyl-pyridin-3-yl)-amine

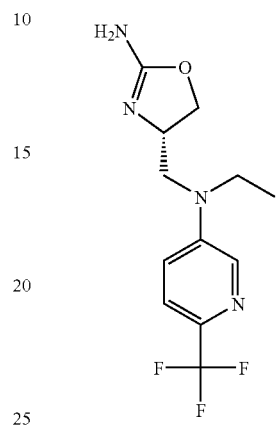

a) (R)-2,2-Dimethyl-4-(6-trifluoromethyl-pyridin-3-ylcarbamoyl)-oxazolidine-3-carboxylic acid tert-butyl ester To a solution of (4S)-3-(tert.-butoxycarbonyl)-2,2-dimethyl-1,3-oxazolidine-3-carboxylic acid (0.49 g, 2 mmol) in dichloromethane (6 ml) was added 3-amino-6-(trifluoromethyl)pyridine (0.324 mg, 2 mmol), bis(2-oxo-3-oxazolidinyl)phosphinic chloride 0.764 g, 3 mmol) and N,N-diisopropylethylamine (0.388 g, 3 mmol). The mixture was stirred overnight at room temperature. For workup sodium bicarbonate solution (5 ml) was added and the mixture was extracted with dichloromethane twice. The combined organic layers were dried (MgSO4) and filtered. After removal of the solvent the residue was purified by column chromatography (SiO2, heptane/EtOAc=4:1) to yield a white solid (0.36 g, 46%), MS (ISP): 390.3 ([M+H]+).

b) (R)-4-[Ethyl-(6-trifluoromethyl-pyridin-3-yl)-carbamoyl]-2,2-dimethyl-oxazolidine-3-carboxylic acid tert-butyl ester To a stirred solution of (R)-2,2-dimethyl-4-(6-trifluoromethyl-pyridin-3-ylcarbamoyl)-oxazolidine-3-carboxylic acid tert-butyl ester (0.20 g, 0.51 mmol) in dimethylsulfoxide (4 ml) under an argon atmosphere was added sodium hydride (0.028 g, 0.59 mmol) and the mixture was stirred for 20 min. Iodoethane (0.05 ml, 0.61 mmol) was added and the mixture was stirred overnight at room temperature. Water (20 ml) was added and the mixture was extracted three times with ethyl acetate. The combined organic layers were dried (MgSO$_4$) and filtered. After removal of the solvent the residue was purified by column chromatography (SiO2, heptane/EtOAc=1:1) to yield a light yellow oil (0.15 g, 70%), MS (ISP): 418.2 ([M+H]+).

c) (S)-2-Amino-3-[ethyl-(6-trifluoromethyl-pyridin-3-yl)-amino]-propan-1-ol

To a stirred solution of (S)-4-[(isopropyl-phenyl-amino)-methyl]-2,2-dimethyl-oxazolidine-3-carboxylic acid tert-butyl ester (0.15 g, 0.36 mmol) in tetrahydrofurane (4 ml) under an argon atmosphere was added borane-terahydrofurane complex (1M solution, 1.8 ml, 1.8 mmol). The mixture was stirred at 60° C. for 2 hours. After cooling to room temperature hydrochloric acid (4N in water, 2 ml) was added carefully and the mixture was stirred again at 60° C. for 2 hours. After cooling aqueous sodium hydroxide solution (1M) was added until basic pH and the mixture was extracted three times with ethyl acetate. The combined organic layers were dried (MgSO$_4$) and filtered. After removal of the solvent the residue was purified by column chromatography (SiO$_2$, dichloromethane/MeOH=9:1) to yield a white solid (0.04 g, 42%), MS (ISP): 264.2 ([M+H]$^+$).

d) ((S)-2-Amino-4,5-dihydro-oxazol-4-ylmethyl)-ethyl-(6-trifluoromethyl-pyridin-3-yl)-amine To a stirred mixture of (S)-2-amino-3-[ethyl-(6-trifluoromethyl-pyridin-3-yl)-amino]-propan-1-ol (0.04 g, 0.15 mmol) and K$_2$CO$_3$ (0.025 g, 0.18 mmol) in THF (2 ml) under an argon atmosphere was added a solution of cyanogen bromide (0.025 g, 0.18 mmol) in THF (1 ml). The mixture was stirred for 1 hour, then ethylacetate and water were added. The aqueous phase was back extracted with EtOAc. The combined organics were washed with brine, dried over MgSO$_4$, filtered and concentrated. The crude product was purified by column chromatography (SiO2, EtOAc/MeOH=9:1) to give the title compound as white solid (0.02 g, 46%), MS (ISP): 289.0 ([M+H]$^+$).

Example 179

((S)-2-Amino-4,5-dihydro-oxazol-4-ylmethyl)-(6-methoxy-pyridin-3-yl)-methyl-amine

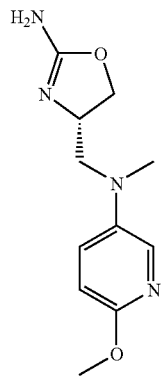

The title compound, MS (ISP): 236.9 ((M+H)$^+$) was obtained in comparable yield analogous to the procedure described for Example 178 using 5-amino-2-methoxypyridine instead of 3-amino-6-(trifluoromethyl)pyridine in step a) and iodomethane instead of iodoethane in step b).

Example 180

(S)-4-{[(4-Chloro-benzyl)-(3-fluoro-4-trifluoromethyl-phenyl)-amino]-methyl}-4,5-dihydro-oxazol-2-ylamine

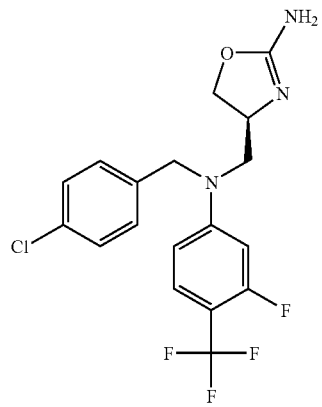

In analogy to example 20 the title compound was prepared starting from tert-butyl (R)-(+)-4-formyl-2,2-dimethyl-3-oxazolinecarboxylate and 3-fluoro-4-trifluoromethylaniline, using 4-chlorobenzaldehyde dimethylacetal in the second reaction step. Viscous colorless oil. MS (ISP): 401.2 ([M+H]$^+$)

Example 181

((S)-2-Amino-4,5-dihydro-oxazol-4-ylmethyl)-ethyl-(2-trifluoromethyl-pyrimidin-4-yl)-amine

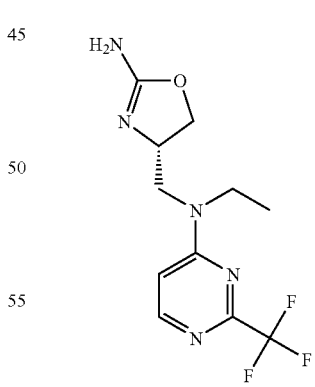

a) (S)-4-Ethylaminomethyl-2,2-dimethyl-oxazolidine-3-carboxylic acid tert-butyl ester To a solution of tert-butyl (R)-(+)-4-formyl-2,2-dimethyl-3-oxazolinecarboxylate (2.29 g, 10 mmol) in methanol (10 ml) were added a solution of ethylamine in methanol (2M, 15 ml, 30 mmol) and molecular sieves 4 Å. After stirring at room temperature for 90 min molecular sieves were filtered off and palladium on charcoal was added (0.3 g). The mixture was hydrogenated overnight at atmospheric pressure and room temperature. The catalyst was filtered off, the filtrate was evaporated and the residue purified by column chromatography (SiO$_2$, EtOAc/MeOH=95:5) to yield a colourless liquid (2.45 g, 95%), MS (ISP): 259.0 ([M+H]$^+$).

b) (S)-4-{[Ethyl-(2-trifluoromethyl-pyrimidin-4-yl)-amino]-methyl}-2,2-dimethyl-oxazolidine-3-carboxylic acid tert-butyl ester A solution of (S)-4-ethylaminomethyl-2,2-dimethyl-oxazolidine-3-carboxylic acid tert-butyl ester (0.310 g, 1.2 mmol), 4-chloro-2-(trifluoromethyl)pyrimidine (0.183 g; 1.0 mmol) and N,N-diisopropyl ethyl amine (0.34 ml, 2.0 mmol) in isopropanol (3 ml) was heated in a sealed vessel in a microwave oven for 30 min at 180° C. Ethyl acetate (20 ml) and silicagel (1 g) was added and the mixture was evaporated. The residue was purified by flash chromatography, column: Isolute® Flash-NH$_2$ (Separtis); eluent: EtOAc/MeOH=95:5) to yield a light yellow oil, (0.362 g, 90%); MS (ISP): 405.5 ((M+H)$^+$).

c) (S)-2-Amino-3-[ethyl-(2-trifluoromethyl-pyrimidin-4-yl)-amino]-propan-1-ol (S)-4-{[Ethyl-(2-trifluoromethyl-pyrimidin-4-yl)-amino]-methyl}-2,2-dimethyl-oxazolidine-3-carboxylic acid tert-butyl ester (0.339 g, 0.84 mmol) was dissolved in dioxane (6 ml), aqueous hydrochloric acid (4N, 6 ml) was added and the mixture was stirred at 60° C. for 3 hours. The solvent was evaporated and the residue was dissolved in dichloromethane. A solution of ammonia in methanol (2N, 2 ml) was added and the mixture was evaporated over Isolute® Flash-NH$_2$ silicagel. Chromatography (column: Isolute® Flash-NH$_2$ from Separtis; eluent: ethyl acetate/MeOH=95:5) yielded a light yellow liquid, (0.19 g, 86%); MS (ISP): 265.3 ((M+H)$^+$).

d) ((S)-2-Amino-4,5-dihydro-oxazol-4-ylmethyl)-ethyl-(2-trifluoromethyl-pyrimidin-4-yl)-amine To a stirred mixture of (S)-2-amino-3-[ethyl-(2-trifluoromethyl-pyrimidin-4-yl)-amino]-propan-1-ol (0.185 g, 0.7 mmol) and K$_2$CO$_3$ (0.145 g, 1.05 mmol) in THF (5 ml) under an argon atmosphere was added a solution of cyanogen bromide (0.111 g, 1.05 mmol) in THF (1 ml). The mixture was stirred for 2 hours, then methanol (1 ml) was added. The solution was evaporated over Isolute® Flash-NH$_2$ silicagel. Chromatography (column: Isolute® Flash-NH$_2$ from Separtis; eluent: ethyl acetate/MeOH=95:5) yielded the title compound as light yellow oil, (0.084 g, 42%); MS (ISP): 290.0 ((M+H)$^+$).

Example 182

((S)-2-Amino-4,5-dihydro-oxazol-4-ylmethyl)-ethyl-(4-trifluoromethyl-pyrimidin-2-yl)-amine

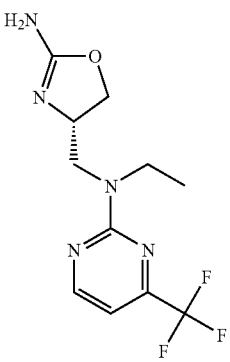

The title compound, MS (ISP): 290.0 ((M+H)$^+$) was obtained in comparable yield analogous to the procedure described for Example 181 using 2-chloro-4-(trifluoromethyl)pyrimidine instead of 4-chloro-2-(trifluoromethyl)pyrimidine in step b).

Example 183

((S)-2-Amino-4,5-dihydro-oxazol-4-ylmethyl)-methyl-(4-trifluoromethyl-pyrimidin-2-yl)-amine

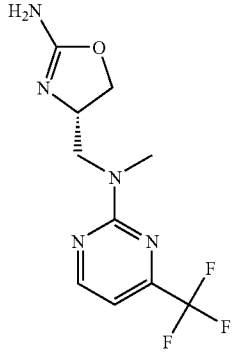

The title compound, MS (ISP): 276.0 ((M+H)$^+$) was obtained in comparable yield analogous to the procedure described for Example 181 using methylamine instead of ethylamine in step a) and 2-chloro-4-(trifluoromethyl)pyrimidine instead of 4-chloro-2-(trifluoromethyl)pyrimidine in step b).

HPLC Conditions:

| Solid phase: Zorbax XDB C18, 150 × 4.6 mm, 5 μm  Eluent: [A]: 50 mmol ammonium formiate/formic acid pH = 3, [B]: MeCN, [C]: water with 5% of B | | | | |
|---|---|---|---|---|
| Gradient: | min | [A] | [B] | [C] |
| | 0 | 10 | 10 | 80 |
| | 2 | 10 | 10 | 80 |
| | 10 | 10 | 70 | 20 post time: 3 min |
| Detection: 250 nm | | | | |
| Oven: 25° C. | | | | |
| Flow: 1.2 ml/min | | Retention time: Starting Material: 6.8 min, Product 6.5 min | | |

The invention claimed is:

1. A compound of formula I

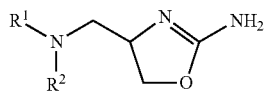

wherein
R¹ is aryl or heteroaryl, wherein the aryl and heteroaryl groups are unsubstituted or substituted by one to three substituents, selected from the group consisting of cycloalkyl, phenyl, phenyloxy, benzyl, benzyloxy, halogen, lower alkyl, lower alkoxy, heteroaryl, piperidin-1-yl, and lower alkyl substituted by halogen, or is aryl or heteroaryl wherein at least one hydrogen atom is replaced by deuterium or tritium;
R² is hydrogen, lower alkyl or benzyl unsubstituted or substituted by alkoxy or halogen; and
R³ is hydrogen or lower alkyl
or a pharmaceutically suitable acid addition salt thereof.

2. The compound of claim 1, wherein R¹ is unsubstituted phenyl and R² is lower alkyl.

3. The compound of claim 2, selected from the group consisting of
(R)-4-[(ethyl-phenyl-amino)-methyl]-4,5-dihydro-oxazol-2-ylamine,
(S)-4-[(ethyl-phenyl-amino)-methyl]-4,5-dihydro-oxazol-2-ylamine, and
(S)-4-[(methyl-phenyl-amino)-methyl]-4,5-dihydro-oxazol-2-ylamine.

4. The compound of claim 1, wherein R¹ is phenyl substituted by halogen and R² is lower alkyl.

5. The compound of claim 4, selected from the group consisting of
(S)-4-{[(3,4-dichloro-phenyl)-methyl-amino]-methyl}-4,5-dihydro-oxazol-2-ylamine,
(S)-4-{[(4-chloro-phenyl)-ethyl-amino]-methyl}-4,5-dihydro-oxazol-2-ylamine,
(S)-4-{[(3,4-dichloro-phenyl)-isopropyl-amino]-methyl}-4,5-dihydro-oxazol-2-ylamine,
(S)-4-{[(4-bromo-phenyl)-methyl-amino]-methyl}-4,5-dihydro-oxazol-2-ylamine,
(S)-4-{[(4-bromo-phenyl)-ethyl-amino]-methyl}-4,5-dihydro-oxazol-2-ylamine,
(S)-4-{[(3,4-dichloro-phenyl)-ethyl-amino]-methyl}-4,5-dihydro-oxazol-2-ylamine,
(S)-4-{[(3-bromo-phenyl)-methyl-amino]-methyl}-4,5-dihydro-oxazol-2-ylamine,
(S)-4-{[(3-bromo-phenyl)-ethyl-amino]-methyl}-4,5-dihydro-oxazol-2-ylamine,
(S)-4-{[(3-chloro-phenyl)-ethyl-amino]-methyl}-4,5-dihydro-oxazol-2-ylamine,
(S)-4-{[(4-chloro-2-fluoro-phenyl)-ethyl-amino]-methyl}-4,5-dihydro-oxazol-2-ylamine,
(S)-4-{[(4-chloro-2-fluoro-phenyl)-methyl-amino]-methyl}-4,5-dihydro-oxazol-2-ylamine,
(S)-4-{[ethyl-(2-fluoro-phenyl)-amino]-methyl}-4,5-dihydro-oxazol-2-ylamine,
(S)-4-{[(2-chloro-phenyl)-ethyl-amino]-methyl}-4,5-dihydro-oxazol-2-ylamine,
(R)-4-{[(4-chloro-phenyl)-methyl-amino]-methyl}-4,5-dihydro-oxazol-2-ylamine,
(R)-4-{[(4-chloro-phenyl)-ethyl-amino]-methyl}-4,5-dihydro-oxazol-2-ylamine,
(R)-4-{[(4-fluoro-phenyl)-methyl-amino]-methyl}-4,5-dihydro-oxazol-2-ylamine,
(R)-4-{[(4-chloro-phenyl)-isopropyl-amino]-methyl}-4,5-dihydro-oxazol-2-ylamine,
(S)-4-{[(2,4-difluoro-phenyl)-ethyl-amino]-methyl}-4,5-dihydro-oxazol-2-ylamine,
(S)-4-{[(2,4-difluoro-phenyl)-methyl-amino]-methyl}-4,5-dihydro-oxazol-2-ylamine,
(R)-4-{[(3,4-dichloro-phenyl)-methyl-amino]-methyl}-4,5-dihydro-oxazol-2-ylamine,
(R)-4-{[(3,4-dichloro-phenyl)-ethyl-amino]-methyl}-4,5-dihydro-oxazol-2-ylamine,
(R)-4-{[(3,4-dichloro-phenyl)-isopropyl-amino]-methyl}-4,5-dihydro-oxazol-2-ylamine,
(S)-4-{[(3,5-dichloro-phenyl)-methyl-amino]-methyl}-4,5-dihydro-oxazol-2-ylamine, and
(S)-4-{[(3,5-dichloro-phenyl)-ethyl-amino]-methyl}-4,5-dihydro-oxazol-2-ylamine.

6. The compound of claim 1, wherein R¹ is phenyl substituted by halogen or CF₃, and R² is hydrogen.

7. The compound of claim 6, selected from the group consisting of
(S)-4-[(3-chloro-phenylamino)-methyl]-4,5-dihydro-oxazol-2-ylamine,
(S)-4-[(2-chloro-phenylamino)-methyl]-4,5-dihydro-oxazol-2-ylamine,
(S)-4-[(4-trifluoromethyl-phenylamino)-methyl]-4,5-dihydro-oxazol-2-ylamine, and
(S)-4-[(2,4-difluoro-phenylamino)-methyl]-4,5-dihydro-oxazol-2-ylamine.

8. The compound of claim 1, wherein R¹ is phenyl substituted by halogen and lower alkyl, and R² is hydrogen.

9. The compound of claim 8, which compound is (S)-4-[(2-fluoro-4-methyl-phenylamino)-methyl]-4,5-dihydro-oxazol-2-ylamine.

10. The compound of claim 1, wherein R¹ is phenyl substituted by CF₃ and lower alkyl or CF₃ alone and R² is lower alkyl.

11. The compound of claim 10, selected from the group consisting of
(S)-4-{[ethyl-(4-trifluoromethyl-phenyl)-amino]-methyl}-4,5-dihydro-oxazol-2-ylamine,
(S)-4-{[methyl-(4-trifluoromethyl-phenyl)-amino]-methyl}-4,5-dihydro-oxazol-2-ylamine, and
(S)-4-{[ethyl-(2-methyl-4-trifluoromethyl-phenyl)-amino]-methyl}-4,5-dihydro-oxazol-2-ylamine.

12. The compound of claim 1, wherein R¹ is pyridine-2-yl and R² is lower alkyl.

13. The compound of claim 12, which compound is ((S)-2-amino-4,5-dihydro-oxazol-4-ylmethyl)-(6-chloro-pyridin-2-yl)-amine.

14. The compound of claim 1, wherein $R^1$ is phenyl, substituted simultaneously by halogen and methoxy.

15. The compound of claim 14, selected from the group consisting of
(S)-4-{[(4-chloro-3-methoxy-phenyl)-methyl-amino]-methyl}-4,5-dihydro-oxazol-2-ylamine,
(S)-4-{[(4-chloro-3-methoxy-phenyl)-ethyl-amino]-methyl}-4,5-dihydro-oxazol-2-ylamine,
(S)-4-{[(4-fluoro-3-methoxy-phenyl)-methyl-amino]-methyl}-4,5-dihydro-oxazol-2-ylamine,
(R)-4-{[(4-fluoro-3-methoxy-phenyl)-methyl-amino]-methyl}-4,5-dihydro-oxazol-2-ylamine,
(R)-4-{[ethyl-(4-fluoro-3-methoxy-phenyl)-amino]-methyl}-4,5-dihydro-oxazol-2-ylamine,
(R)-4-{[(4-chloro-3-methoxy-phenyl)-methyl-amino]-methyl}-4,5-dihydro-oxazol-2-ylamine, and
(R)-4-{[(4-chloro-3-methoxy-phenyl)-ethyl-amino]-methyl}-4,5-dihydro-oxazol-2-ylamine.

16. The compound of claim 1, wherein $R^1$ is phenyl, substituted simultaneously by halogen and methoxy or by halogen and $R^2$ is benzyl.

17. The compound of claim 16, selected from the group consisting of
(S)-4-{[benzyl-(4-fluoro-3-methoxy-phenyl)-amino]-methyl}-4,5-dihydro-oxazol-2-ylamine.
(S)-4-{[benzyl-(4-fluoro-phenyl)-amino]-methyl}-4,5-dihydro-oxazol-2-ylamine, and
(S)-4-{[benzyl-(4-chloro-phenyl)-amino]-methyl}-4,5-dihydro-oxazol-2-ylamine.

18. The compound of claim 1, wherein $R^1$ is phenyl, substituted by lower alkyl and $R^2$ is lower alkyl.

19. The compound of claim 18, selected from the group consisting of
(S)-4-[(ethyl-m-tolyl-amino)-methyl]-4,5-dihydro-oxazol-2-ylamine,
(S)-4-{[ethyl-(3-ethyl-phenyl)-amino]-methyl}-4,5-dihydro-oxazol-2-ylamine, and
(S)-4-{[ethyl-(4-ethyl-phenyl)-amino]-methyl}-4,5-dihydro-oxazol-2-ylamine.

20. The compound of claim 1, wherein $R^1$ is naphthyl and $R^2$ is lower alkyl.

21. The compound of claim 20, selected from the group consisting of
(S)-4-[(methyl-naphthalen-2-yl-aminoymethyl]-4,5-dihydro-oxazol-2-ylamine,
(R)-4-[(methyl-naphthalen-2-yl-amino)-methyl]-4,5-dihydro-oxazol-2-ylamine, and
(R)-4-[(ethyl-naphthalen-2-yl-amino)-methyl]-4,5-dihydro-oxazol-2-ylamine.

22. The compound of claim 1, wherein $R^1$ is phenyl substituted by halogen and $CF_3$.

23. The compound of claim 22, selected from the group consisting of
(S)-4-{[ethyl-(3-fluoro-5-trifluoromethyl-phenyl)-amino]-methyl}-4,5-dihydro-oxazol-2-ylamine.
(S)-4-[(3-fluoro-4-trifluoromethyl-phenylamino)-methyl]-4,5-dihydro-oxazol-2-ylamine, and
(R)-4-{[ethyl-(3-fluoro-5-trifluoromethyl-phenyl)-amino]-methyl}-4,5-dihydro-oxazol-2-ylamine.

24. The compound of claim 1, wherein $R^1$ is indanyl, and $R^2$ is lower alkyl.

25. The compound of claim 24, wherein the compound is (S)-4-[(ethyl-indan-5-yl-amino)-methyl]-4,5-dihydro-oxazol-2-ylamine.

26. The compound of claim 1, wherein $R^1$ is phenyl, substituted by heteroaryl.

27. The compound of claim 24, selected from the group consisting of
(S)-4-{[methyl-(3-oxazol-5-yl-phenyl)-amino]-methyl}-4,5-dihydro-oxazol-2-ylamine, and
(S)-4-{[ethyl-(3-oxazol-5-yl-phenyl)-amino]-methyl}-4,5-dihydro-oxazol-2-ylamine.

28. The compound of claim 1, wherein $R^1$ is phenyl, substituted by lower alkyl and $R^2$ is lower alkyl.

29. The compound of claim 28, selected from the group consisting of
(S)-4-[(ethyl-m-tolyl-amino)-methyl]-4,5-dihydro-oxazol-2-ylamine,
(S)-4-{[ethyl-(3-ethyl-phenyl)-amino]-methyl}-4,5-dihydro-oxazol-2-ylamine, and
(S)-4-{[ethyl-(4-ethyl-phenyl)-amino]-methyl}-4,5-dihydro-oxazol-2-ylamine.

30. The compound of claim 1, having formula IA

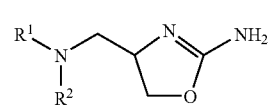

wherein
$R^1$ is aryl, wherein the aryl group is unsubstituted or substituted by one to three substituents, selected from the group consisting of cycloalkyl, phenyl, phenyloxy, benzyl, benzyloxy, halogen, lower alkyl, lower alkoxy, heteroaryl, and lower alkyl substituted by halogen, or is aryl wherein at least one hydrogen atom is replaced by deuterium or tritium; and
$R^2$ is hydrogen, lower alkyl or is benzyl unsubstituted or substituted by alkoxy;
or a pharmaceutically suitable acid addition salt thereof.

31. A pharmaceutical composition comprising a therapeutically effective amount of a compound of formula I

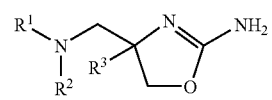

wherein $R^1$ is aryl or heteroaryl, wherein the aryl and heteroaryl groups are unsubstituted or substituted by one to three substituents, selected from the group consisting of cycloalkyl, phenyl, phenyloxy, benzyl, benzyloxy, halogen, lower alkyl, lower alkoxy, heteroaryl, piperidin-1-yl, and lower alkyl substituted by halogen, or is aryl or heteroaryl wherein at least one hydrogen atom is replaced by deuterium or tritium;
$R^2$ is hydrogen, lower alkyl or benzyl unsubstituted or substituted by alkoxy or halogen;
$R^3$ is hydrogen or lower alkyl
or a pharmaceutically suitable acid addition salt thereof and a pharmaceutically acceptable carrier.

* * * * *